US006541218B1

(12) United States Patent
Schuchman et al.

(10) Patent No.: US 6,541,218 B1
(45) Date of Patent: Apr. 1, 2003

(54) ACID SPHINGOMYELINASE PROTEIN AND METHODS OF TREATING TYPE B NIEMANN-PICK DISEASE

(75) Inventors: Edward H. Schuchman, New York, NY (US); Robert J. Desnick, New York, NY (US)

(73) Assignee: The Mount Sinai School of Medicine of the city University of New York, New York, NY (US)

( * ) Notice: Subject to any disclaimer, the term of this patent is extended or adjusted under 35 U.S.C. 154(b) by 0 days.

(21) Appl. No.: 09/106,375

(22) Filed: Jun. 29, 1998

(51) Int. Cl.$^7$ .................. C07H 21/02; C07H 21/04; C12N 9/14; A61K 38/43
(52) U.S. Cl. ............. 435/69.1; 435/71.1; 435/183; 435/195; 435/196; 536/23.5; 536/23.7; 530/350; 514/2
(58) Field of Search ................ 536/23.1, 23.5, 536/23.2; 530/350; 435/69.1, 358, 71.1, 183, 195, 196; 514/2

(56) References Cited

U.S. PATENT DOCUMENTS 5,773,278 A  * 6/1998  Schuchman et al. ........ 435/358

FOREIGN PATENT DOCUMENTS

EP            0 161 788       11/1985

OTHER PUBLICATIONS

Levran et al PNAS 88: 3748–3752 (May 1991).*
Quintern et al. EMBO J. 8(9): 2469–2473 (1989).*
Schuchman et al. AM J. Hum. Genet 45: A217 (1989).*
Miranda, et al. FASEB Journal (Oct. 2000) 14(13): 1988–1995.*
Barton and Neufeld, 1971, "The Hurler corrective factor. Purification and some properties", J. Biol. Chem. 246:7773–7779.
Beutler et al., 1977, "Enzyme replacement therapy in Gaucher's disease: preliminary clinical trial of a new enzyme preparation", Proc. Natl. Acad. Sci. USA 74:4620–4623.
Fischer et al., 1980, "Phosphomannosyl–enzyme receptors in rat liver", J. Biol. Chem. 255:9608–9615.
Furbish et al., 1977, "Enzyme replacement therapy in Gaucher's disease: large–scale purification of glucocerebrosidase suitable for human administration", Proc. Natl. Acad. Sci. USA 74:3560–3563.
Koch et al., 1996, "Molecular cloning and characterization of a full–length complementary DNA encoding human acid ceramidase", J. Biol. Chem. 271:33110–33115.
Krivit et al., 1973, "Prospectus", Birth Defects: Original Article Series IX:232–233.
Levran et al., 1992, "Identification and expression of a common missense mutatin (L302P) in the acid sphingomyelinase gene of Ashkenazi Jewish type A Niemann–Pick disease patients", Blood 80:2081–2087.

Pentchev, 1977, "Enzyme replacement therapy in Gaucher's and Fabry's disease", Ann. Clin. Lab. Sci. 7:251–253.
Takahashi et al., 1992, "Identification and expression of five mutations in the human acid sphingomyelinase gene causing types A and B Niemann–Pick disease. Molecular evidence for genetic heterogeneity in the neuropathic and non–neuropathic forms", J. Biol. Chem. 267:12552–12558.
van der Ploeg et al., 1988, "Prospect for enzyme therapy in glycogenosis II variants: a study on cultured muscle cells", J. Neurol. 235:392–396.
van der Ploeg et al., 1987, "Breakdown of lysosomal glycogen in cultured fibroblasts from glycogenosis type II patients after uptake of acid α–glucosidase", J. Neurological Sci. 79:327–336.
Merril et al., 1979, "Trace polypeptides in cellular extracts and human body fluids detected by two–dimensional electrophoresis and highly sensitive silver stain", Proc. Natl. Acad. Sci. USA 76:4335–4339.
Switzer et al., 1979, "A highly sensitive silver strain for detecting proteins and peptides in polyacrylamide gels", Anal. Biochem. 98:231–237.
Besley and Elleder, 1986, "Enzyme activities and phospholipid storage patterns in brain and spleen samples from Niemann–Pick disease variants: a comparison of neuropathic and non–neuropathic forms", J. Inher. Metab. Dis. 9:59–71.
Besley et al., 1980, "Somatic cell hybridisation studies showing different gene mutations in Niemann–Pick variants", Hum. Genet. 54:409–412.
Brady et al., 1966, "The Metabolism of sphingomyelin. II. Evidence of an enzymatic deficiency in Niemann–Pick disease", Proc. Natl. Acad. Sci. USA 55:366–369.
Callahan et al., 1985, "cDNA clones for human sphingomyelinase isolated using the λgt11 system", Pediat. Res. 19:244a.
Da Veiga Pereira et al., 1991, "Regional assignment of the human acid sphingomyelinase gene (SMPD1) by PCR analysis of somatic cell hybrids and in situ hybridizatin to 11p15.1—p15.4.", Genomics 9:229–234.
Elleder, 1989, "Niemann–Pick disease", Pathol. Res. Pract. 185:293–328.

(List continued on next page.)

Primary Examiner—Carla J. Myers
(74) Attorney, Agent, or Firm—Pennie & Edmonds LLP

(57) ABSTRACT

The present invention relates to the acid sphingomyelinase gene and to methods of diagnosing Niemann-Pick disease. It is based, at least in part, on the cloning and expression of the full-length cDNA encoding acid sphingomyelinase and on the discovery of mutations in the acid sphingomyelinase gene of Ashkenazi Jewish Niemann-Pick disease patients.

18 Claims, 20 Drawing Sheets

OTHER PUBLICATIONS

Figure 1:
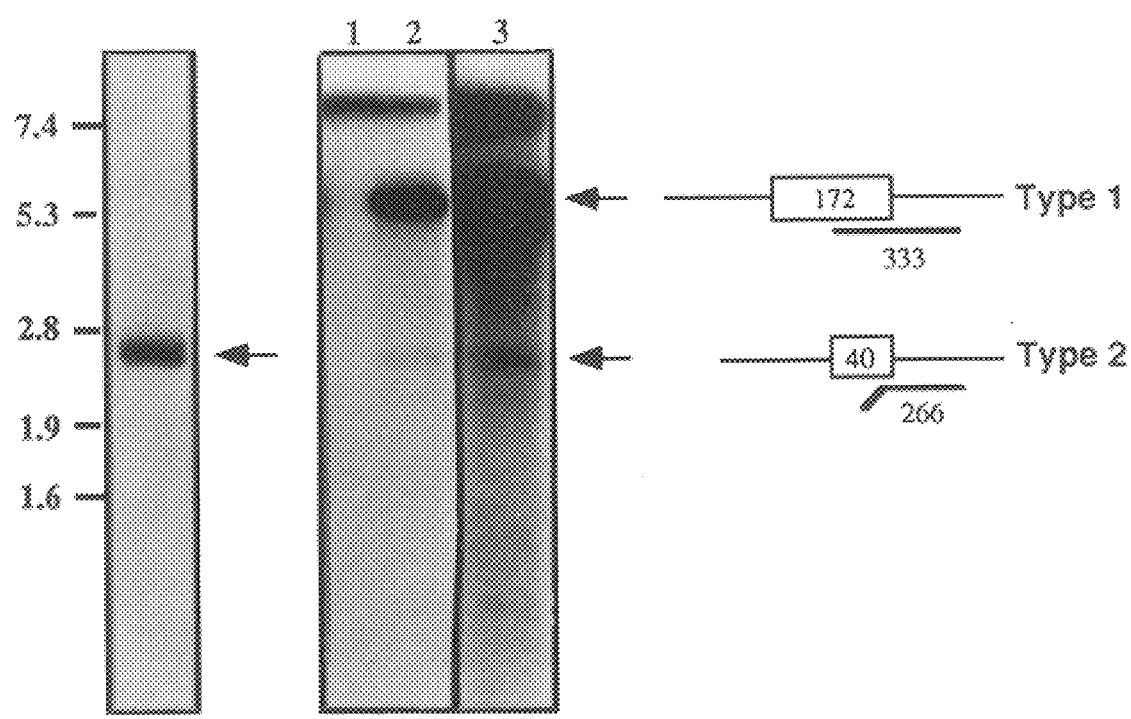

Ferlinz et al., 1991, "Molecular basis of acid sphingomyelinase deficiency in a patient with Niemann–Pick disease type A", Biochem. Biophys. Res. Comm. 179:1187–1191.

Kaufman and Sharp, 1982, "Construction of a modular dihydrofolate reductase cDNA gene: analysis of signals utilized for efficient expression", Mol. Cell. Biol. 2:1304–1319.

Levade et al., 1989, "Sphingomyelinases and Niemann–Pick disease", J. Clin. Chem. Clin. Biochem. 24:205–220.

Levran et al., 1991, "Niemann–Pick disease: a frequent missense mutation in the acid sphingomyelinase gene of Ashkenazi Jewish type A and B patients", Proc. Natl. Acad. Sci. USA 88:3748–3752.

Levran et al., 1991, "Niemann–Pick type B disease. Identification of a single codon deletion in the acid sphingomyelinase gene and genotype/phenotype correlations in type A and B patients", J. Clin. Invest. 88:806–810.

Navon et al., 1989, "The mutations in Ashkenazi Jews with adult GM2 gangliosidosis, the adult form of Tay–Sachs disease", Science 243:1471–1474.

Poulos et al., 1984, "Studies on the activation of sphingomyelinase activity in Niemann–Pick type A, B, and C fibroblasts: enzymological differentiation of types A and B", Pediat. Res. 18:1088–1093.

Quintern et al., 1989, "Isolation of cDNA clones encoding human acid sphingomyelinase: occurrence of alternatively processed transcripts", EMBO J. 8:2469–2473.

Quintern et al., 1987, "Acid sphingomyelinase from human urine: purificatin and characterization", Biochim. Biophys. Acta 922:323–336.

Schneider and Kennedy, 1967, "Sphingomyelinase in normal human spleens and in spleens from subjects with Niemann–Pick disease", J. Lipid Res. 8:202–209.

Schuchmann et al., 1991, "Human acid sphingomyelinase. Isolation, nucleotide Sequence and expression of the full-–length and alternatively spliced cDNAs", J. Biol. Chem. 266:8531–8539.

Schuchman et al., 1989, "Isolation of a full–length cDNA encoding human acid sphingomyelinase: evidence for alternative splicing", Am. J. Hum. Genet. 45(suppl. 4):A217.

Triggs–Raine et al., 1990, "Screening for carriers of Tay–Sachs disease among Ashkenazi Jews. A comparison of DNA–based and enzyme–based tests", N. Eng. J. Med. 323:6–12.

Urlaub et al., 1986, "Effect of gamma rays at the dihydrofolate reductase locus: deletions and inversions.", Somat. Cell Mol. Genet. 12:555–566.

Weiler et al., 1988, "A complementation approach to cloning the gene for acid sphingomyelinase", J. Cell. Biiol. 107:303A.

Sly et al., 1981, "Role of the 6–phosphomannosyl–enzyme receptor in intracellular transport and adsorptive pinocytosis of lysosomal enzymes", Methods Cell Biol. 23:191–214.

Van der Ploeg et al., 1988, "Receptor–mediated uptake of acid alpha–glucosidase corrects lysosomal glycogen storage in cultured skeletal muscle", Pediatr Res. Jul;24(1):90–4.

Desnick et al., 1979, "Enzyme therapy in Fabry disease: differential in vivo plasma clearance and metabolic effectiveness of plasma and splenic alpha–galactosidase A isozymes", Proc Nat. Acad Sci U S A. 76(10):5326–30.

Sando and Neufeld, 1977,"Recognition and receptor–mediated uptake of a lysosomal enzyme, alpha–l–iduronidase, by cultured human fibroblasts", Cell. 12(3):619–27.

Sly WS, 1981, "Prospects for enzyme replacement for lysosomal storage diseases", Birth Defects Orig Artic Ser. 17(1):201–13.

Miranda et al., 2000, "Infusion of recombinant human acid sphingomyelinase into Niemann–Pick disease mice leads to visceral, but not neurological, correction of the pathophysiology", The FASEB Journal 14: 1988–1995.

He et al., 1999, "Characterization of human acid sphingomyelinase pruified from the media of overexpressing Chinese hamster ovary cells", Biochem Biophys Acta. 1432(2):251–64.

Bernardo et al., 1995, "Purification, characterization, and biosynthesis of human acid ceramidase", J Biol Chem. 270(19):11098–102.

Wan and Schuchman, 1995, "A novel polymorphism in the human acid sphingomyelinase gene due to size variation of the signal peptide region", Biochim Biophys Acta. 1270(2–3):207–10.

* cited by examiner

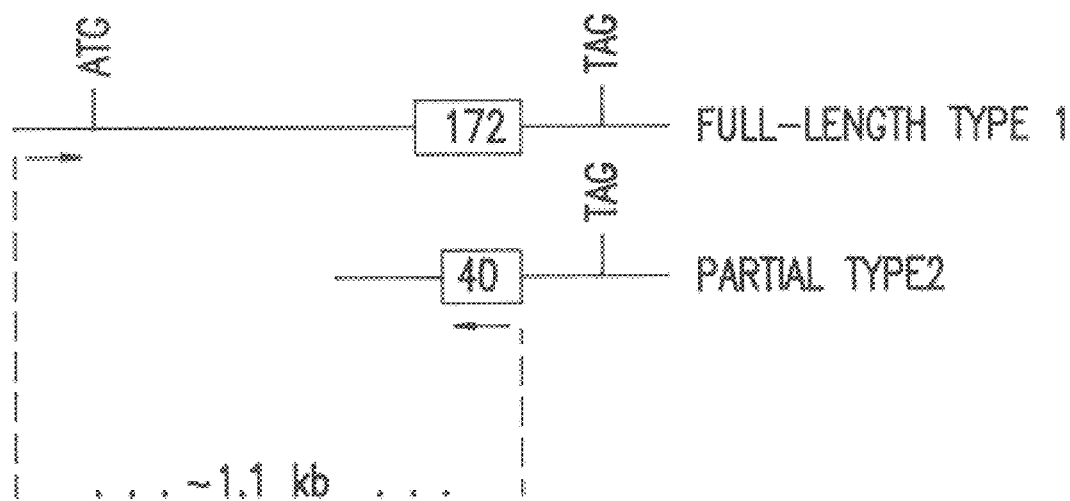
FIG.2C
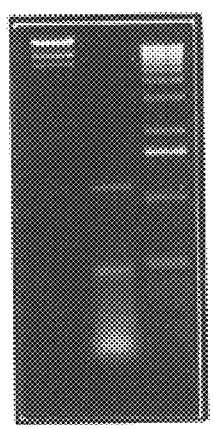 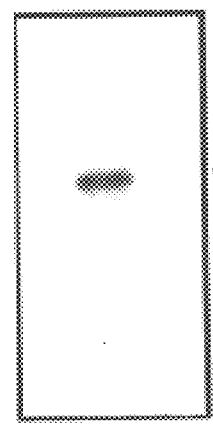
FIG.2A  FIG.2B

```
                                                                          GGCGCCGCCGGGGCCCTGAGGGCTGGCTAGGGTCCAGGCTGAGGGACAGAACCAGCCCGTGTAGGAAGCCGACA   -1
ATG CCC CGC TAC GGA GCG TCA CTC CGC CAG AGC TGC CCC AGG TCC GGC GAG CAG GGA CAA GAC GGG ACC GCC GGA GCC CCC GGA CTC   90
 M   P   R   Y   G   A   S   L   R   Q   S   C   P   R   S   G   R   E   Q   G   Q   D   G   T   A   G   A   P   G   L    30

CTT TGG ATG GGC CTG GTG CTG GCG CTG GCG CTG GCT CTC TGG GCT GTT CTC CGG GTT CTC TGG GCA GAG GCT CAC   180
 L   W   M   G   L   V   L   A   L   A   L   A   L   A   L   S   D   S   R   V   L   V   A   P   A   E   A   H    60

CCT CTT TCT CCC CAA GGC CAT CCT GCC AGG TTA CAT CGC ATA GTG CCC CGG CTC CGA GAT GTC TTT GGG TGG GGG AAC CTC ACC TGC CCA   270
 P   L   S   P   Q   G   H   P   A   R   L   H   R   I   V   P   R   L   R   D   V   F   G   W   G   N   L   T   C   P    90
                                                                                                ──── CHO ────

ATC TGC AAA GGT CTA TTC ACC GCC ATC AAC CTC GGG CTG AAG AAG GAA CCC AAT GTG GCT CGC GTG GGC TCC GTG GCC ATC AAG CTG TGC   360
 I   C   K   G   L   F   T   A   I   N   L   G   L   K   K   E   P   N   V   A   R   V   G   S   V   A   I   K   L   C   120

AAT CTG AAG ATA GCA CCA CCT GCC GTG TGC CAA TCC ATT GTC CAC CTC TTT GAG GAT GAC ATG GTG GAG GTG TGG AGA CGC TCA GTG   450
 N   L   K   I   A   P   P   A   V   C   Q   S   I   V   H   L   F   E   D   D   M   V   E   V   W   R   R   S   V    150

CTG AGC CCA TCT GAG GCC TGT GGC CTG CTC CTG GGC TCC ACC TGT CGG CAC TGG GAC ATT TTC TCA TCT TGG AAC ATC TCT TTG CCT ACT   540
 L   S   P   S   E   A   C   G   L   L   L   G   S   T   C   G   H   W   D   I   F   S   S   W   N   I   S   L   P   T   180
                                                                                    ──── CHO ────

GTG CCG AAG CCG CCC CCC AAA CCC CCT AGC CCC CCA GCC CCT GTC CCG GCC CCA GGT GCG CCC CTG TGC CGC CCG CAC TGG GAT   630
 V   P   K   P   P   P   K   P   P   S   P   P   A   P   V   S   R   I   L   F   L   T   D   L   H   W   D    210

CAT GAC TAC CTG GAG GGC ACG GAC GAC CCT GAC TGT GCA GAC CCT GAC TGT GCA GAC CCA CTG TGC TGC CGG CGG GGT TCT GGC CTG CCG CCA TCC CGG CCA GGT   720
 H   D   Y   L   E   G   T   D   P   D   C   A   D   P   L   C   C   R   R   G   S   G   L   P   P   A   S   R   P   G    240
```

FIG.3A

```
GCC GGA TAC TGG GGC GAA TAC AGC AAG TGT GAC CTG CCC CTG AGG ACC CTG GAG AGC CTG TTG AGT GGG CTG GGC CCA GCC GGC CCT TTT   810
 A   G   Y   W   G   E   Y   S   K   C   D   L   P   L   R   T   L   E   S   L   L   S   G   L   G   P   A   G   P   F    270

GAT ATG GTG TAC TGG ACA GGA GAC ATC CCC GCA CAT GAT GTG TGG CAC CAG ACT CGT CAG GAC CAA CTG CGG GCC CTG ACC GTC ACA        900
 D   M   V   Y   W   T   G   D   I   P   A   H   D   V   W   H   Q   T   R   Q   D   Q   L   R   A   L   T   V   T        300

GCA CTT GTG AGG AAG TTC CTG GGG CCA GTG CCA GTG TAC CCT GTG GGT AAC CAT GAA AGC ATA CCT GTC AAT AGC TTC CCT CCC CCC        990
 A   L   V   R   K   F   L   G   P   V   P   V   Y   P   V   G   N   H   E   S   I   P   V   N   S   F   P   P   P        330

TTC ATT GAG GGC AAC CAC TCC CGC TGG CTC TAT GAA GCT CTT TCC CCA TAC CCC GGT CCC CTC CGC CTC ATC TCT CTC AAT ATG            1080
 F   I   E   G   N   H   S   R   W   L   Y   E   A   L   S   P   Y   P   G   P   L   R   L   I   S   L   N   M            360

CTC AGA ATT GGG GGG TTC TAT GCT CTT TCC CCA GGA CAG CTC CAG TGG CTG GTG GGG GAG CTT CAG GGA CAG CTC CGT GAG AAC TTC        1170
 L   R   I   G   G   F   Y   A   L   S   P   G   Q   L   Q   W   L   V   G   E   L   Q   G   Q   L   R   E   N   F        390

TGG CTC TTG ATC AAC TCC ACG GAT CCC CCA GGG CAC TGT CTG AAG AGC TGG AAT TAT TAC AGG ATT GTA GCC AGG TAT GAG AAC ACC CTG    1260
 W   L   L   I   N   S   T   D   P   P   G   H   C   L   K   S   W   N   Y   Y   R   I   V   A   R   Y   E   N   T   L    420

CAT ATA ATT GGC CAC ATT CCC CCA GGG CAC ACT CAT GTG GAT GAA TTT GAG GTC TTC TAT GAT GAA GAG ACT CTG AGC CGG CCG CTG GCT GTA GCC TTC 1350
 H   I   I   G   H   I   P   P   G   H   T   H   V   D   E   F   E   V   F   Y   D   E   E   T   L   S   R   P   L   A   V   A   F 450

GCT GCT CAG TTC TTT GGC CAC ACT CAT GTG GAT GAA TTT GAG GTC TTC TAT GAT GAA GAG ACT CTG AGC CGG CCG CTG GCT GTA GCC TTC    1440
 A   A   Q   F   F   G   H   T   H   V   D   E   F   E   V   F   Y   D   E   E   T   L   S   R   P   L   A   V   A   F    480
```

FIG.3B

```
CTG GCA CCC AGT GCA ACT ACC TAC ATC GGC CTT AAT CCT GGT TAC CGT GTG TAC CAA ATA GAT GGA AAC TAC TCC AGG AGC TCT CAC GTG   1530
 L   A   P   S   A   T   T   Y   I   G   L   N   P   G   Y   R   V   Y   Q   I   D   G   N   Y   S   R   S   S   H   V    510
                                                                                         CHO

GTC CTG GAC CAT GAG ACC TAC ATC CTG AAT CTG ACC CAG GCA AAC ATA CCG GGA GCC ATA CCG CAC TGG CAG CTT CTC TAC AGG GCT CGA   1620
 V   L   D   H   E   T   Y   I   L   N   L   T   Q   A   N   I   P   G   A   I   P   H   W   Q   L   L   Y   R   A   R    540
                                     CHO

GAA ACC TAT GGG CTG CCC AAC ACA CTG CCT AAC CTG GTA TAT CGC ATG CGG GGC GAC ATG CAA CTT TTC CAG ACC TTC   1710
 E   T   Y   G   L   P   N   T   L   P   N   L   V   Y   R   M   R   G   D   M   Q   L   F   Q   T   F    570
                             CHO

TGG TTT CTC TAC CAT AAG GGC CAC CCA CCC TCG GAG CCC TGT GGC ACG TGC CGT CTG GCT ACT CTT TGT GCC CAG CTC TCT GCC CGT   1800
 W   F   L   Y   H   K   G   H   P   P   S   E   P   C   G   T   C   R   L   A   T   L   C   A   Q   L   S   A   R    600

GCT GAC AGC CCT GCT CTG TGC CGC CAC CTG ATG CCA GAT GGG AGC CTC CCA GAG GCC CAG AGC CTG TGG CCA AGG CCA CTG TTT TGC TAG   1890
 A   D   S   P   A   L   C   R   H   L   M   P   D   G   S   L   P   E   A   Q   S   L   W   P   R   P   L   F   C   *    629

GGCCCCAGGGCCCACATTTGGGAAATTCTTGATGTAGGAAAGGTGAAAAAGCCCAAATGCTGCTGTGTTCAACCAGGCAAGATCATCGGTGAAAGAACCAGTCCTGGCCCAA   2009
GGATGCCGGGGAAACAGGACCTTCTCCTTTCCTGGAGCTGGTTTAGTGCCTGTGCCAGGGGTTTGGCTGTGCTTGAGCTGCTGCTGTCTTTCACAGC   2128
CATGGAGTAGAGGCCTAAGTTGACACTGCCCTGGGCAGACAAGACAAGAGACAGGAGAACCCTGCTACTGCTGCTGCTGTGCCTGTACTGCTGCGACCTGATGCTGCCAGTC   2247
TGTTAAAATAAAG                                                                                                         2260
```

FIG.3C

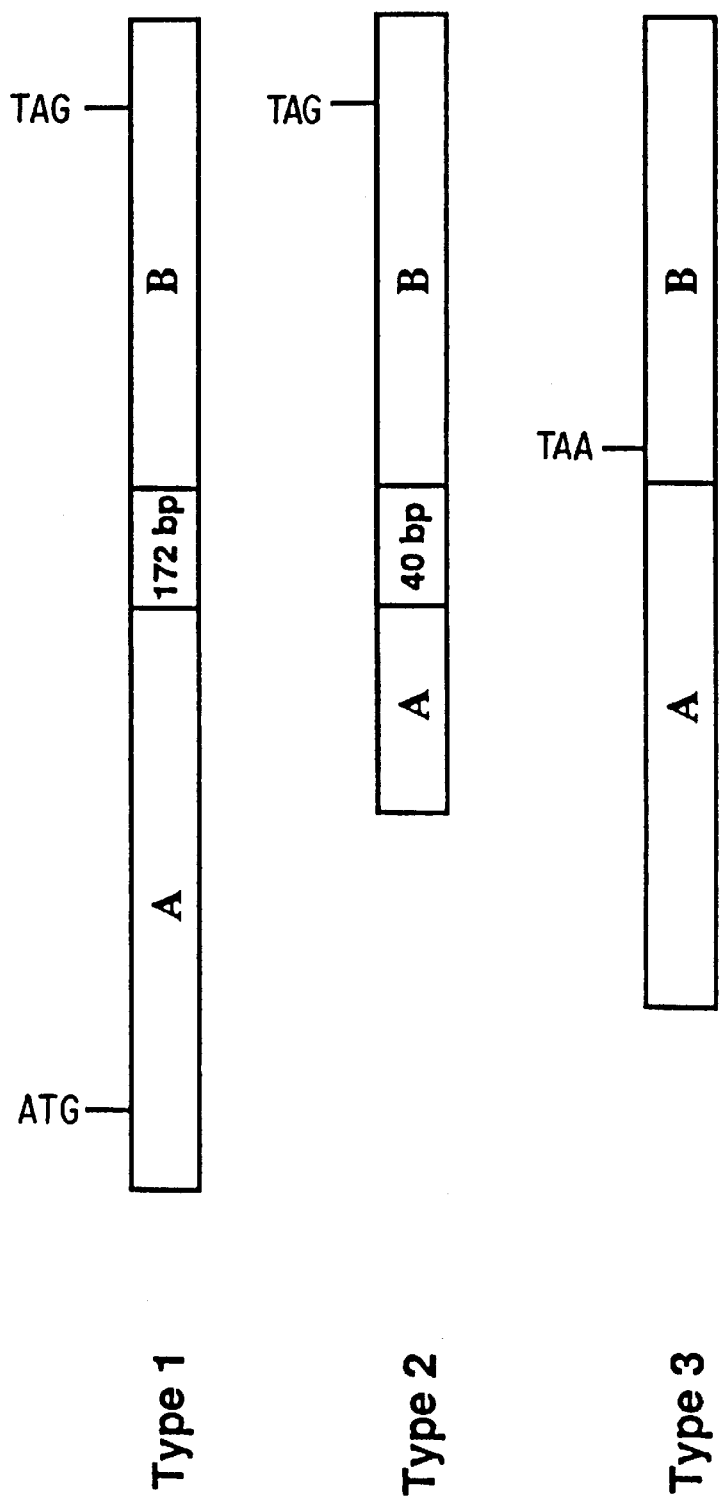

```
                                                      TGGTAACCATGAAAGCACACCTGTCAATAGCTT                34 primer1

CCCTCCCCCTTCATTGAGGGCAACCACTCCTCCCGCTGGCTCTATGAAGCGATGGCCAAGGCTTGGGAGCCCTGCCTGCTGCCGAAGCCCTGCGCACC      134
                                             D3
       D1                                 ┌──────────────┐
┌──────────────┐                          │              │
│TCAGtactt a│tcgtcggtgaaacccaggaaggaaagaga│aggtgaatgaa│ggtgaaagtgaagggagaagggaacctggggcattgtctctgattgctctagc  234 atggtccttagtgctcttcattggctctccctaatctgactctcctcccttttgccgcaccaggctttttttttttagc                           334 tttagttttttgtgagacaagatcttgctatgtgttgccaggctggtctcaaacacctcaacctcaagcaatcctcccgcctcggcctcccaaaatgctggg    434 cacaggcatcagctactgctcctggcctcctggccccctcccttttttttttgagatggaatcttgctctgttgccaggctggagtgcagtggcaa         534 ccatctcagctcactacagcctccacctgggttcaagcaattctgcctcagcctcccaagtacctggactacaggtacctggacctcatgatctgccttcctgaccagct  634 aatttttgtattttttagtagagatgggatttcaccatgttggccaagatggtctcttctactcttatctcttccagccctccccttcaaggtctggcagcataaccttct  734 tgggattacaggcatgaaccactgcaccctgccccagctttccagcccctccccttccacctttctactcttccagccctccccttcaaggtctggcagcataaccttct  834 ctatgcccagctgtgtctttgctcatatttggccctctggaaatgatttccccctttttttaagtgctccagttttccaccttatccatcccatgtc             934

FIG.6A
```

```
1                    20                   40                   60                   80
tcgacagccg cccgccaccg agggatcagc tgtcagagat cagggaaga ggaaggggcg gagctgctttt gcggccggcc ggagcagtca gccgactaca
                                                                  └─sp1──┘
100                  120                  140                  160                  180
ggaagggta atcgggtgtc cccGGCGCCG CCCGGGGCCC TGAGGGCTGG CTAGGGTCCA GGCCGGGGGG GACGGGACAG ACGAACCAGC CCCGTGTAGG 200                  220                  240                  260                  280
AAGCGCGACA ATGCCCCGCT ACGGAGCGTC ACTCCGCCAG AGCTGCCCCA GGTCCGGCCG GGAGCAGGGA CAAGACGGGA CCGCCGGAGC CCCCGGACTC
           ═══
300                  320                  340                  360                  380
CTTTGGATGG GCCTGGCCGG GGGCTGGCG CTGGCCTGG GTCTGACTCT CGGGTTCTCT GGGCTCCGGC AGAGGCTCAC
    ══
400                  420                  440                  460                  480
CCCAAGGCCA TCCTGCCAGG TTACATCGCA TAGTGCCCCG GCTCCGAGAT GTCTTTGGGT GGGGGAACCT CACCTGCCCA ATCTGCAAAG GTCTATTCAC 500                  520                  540                  560                  580
CGCCATCAAC CTCGGGCTGA AGgtgagcac tgaaggggct gcagtggagg ggtgctggg gctggggggct ggggctgatg ctgggggct 600                  620                  640                  660                  680
gggctcagaa tgcatccctg atggagggg tggcattctag aatccatcac tgagtttgct cccctttggg gacacccatg gctacatgcc accatcaccc
                                                                                                    ──ORF 1
700                  720                  740                  760                  780
cattgtgacc tttgtgaagt aagaataat gcagacagtg cctgaggaag tcagcttgcc aagcaaaggc ctcatgccac aggccgctga gctaaagaag
```

FIG.6C

```
800
aagcgatggc ctggtgctgc ctgagttaca gggcaatatc tggaaggcaa aggtgtgcac tggcttggt gcactgagtc ctgccagcc ccagtttgga
                        820                   840                   860                   880
900
aatggaggcc aaggggtggt ggccaggggt tggcctggtt cctctgctct gcctctgatt tctcaccatg cgctcctccc actgcagAAG GAACCCAATG
                        920                   940                   960                   980
1000                  1020                  1040                  1060                  1080
TGGCTCGCGT GGGCTCCGTG GCCATCAAGC TGTGCAATCT GCTGAAGATA GCACCACCTG CCGTGTGCCA ATCCATTGTC CACCTCTTTG AGGATGACAT 1100                  1120                  1140                  1160                  1180
GGTGGAGGTG TGGAGACGCT CAGTGCTGAG CCCATCTGAG GCCTGTGTGG CCCTGTGGCC TGCTCCTGGG CTCCACCTGT GGGCACTGGG ACATTTCTC ATCTTGGAAC 1200                  1220                  1240                  1260                  1280
CGGACACCGG ACGAGGACCC GAGGTGGACA CCCGTGACCC TGTAAAAGAG TAGAACCTTG ATCTCTTTGC CTACTGTGCC GAAGCCGGCC CCCAAACCCC 1300                  1320                  1340                  1360                  1380
CTAGCCCCCC AGCCCCAGGT GCCCCTGTCA GCCGCATCCT CTTCCTCACT GACCTGCACT GGGATCATGA CTACCTGGAG GGCACGGACC CTGACTGTGC
                                            → ORF 2

1400                  1420                  1440                  1460                  1480
AGACCCACTG TGCTGCGCC GGGGTTCTGG CCTGCCGCCG CAGGTGCCGG GCATCCCGGC ATACTGGGGC GAATACAGCA AGTGTGACCT GCCCCTGAGG 1500                  1520                  1540                  1560                  1580
ACCCTGGAGA GCCTGTTGAG TGGGCTGGGC CCAGCCGGCC CTTTTGATAT ACAGGAGACA TCCCCGGACA CTTTTGATAT GGTGTACTGG TGATGTCTGG CACCAGACTC
```

FIG.6D

```
1600                 1620            1640            1660            1680
GTCAGGACCA ACTGCGGGCC CTGACCACCG TCACAGGACT TGTGAGGAAG TTCCTGGGGC CAGTGCCAGT GTACCCTGCT GTGGGTAACC ATGAAAGCAC 1700                 1720            1740            1760            1780
ACCTGTCAAT AGCTTCCCTC CCCCCTTCAT AGTCCCTCCC GCTGGCTCTA TGAAGGCAAC GCCAAGGCTT GGGAGCCCTG GCTGCCTGCC 1800                 1820            1840            1860            1880
GAAGCCCTGC GCACCCTCAG gtacttatcg tccgtgggaa cccaggaagg gaaaagaaag gtgaatgaaa gtgaaggggg aagggaacct gggcattgt 1900                 1920            1940            1960            1980
ctctgattgc tctagcatga gtccttagtg ctcttcattt ggctccccta atctgactcc tccttccctt tctactgttt tgccgcacca ggcttttttt 2000                 2020            2040            2060            2080
tttttttttt ttttagttta gttttttgtag agacaagatc ttgctatgtt gccaggctg gtctcaaaca cctaacctca agcaatcctc ccgcctcggc 2100                 2120            2140            2160            2180
ctcccaaaat gctgggacca caggcatcag ctactgctcc tggccctccc tttttttttt ttttttttttt gagatggaat cttgctctgt 2200                 2220            2240            2260            2280
tgccaggct gggtgcagt ggcaccatct cagctcacta cagcctcac ctcctgggtt caagcaattc tgcctcagcc tcccagtac ctgggactac 2300                 2320            2340            2360            2380
aggtgcacgc caccacacc agctaattttt tgtatttttta gtagagatgg ggtttcacca tgttggccaa gatggtcttg atcttcctgac ctcatgatct
```

FIG. 6E

```
2400                    2420                    2440                    2460                    2480
gccacctcg gcctccaaa gtgctgggat tacaggcatg aaccactgca cccaggtttc cagccctccc tttctactct tatctccagc caccctcctt
                                                                   ← Alu 1
2500                    2520                    2540                    2560                    2580
caaggtctg gcagcataac ctttctatgc cccagctgtgt cttttgctca tgttggccct ctggaaatga tttcccccctt ttttttaagt gctccagtttt 2600                    2620                    2640                    2660                    2680
ttccacctt atccatccca tgtcatcttc cctctgtgtg gtccttgctt cccattctag ctaactctta tccctcccc atactcctgg agccctctgc 2700                    2720                    2740                    2760                    2780
cctcagatgc tttttgtgtca cacagaccca ataattagaa ctgtttggtc ctgtgagctc cttgcaggtg gggagatgt catgtatgct
  ORF3 →
2800                    2820                    2840                    2860                    2880
tttaccctcc accaaatgc ccagcacagg aggaccagga ttgaacaag tgttgacctc tcatgtttac tttgtttcag AATTGGGGGG TTCTATGCTC 2900                    2920                    2940                    2960                    2980
TTTCCCCATA CCCCGGTCTC CGCCTCATCT CTCTCAATAT GAATTTTTGT TCCCGTGAGA ACTTCTGGCT CTTGATCAAC TCCACGGATC CCGCAGGACA 3000                    3020                    3040                    3060                    3080
GCTCCAGTGG CTGGTGGGG AGCTTCAGGC TGCTGAGGAT CGAGGAGACA AAgtgagggc cagtagtggg aacacggtgg tgctggggga caagcaggct 3100                    3120                    3140                    3160                    3180
cctgttgagc ctgggcacct ctgggcacag aagttttatt ttcctggcat tgttccctgg ggattcagct catggtcact gttgaaagcc
```

FIG.6F

```
3200                     3220                     3240                     3260                     3280
     ttcattcagt ccccctttct ctagccaggg ctgcctggac cctgattacc cctgattgatgc atccttaatt ctccctacta gGTGCATATA ATTGGCCACA
3300                     3320                     3340                     3360                     3380
     TTCCCCCAGG GCACTGTCTG AAGAGCTGGA GCTGGAATTA TTACCGAATT GTAGCCAGgt aggacgggga tgagggtggg aatagggaca gggtgagtgt
3400                     3420                     3440                     3460                     3480
     ctgaaggctg aaaattccct tggcatctc accatccctg ttgtccatg gagtggggag gctcctcact agaacaggtt gggaaagag ggcatcctat
3500                     3520                     3540                     3560                     3580
     ctcccagat gtcttcctac ccctcctag aatcttctga atgtagtacc ttctggccag GTATGAGAAC ACCCTGGCTG CTCAGTTCTT TGCCCACACT
3600                     3620                     3640                     3660                     3680
     CATGTGGATG AATTGAGGT CTTCTATGAT GAAGAGACTC TGAGCGGGCC GCTGGCTGTA GCCTTCCTGG CACCCAGTGC AACTACCTAC ATCGGCCTTA
3700                     3720                     3740                     3760                     3780
     ATCCTGgtga gtgaggcaga agggagcctc ccttatcctg gagttggtgg gatagggga gggaggttgga gccagagcct gcaaagcatg ggcaggatgt
3800                     3820                     3840                     3860                     3880
     gtggccctc cctggagtta ccctttgctcc agtcagcccc acatccttgc agGTTACCGT GTGTACCAAA TAGATGGAAA CTACTCCGGG
3900                     3920                     3940                     3960                     3980
     AGCTCTCACG TGGTCCTGGA CCATGAGACC TACATCCTGA ATCTGACCCA GGCAAACATA CCGGGAGCCA TACCGCACTG GCAGCTTCTC TACAGGGCTC
```

FIG.6G

```
4000                    4020                    4040                    4060                    4080
GAGAAACCTA TGGGCTGCCC AACACACTGC CTACCGCCTG GCACAACCTG GTATATCGCA TGCGGGGCGA CATGCAACTT TTCCAGACCT TCTGGTTTCT 4100                    4120                    4140                    4160                    4180
CTACCATAAG GGCCACCCAC CCTGGGAGCC CCGTGGCACG CCCTGCCGTC TGGCTACTCT TTGTGCCCAG CTCTCTGCCC GTGCTGACAG CCCTGCTCTG 4200                    4220                    4240                    4260                    4280
TGCCGCCACC TGATGCCAGA TGGGAGCCTC CCAGAGGCCC AGAGCCTGTG GCCAAGGCCA CTGTTTTGCT AGGGCCCCAG GGCCCACATT TGGGAAAGTT 4300                    4320                    4340                    4360                    4380
CTTGATGTAG GAAAGGGTGA AAAAGCCCAA ATGCTGCTGT GGTTCAACCA GGCAAGATCA TCCGGTGAAA GAACCAGTCC CTGGGCCCCA AGGATGCCGG 4400                    4420                    4440                    4460                    4480
GGAAACAGGA CCTTCTCCTT TCCTGGAGCT GGTTTAGCTG GATATGGGAG GGGGTTTGGC TGCCTGTGCC CAGGAGCTAG ACTGCCTTGA GGCTGCTGTC 4500                    4520                    4540                    4560                    4580
CTTTCACAGC CATGGAGTAG AGGCCTAAGT TGACACTGCC CTGGGCAGAC AAGACAGGAG CTGTCGCCCC AGGCCTGTGC TGCCCAGCCA GGAACCCTGT 4600                    4620                    4640                    4660                    4680
ACTGCTGCTG CGACCTGATG CTGCCAGTCT GTTAAAATAA Agataagaga cttggactcc agaccctgt gtgactgtcc caatttcttc tttccagca 4700
agcagggcaa gaagatcttt gggcaagat cataactgag g
```

FIG.6H

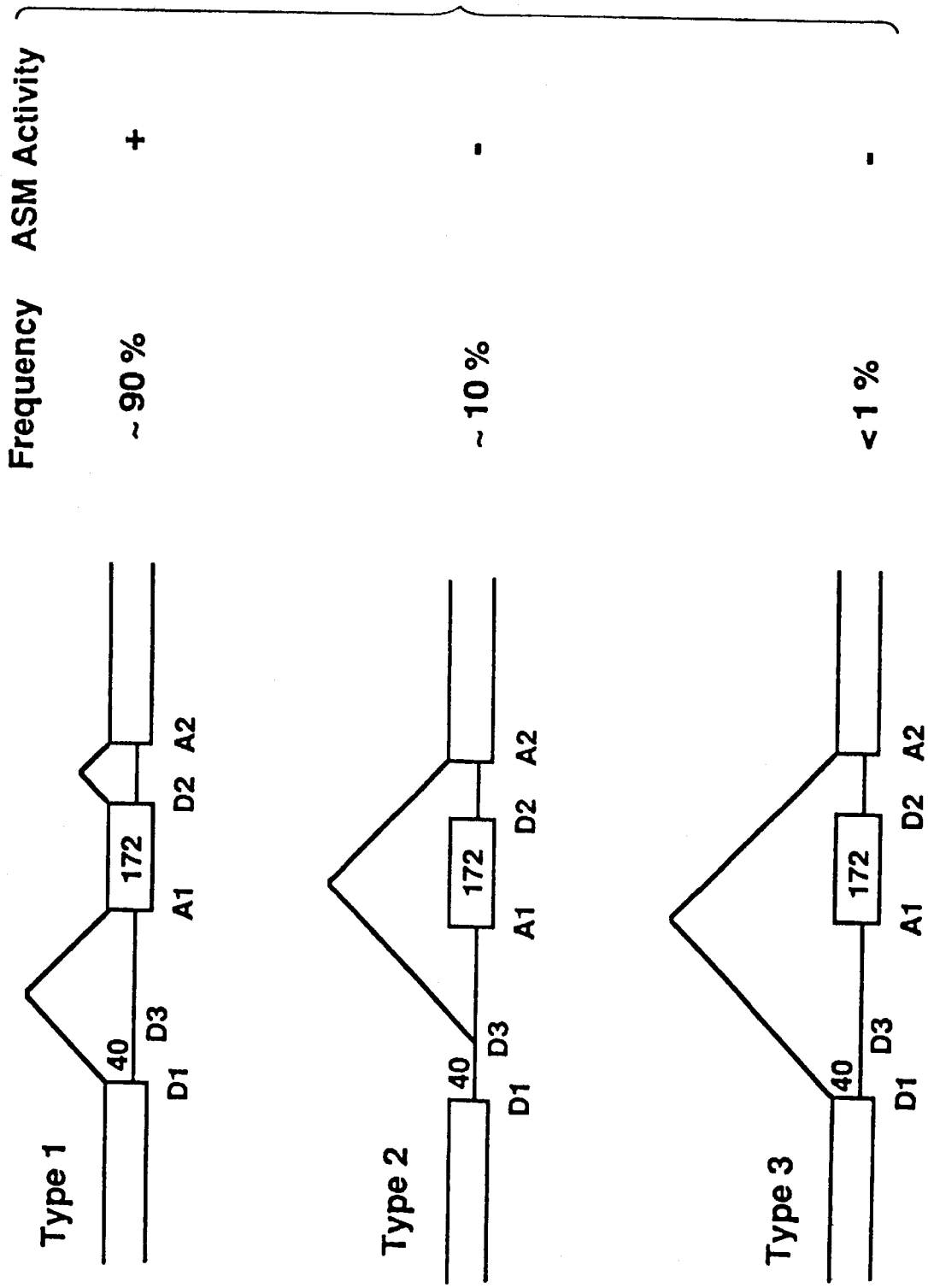

```
         606  607  608  609  610
         Leu  Cys  Arg  His  Leu

NORMAL:  5'- CTG  TGC  CGC  CAC  CTG -3'

ΔR608:   5'- CTG  TG        C  CAC  CTG -3'

Leu     Cys     His   Leu
              606     607     608   609
```

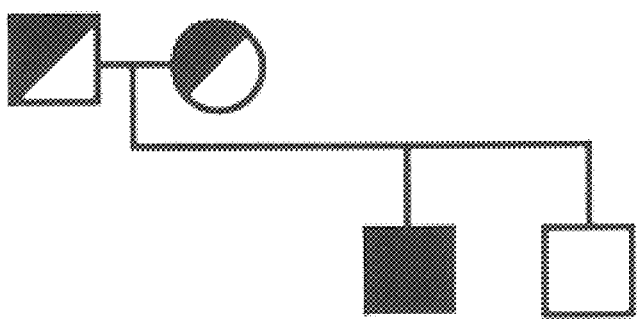
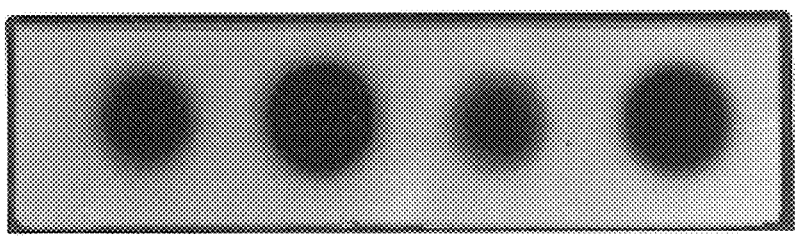
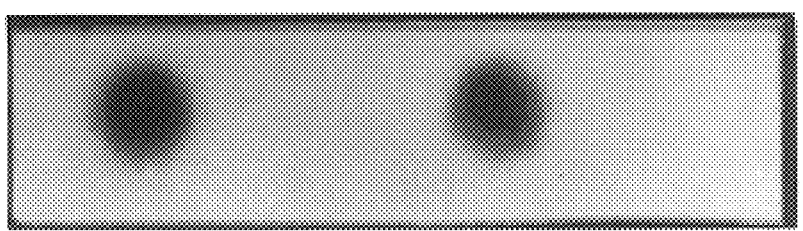
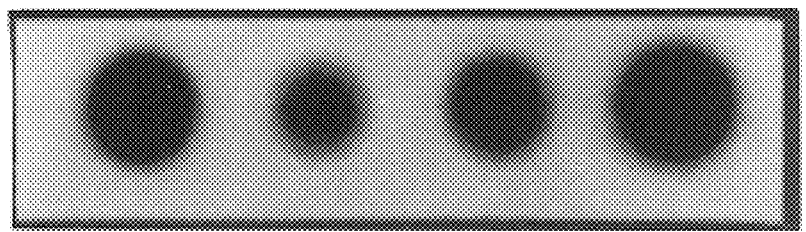
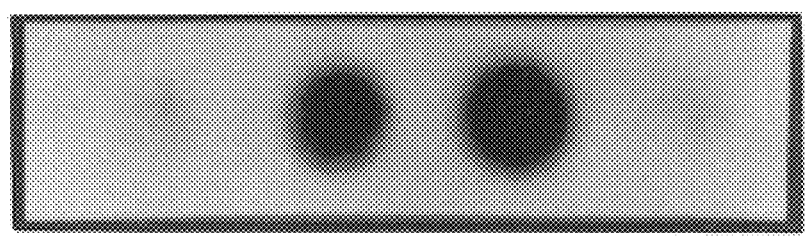
FIG. 11

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 2347 base pairs
      (B) TYPE: nucleic acid
      (C) STRANDEDNESS: single
      (D) TOPOLOGY: unknown (ii) MOLECULE TYPE: cDNA (ix) FEATURE:
      (A) NAME/KEY: CDS
      (B) LOCATION: 88..1977

(xi) SEQUENCE DESCRIPTION: SEQ ID NO:1:

```
GGCGCCGCCC GGGGCCCTGA GGGCTGGCTA GGGTCCAGGC CGGGGGGGAC GGGACAGACG           60

AACCAGCCCC GTGTAGGAAG CGCGACA ATG CCC CGC TAC GGA GCG TCA CTC              111
                              Met Pro Arg Tyr Gly Ala Ser Leu
                                1               5

CGC CAG AGC TGC CCC AGG TCC GGC CGG GAG CAG GGA CAA GAC GGG ACC            159
Arg Gln Ser Cys Pro Arg Ser Gly Arg Glu Gln Gly Gln Asp Gly Thr
     10                  15                  20

GCC GGA GCC CCC GGA CTC CTT TGG ATG GGC CTG GTG CTG GCG CTG GCG            207
Ala Gly Ala Pro Gly Leu Leu Trp Met Gly Leu Val Leu Ala Leu Ala
 25                  30                  35                  40

CTG GCG CTG GCG CTG GCT CTG TCT GAC TCT CGG GTT CTC TGG GCT CCG            255
Leu Ala Leu Ala Leu Ala Leu Ser Asp Ser Arg Val Leu Trp Ala Pro
                     45                  50                  55

GCA GAG GCT CAC CCT CTT TCT CCC CAA GGC CAT CCT GCC AGG TTA CAT            303
Ala Glu Ala His Pro Leu Ser Pro Gln Gly His Pro Ala Arg Leu His
                 60                  65                  70

CGC ATA GTG CCC CGG CTC CGA GAT GTC TTT GGG TGG GGG AAC CTC ACC            351
Arg Ile Val Pro Arg Leu Arg Asp Val Phe Gly Trp Gly Asn Leu Thr
         75                  80                  85

TGC CCA ATC TGC AAA GGT CTA TTC ACC GCC ATC AAC CTC GGG CTG AAG            399
Cys Pro Ile Cys Lys Gly Leu Phe Thr Ala Ile Asn Leu Gly Leu Lys
     90                  95                 100

AAG GAA CCC AAT GTG GCT CGC GTG GGC TCC GTG GCC ATC AAG CTG TGC            447
Lys Glu Pro Asn Val Ala Arg Val Gly Ser Val Ala Ile Lys Leu Cys
105                 110                 115                 120
```

-continued

```
AAT CTG CTG AAG ATA GCA CCA CCT GCC GTG TGC CAA TCC ATT GTC CAC        495
Asn Leu Leu Lys Ile Ala Pro Pro Ala Val Cys Gln Ser Ile Val His
            125                 130                 135

CTC TTT GAG GAT GAC ATG GTG GAG GTG TGG AGA CGC TCA GTG CTG AGC        543
Leu Phe Glu Asp Asp Met Val Glu Val Trp Arg Arg Ser Val Leu Ser
            140                 145                 150

CCA TCT GAG GCC TGT GGC CTG CTC CTG GGC TCC ACC TGT GGG CAC TGG        591
Pro Ser Glu Ala Cys Gly Leu Leu Leu Gly Ser Thr Cys Gly His Trp
            155                 160                 165

GAC ATT TTC TCA TCT TGG AAC ATC TCT TTG CCT ACT GTG CCG AAG CCG        639
Asp Ile Phe Ser Ser Trp Asn Ile Ser Leu Pro Thr Val Pro Lys Pro
170             175                 180

CCC CCC AAA CCC CCT AGC CCC CCA GCC CCA GGT GCC CCT GTC AGC CGC        687
Pro Pro Lys Pro Pro Ser Pro Pro Ala Pro Gly Ala Pro Val Ser Arg
185             190                 195                 200

ATC CTC TTC CTC ACT GAC CTG CAC TGG GAT CAT GAC TAC CTG GAG GGC        735
Ile Leu Phe Leu Thr Asp Leu His Trp Asp His Asp Tyr Leu Glu Gly
                205                 210                 215

ACG GAC CCT GAC TGT GCA GAC CCA CTG TGC TGC CGC CGG GGT TCT GGC        783
Thr Asp Pro Asp Cys Ala Asp Pro Leu Cys Cys Arg Arg Gly Ser Gly
                220                 225                 230

CTG CCG CCC GCA TCC CGG CCA GGT GCC GGA TAC TGG GGC GAA TAC AGC        831
Leu Pro Pro Ala Ser Arg Pro Gly Ala Gly Tyr Trp Gly Glu Tyr Ser
                235                 240                 245

AAG TGT GAC CTG CCC CTG AGG ACC CTG GAG AGC CTG TTG AGT GGG CTG        879
Lys Cys Asp Leu Pro Leu Arg Thr Leu Glu Ser Leu Leu Ser Gly Leu
            250                 255                 260

GGC CCA GCC GGC CCT TTT GAT ATG GTG TAC TGG ACA GGA GAC ATC CCC        927
Gly Pro Ala Gly Pro Phe Asp Met Val Tyr Trp Thr Gly Asp Ile Pro
265             270                 275                 280

GCA CAT GAT GTC TGG CAC CAG ACT CGT CAG GAC CAA CTG CGG GCC CTG        975
Ala His Asp Val Trp His Gln Thr Arg Gln Asp Gln Leu Arg Ala Leu
                285                 290                 295

ACC ACC GTC ACA GCA CTT GTG AGG AAG TTC CTG GGG CCA GTG CCA GTG       1023
Thr Thr Val Thr Ala Leu Val Arg Lys Phe Leu Gly Pro Val Pro Val
                300                 305                 310

TAC CCT GCT GTG GGT AAC CAT GAA AGC ATA CCT GTC AAT AGC TTC CCT       1071
Tyr Pro Ala Val Gly Asn His Glu Ser Ile Pro Val Asn Ser Phe Pro
            315                 320                 325

CCC CCC TTC ATT GAG GGC AAC CAC TCC TCC CGC TGG CTC TAT GAA GCG       1119
Pro Pro Phe Ile Glu Gly Asn His Ser Ser Arg Trp Leu Tyr Glu Ala
            330                 335                 340

ATG GCC AAG GCT TGG GAG CCC TGG CTG CCT GCC GAA GCC CTG CGC ACC       1167
Met Ala Lys Ala Trp Glu Pro Trp Leu Pro Ala Glu Ala Leu Arg Thr
345             350                 355                 360

CTC AGA ATT GGG GGG TTC TAT GCT CTT TCC CCA TAC CCC GGT CTC CGC       1215
Leu Arg Ile Gly Gly Phe Tyr Ala Leu Ser Pro Tyr Pro Gly Leu Arg
                365                 370                 375

CTC ATC TCT CTC AAT ATG AAT TTT TGT TCC CGT GAG AAC TTC TGG CTC       1263
Leu Ile Ser Leu Asn Met Asn Phe Cys Ser Arg Glu Asn Phe Trp Leu
                380                 385                 390

TTG ATC AAC TCC ACG GAT CCC GCA GGA CAG CTC CAG TGG CTG GTG GGG       1311
Leu Ile Asn Ser Thr Asp Pro Ala Gly Gln Leu Gln Trp Leu Val Gly
            395                 400                 405

GAG CTT CAG GCT GCT GAG GAT CGA GGA GAC AAA GTG CAT ATA ATT GGC       1359
Glu Leu Gln Ala Ala Glu Asp Arg Gly Asp Lys Val His Ile Ile Gly
            410                 415                 420

CAC ATT CCC CCA GGG CAC TGT CTG AAG AGC TGG AGC TGG AAT TAT TAC       1407
His Ile Pro Pro Gly His Cys Leu Lys Ser Trp Ser Trp Asn Tyr Tyr
425             430                 435                 440
```

```
CGA ATT GTA GCC AGG TAT GAG AAC ACC CTG GCT GCT CAG TTC TTT GGC    1455
Arg Ile Val Ala Arg Tyr Glu Asn Thr Leu Ala Ala Gln Phe Phe Gly
            445                 450                 455

CAC ACT CAT GTG GAT GAA TTT GAG GTC TTC TAT GAT GAA GAG ACT CTG    1503
His Thr His Val Asp Glu Phe Glu Val Phe Tyr Asp Glu Glu Thr Leu
            460                 465                 470

AGC CGG CCG CTG GCT GTA GCC TTC CTG GCA CCC AGT GCA ACT ACC TAC    1551
Ser Arg Pro Leu Ala Val Ala Phe Leu Ala Pro Ser Ala Thr Thr Tyr
            475                 480                 485

ATC GGC CTT AAT CCT GGT TAC CGT GTG TAC CAA ATA GAT GGA AAC TAC    1599
Ile Gly Leu Asn Pro Gly Tyr Arg Val Tyr Gln Ile Asp Gly Asn Tyr
            490                 495                 500

TCC AGG AGC TCT CAC GTG GTC CTG GAC CAT GAG ACC TAC ATC CTG AAT    1647
Ser Arg Ser Ser His Val Val Leu Asp His Glu Thr Tyr Ile Leu Asn
505                 510                 515                 520

CTG ACC CAG GCA AAC ATA CCG GGA GCC ATA CCG CAC TGG CAG CTT CTC    1695
Leu Thr Gln Ala Asn Ile Pro Gly Ala Ile Pro His Trp Gln Leu Leu
                525                 530                 535

TAC AGG GCT CGA GAA ACC TAT GGG CTG CCC AAC ACA CTG CCT ACC GCC    1743
Tyr Arg Ala Arg Glu Thr Tyr Gly Leu Pro Asn Thr Leu Pro Thr Ala
            540                 545                 550

TGG CAC AAC CTG GTA TAT CGC ATG CGG GGC GAC ATG CAA CTT TTC CAG    1791
Trp His Asn Leu Val Tyr Arg Met Arg Gly Asp Met Gln Leu Phe Gln
            555                 560                 565

ACC TTC TGG TTT CTC TAC CAT AAG GGC CAC CCA CCC TCG GAG CCC TGT    1839
Thr Phe Trp Phe Leu Tyr His Lys Gly His Pro Pro Ser Glu Pro Cys
            570                 575                 580

GGC ACG CCC TGC CGT CTG GCT ACT CTT TGT GCC CAG CTC TCT GCC CGT    1887
Gly Thr Pro Cys Arg Leu Ala Thr Leu Cys Ala Gln Leu Ser Ala Arg
585                 590                 595                 600

GCT GAC AGC CCT GCT CTG TGC CGC CAC CTG ATG CCA GAT GGG AGC CTC    1935
Ala Asp Ser Pro Ala Leu Cys Arg His Leu Met Pro Asp Gly Ser Leu
                605                 610                 615

CCA GAG GCC CAG AGC CTG TGG CCA AGG CCA CTG TTT TGC TAGGGCCCCA     1984
Pro Glu Ala Gln Ser Leu Trp Pro Arg Pro Leu Phe Cys
            620                 625                 630

GGGCCCACAT TTGGGAAAGT TCTTGATGTA GGAAAGGGTG AAAAAGCCCA AATGCTGCTG    2044

TGGTTCAACC AGGCAAGATC ATCCGGTGAA AGAACCAGTC CCTGGGCCCC AAGGATGCCG    2104

GGGAAACAGG ACCTTCTCCT TTCCTGGAGC TGGTTTAGCT GGATATGGGA GGGGGTTTGG    2164

CTGCCTGTGC CCAGGAGCTA GACTGCCTTG AGGCTGCTGT CCTTTCACAG CCATGGAGTA    2224

GAGGCCTAAG TTGACACTGC CCTGGGCAGA CAAGACAGGA GCTGTCGCCC AGGCCTGTG     2284

CTGCCCAGCC AGGAACCCTG TACTGCTGCT GCGACCTGAT GCTGCCAGTC TGTTAAAATA    2344

AAG                                                                  2347

(2) INFORMATION FOR SEQ ID NO:2:

(i) SEQUENCE CHARACTERISTICS:
        (A) LENGTH: 629 amino acids
        (B) TYPE: amino acid
        (D) TOPOLOGY: unknown (ii) MOLECULE TYPE: protein (xi) SEQUENCE DESCRIPTION: SEQ ID NO:2:

Met Pro Arg Tyr Gly Ala Ser Leu Arg Gln Ser Cys Pro Arg Ser Gly
  1               5                  10                  15

Arg Glu Gln Gly Gln Asp Gly Thr Ala Gly Ala Pro Gly Leu Leu Trp
```

-continued

```
                 20                  25                  30
Met Gly Leu Val Leu Ala Leu Ala Leu Ala Leu Ala Leu Ser
             35                  40                  45

Asp Ser Arg Val Leu Trp Ala Pro Ala Glu Ala His Pro Leu Ser Pro
 50                  55                  60

Gln Gly His Pro Ala Arg Leu His Arg Ile Val Pro Arg Leu Arg Asp
 65                  70                  75                  80

Val Phe Gly Trp Gly Asn Leu Thr Cys Pro Ile Cys Lys Gly Leu Phe
                 85                  90                  95

Thr Ala Ile Asn Leu Gly Leu Lys Lys Glu Pro Asn Val Ala Arg Val
             100                 105                 110

Gly Ser Val Ala Ile Lys Leu Cys Asn Leu Leu Lys Ile Ala Pro Pro
             115                 120                 125

Ala Val Cys Gln Ser Ile Val His Leu Phe Glu Asp Asp Met Val Glu
             130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                 165                 170                 175

Ser Leu Pro Thr Val Pro Lys Pro Pro Lys Pro Pro Ser Pro Pro
             180                 185                 190

Ala Pro Gly Ala Pro Val Ser Arg Ile Leu Phe Leu Thr Asp Leu His
             195                 200                 205

Trp Asp His Asp Tyr Leu Glu Gly Thr Asp Pro Asp Cys Ala Asp Pro
             210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                 245                 250                 255

Leu Glu Ser Leu Leu Ser Gly Leu Gly Pro Ala Gly Pro Phe Asp Met
             260                 265                 270

Val Tyr Trp Thr Gly Asp Ile Pro Ala His Asp Val Trp His Gln Thr
             275                 280                 285

Arg Gln Asp Gln Leu Arg Ala Leu Thr Thr Val Thr Ala Leu Val Arg
             290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Pro Phe Ile Glu Gly Asn His
                 325                 330                 335

Ser Ser Arg Trp Leu Tyr Glu Ala Met Ala Lys Ala Trp Glu Pro Trp
             340                 345                 350

Leu Pro Ala Glu Ala Leu Arg Thr Leu Arg Ile Gly Gly Phe Tyr Ala
             355                 360                 365

Leu Ser Pro Tyr Pro Gly Leu Arg Leu Ile Ser Leu Asn Met Asn Phe
             370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
             405                 410                 415

Gly Asp Lys Val His Ile Ile Gly His Ile Pro Pro Gly His Cys Leu
             420                 425                 430

Lys Ser Trp Ser Trp Asn Tyr Tyr Arg Ile Val Ala Arg Tyr Glu Asn
             435                 440                 445
```

```
Thr Leu Ala Ala Gln Phe Phe Gly His Thr His Val Asp Glu Phe Glu
    450                 455                 460
Val Phe Tyr Asp Glu Glu Thr Leu Ser Arg Pro Leu Ala Val Ala Phe
465                 470                 475                 480
Leu Ala Pro Ser Ala Thr Thr Tyr Ile Gly Leu Asn Pro Gly Tyr Arg
            485                 490                 495
Val Tyr Gln Ile Asp Gly Asn Tyr Ser Arg Ser His Val Val Leu
            500                 505                 510
Asp His Glu Thr Tyr Ile Leu Asn Leu Thr Gln Ala Asn Ile Pro Gly
            515                 520                 525
Ala Ile Pro His Trp Gln Leu Leu Tyr Arg Ala Arg Glu Thr Tyr Gly
            530                 535                 540
Leu Pro Asn Thr Leu Pro Thr Ala Trp His Asn Leu Val Tyr Arg Met
545                 550                 555                 560
Arg Gly Asp Met Gln Leu Phe Gln Thr Phe Trp Phe Leu Tyr His Lys
                565                 570                 575
Gly His Pro Pro Ser Glu Pro Cys Gly Thr Pro Cys Arg Leu Ala Thr
            580                 585                 590
Leu Cys Ala Gln Leu Ser Ala Arg Ala Asp Ser Pro Ala Leu Cys Arg
            595                 600                 605
His Leu Met Pro Asp Gly Ser Leu Pro Glu Ala Gln Ser Leu Trp Pro
    610                 615                 620
Arg Pro Leu Phe Cys
625

(2) INFORMATION FOR SEQ ID NO:3:

(i) SEQUENCE CHARACTERISTICS:
        (A) LENGTH: 1664 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:3:

TGGGTAACCA TGAAAGCACA CCTGTCAATA GCTTCCCTCC CCCCTTCATT GAGGGCAACC      60

ACTCCTCCCG CTGGCTCTAT GAAGCGATGG CCAAGGCTTG GGAGCCCTGG CTGCCTGCCG     120

AAGCCCTGCG CACCTCAGGT ACTTATCGTC CGTGGAAACC CAGGAAGGGA AAAGAAAGGT     180

GAATGAAAGT GAAGGGAGAA GGGAACCTGG GGCATTGTCT CTGATTGCTC TAGCATGAGT     240

CCTTAGTGCT CTTCATTTGG CTCCCCTAAT CTGACTCCTC CTTCCCTTTC TACTGTTTTG     300

CCGCACCAGG CTTTTTTTTT TTTTTTTTT TAGCTTTAGT TTTTGTAGAG ACAAGATCTT      360

GCTATGTTGC CCAGGCTGGT CTCAAACACC TAACCTCAAG CAATCCTCCC GCCTCGGCCT     420

CCCAAAATGC TGGGCACAGG CATCAGCTAC TGCTCCTGGC CCTCCCTTTT TTTTTTTTT     480

TTTTTTTTG AGATGGAATC TTGCTCTGTT GCCCAGGCTG GAGTGCAGTG GCAACCATCT     540

CAGCTCACTA CAGCCTCCAC CTCCTGGGTT CAAGCAATTC TGCCTCAGCC TCCCAAGTAC     600

CTGGGACTAC AGGTGCACGC CACCACACCC AGCTAATTTT TGTATTTTTA GTAGAGATGG     660

GGTTTCACCA TGTTGGCCAA GATGGTCTTG ATCTCCTGAC CTCATGATCT GCCCACCTCG     720

GCCTCCCAAA GTGCTGGGAT TACAGGCATG AACCACTGCA CCCAGCTTTC AGCCCTCCC     780

TTTCTACTCT TATCTCCAGC CACCCTCCTT CAAAGGTCTG GCAGCATAAC CTCTCTATGC     840

CCCAGCTGTG TCTTTGCTCA TATTGGCCCT CTGGAAATGA TTTCCCCCTT TTTTTTAAGT     900
```

-continued

```
GCTCCAGTTT TTCCCACCTT ATCCATCCCA TGTCATCTTC CCTCTGTGTG GTCCTTGCTT      960

CCCATTCTAG CTAACTCTTA TCCCTCCCCC ATACTCCTGG AGCCCTCTGC CCTCAGAGTC     1020

TTTTGTGTCA CACAGACCCA ATAATTAGAA CTGTTTGGTC TCTGGCTAGA CTGTGAGCTC     1080

CTTGCAGGTG GGGAAGATGT CATGTATGCT TTTACCCTCC ACCCAAATGC CCAGCACAGG     1140

AGGACCAGGA TTGGAACAAG TGTTGACCTC TCATGTTTAC TTTGTTTCAG AATTGGGGGG     1200

TTCTATGCTC TTTCCCCATA CCCCGGTCTC CGCCTCATCT CTCTCAATAT GAATTTTTGT     1260

TCCCGTGAGA ACTTCTGGCT CTTGATCAAC TCCACGGATC CCGCAGGACA GCTCCAGTGG     1320

CTGGTGGGGG AGCTTCAGGC TGCTGAGGAT CGAGGAGACA AAGTGAGGGC CAGTAGTGGG     1380

AACACGGTGG TGCTGGGGGA CAAGCAGGCT CCTGTTGAGC TGGAGCACCT CTGGGCACAG     1440

AAGTTTTATT TTCCTGGCAT TCCCAACAAG TGTTCCCTGG GGATTCAGCT CATGGTCACT     1500

GTTGAAAGCC TTCATTCAGT CCCCCTTTCT CTAGCCAGGG CTGCCTGGAC CCCTGGATGC     1560

CCTGATTACC ATCCTTAATT CTCCCTACTA GGTGCATATA ATTGGCCACA TTCCCCCAGG     1620

GCACTGTCTG AAGAGCTGGA GCTGGAATTA TTACCGAATT GTGA                      1664
```

(2) INFORMATION FOR SEQ ID NO:4:

(i) SEQUENCE CHARACTERISTICS:
        (A) LENGTH: 4741 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:4:

```
TCGACAGCCG CCCGCCACCG AGAGATCAGC TGTCAGAGAT CAGAGGAAGA GGAAGGGGCG       60

GAGCTGCTTT GCGGCCGGCC GGAGCAGTCA GCCGACTACA GAGAAGGGTA ATCGGGTGTC      120

CCCGGCGCCG CCCGGGGCCC TGAGGGCTGG CTAGGGTCCA GGCCGGGGGG GACGGGACAG      180

ACGAACCAGC CCCGTGTAGG AAGCGCGACA ATGCCCCGCT ACGGAGCGTC ACTCCGCCAG      240

AGCTGCCCCA GGTCCGGCCG GGAGCAGGGA CAAGACGGGA CCGCCGGAGC CCCCGGACTC      300

CTTTGGATGG GCCTGGCGCT GGCGCTGGCG CTGGCGCTGG CGCTGGCTCT GTCTGACTCT      360

CGGGTTCTCT GGGCTCCGGC AGAGGCTCAC CCTCTTTCTC CCCAAGGCCA TCCTGCCAGG      420

TTACATCGCA TAGTGCCCCG GCTCCAGAGA TGTCTTTGGGT GGGGGAACCT CACCTGCCCA    480

ATCTGCAAAG GTCTATTCAC CGCCATCAAC CTCGGGCTGA AGGTGAGCAC TGAAGGGGCT      540

GCAGTGGAGG AGGCCGAAAG GAGTGCTGGG GCTGGGGGCT GGGGCTGATG CTGGTGCGCT      600

GGGCTCAGAA TGCATCCCTG ATGGAGAGGG TGGCATCTAC AATCCATCAC TGAGTTTGCT      660

CCCCTTTGGG GACACCCATG GCTACATGCC ACCATCACCC CATTGTGACC TTTGTGAAGT      720

AAGAAATAAT GCAGACAGTG CCTGAGGAAG TCAGCTTGCC AAGCAAAGGC CTCATGCCAC      780

AGGCCGCTGA GCTAAAGAAG AAGCGATGGC CTGGTGCTGC CTGAGTTACA GGCAATATC       840

TGGAAGGCAA AGGTGTGCAC TGAGCTTGGT GCACTGAGTC CTGCCCAGCC CCAGTTTGGA      900

AATGGAGGCC AAGGGGTGGT GGCCAGGGGT TGGCCTGGTT CCTCTGCTCT GCCTCTGATT      960

TCTCACCATG CGCTCCTCCC ACTGCAGAAG GAACCCAATG TGGCTCGCGT GGGCTCCGTG     1020

GCCATCAAGC TGTGCAATCT GCTGAAGATA GCACCACCTG CCGTGTGCCA ATCCATTGTC     1080

CACCTCTTTG AGGATGACAT GGTGGAGGTG TGGAGACGCT CAGTGCTGAG CCCATCTGAG     1140

GCCTGTGGCC TGCTCCTGGG CTCCACCTGT GGGCACTGGG ACATTTTCTC ATCTTGGAAC     1200
```

```
CGGACACCGG ACGAGGACCC GAGGTGGACA CCCGTGACCC TGTAAAAGAG TAGAACCTTG    1260

ATCTCTTTGC CTACTGTGCC GAAGCCGCCC CCCAAACCCC CTAGCCCCCC AGCCCCAGGT    1320

GCCCCTGTCA GCCGCATCCT CTTCCTCACT GACCTGCACT GGGATCATGA CTACCTGGAG    1380

GGCACGGACC CTGACTGTGC AGACCCACTG TGCTGCCGCC GGGGTTCTGG CCTGCCGCCC    1440

GCATCCCGGC CAGGTGCCGG ATACTGGGGC GAATACAGCA AGTGTGACCT GCCCCTGAGG    1500

ACCCTGGAGA GCCTGTTGAG TGGGCTGGGC CCAGCCGGCC CTTTTGATAT GGTGTACTGG    1560

ACAGGAGACA TCCCCGCACA TGATGTCTGG CACCAGACTC GTCAGGACCA ACTGCGGGCC    1620

CTGACCACCG TCACAGCACT TGTGAGGAAG TTCCTGGGGC CAGTGCCAGT GTACCCTGCT    1680

GTGGGTAACC ATGAAAGCAC ACCTGTCAAT AGCTTCCCTC CCCCCTTCAT TGAGGGCAAC    1740

CACTCCTCCC GCTGGCTCTA TGAAGCGATG GCCAAGGCTT GGGAGCCCTG GCTGCCTGCC    1800

GAAGCCCTGC GCACCCTCAG GTACTTATCG TCCGTGGAAA CCCAGGAAGG GAAAAGAAAG    1860

GTGAATGAAA GTGAAGGGAG AAGGGAACCT GGGGCATTGT CTCTGATTGC TCTAGCATGA    1920

GTCCTTAGTG CTCTTCATTT GGCTCCCCTA ATCTGACTCC TCCTTCCCTT TCTACTGTTT    1980

TGCCGCACCA GGCTTTTTTT TTTTTTTTTT TTTTAGTTTA GTTTTTGTAG AGACAAGATC    2040

TTGCTATGTT GCCCAGGCTG GTCTCAAACA CCTAACCTCA AGCAATCCTC CCGCCTCGGC    2100

CTCCCAAAAT GCTGGGACCA CAGGCATCAG CTACTGCTCC TGGCCCTCCC TTTTTTTTTT    2160

TTTTTTTTTT TTTTTTTTTT GAGATGGAAT CTTGCTCTGT TGCCCAGGCT GGAGTGCAGT    2220

GGCACCATCT CAGCTCACTA CAGCCTCCAC CTCCTGGGTT CAAGCAATTC TGCCTCAGCC    2280

TCCCAAGTAC CTGGGACTAC AGGTGCACGC CACCACACCC AGCTAATTTT TGTATTTTTA    2340

GTAGAGATGG GGTTTCACCA TGTTGGCCAA GATGGTCTTG ATCTCCTGAC CTCATGATCT    2400

GCCCACCTCG GCCTCCCAAA GTGCTGGGAT TACAGGCATG AACCACTGCA CCCAGCTTTC    2460

CAGCCCTCCC TTTCTACTCT TATCTCCAGC CACCCTCCTT CAAAGGTCTG GCAGCATAAC    2520

CTCTCTATGC CCCAGCTGTG TCTTTGCTCA TGTTGGCCCT CTGGAAATGA TTTCCCCCTT    2580

TTTTTTAAGT GCTCCAGTTT TTCCCACCTT ATCCATCCCA TGTCATCTTC CCTCTGTGTG    2640

GTCCTTGCTT CCCATTCTAG CTAACTCTTA TCCCTCCCCC ATACTCCTGG AGCCCTCTGC    2700

CCTCAGATGC TTTTGTGTCA CACAGACCCA ATAATTAGAA CTGTTTGGTC TCTGGCTAGA    2760

CTGTGAGCTC CTTGCAGGTG GGGAAGATGT CATGTATGCT TTTACCCTCC ACCCAAATGC    2820

CCAGCACAGG AGGACCAGGA TTGGAACAAG TGTTGACCTC TCATGTTTAC TTTGTTTCAG    2880

AATTGGGGGG TTCTATGCTC TTTCCCCATA CCCCGGTCTC CGCCTCATCT CTCTCAATAT    2940

GAATTTTTGT TCCCGTGAGA ACTTCTGGCT CTTGATCAAC TCCACGGATC CCGCAGGACA    3000

GCTCCAGTGG CTGGTGGGGG AGCTTCAGGC TGCTGAGGAT CGAGGAGACA AAGTGAGGGC    3060

CAGTAGTGGG AACACGGTGG TGCTGGGGGA CAAGCAGGCT CCTGTTGAGC TGGAGCACCT    3120

CTGGGCACAG AAGTTTTATT TTCCTGGCAT TCCCAACAAG TGTTCCCTGG GGATTCAGCT    3180

CATGGTCACT GTTGAAAGCC TTCATTCAGT CCCCCTTTCT CTAGCCAGGG CTGCCTGGAC    3240

CCCTGGATGC CCTGATTACC ATCCTTAATT CTCCCTACTA GGTGCATATA ATTGGCCACA    3300

TTCCCCCAGG GCACTGTCTG AAGAGCTGGA GCTGGAATTA TTACCGAATT GTAGCCAGGT    3360

AGGACGGAGA TGAGGGTGGG AATAGGGACA GGGTGAGTGT CTGAAGGCTG AAAATTCCCT    3420

TGAGCATCTC ACCATCCCTG TTGTCCCATG GAGTGGGGAG GCTCCTCACT AGAACAGGTT    3480

GGAGAAAGAG GGCATCCTAT CTCCCCAGAT GTCTTCCTAC CCCTCCCTAG AATCTTCTGA    3540
```

```
ATGTAGTACC TTCTGGCCAG GTATGAGAAC ACCCTGGCTG CTCAGTTCTT TGGCCACACT    3600

CATGTGGATG AATTTGAGGT CTTCTATGAT GAAGAGACTC TGAGCCGGCC GCTGGCTGTA    3660

GCCTTCCTGG CACCCAGTGC AACTACCTAC ATCGGCCTTA ATCCTGGTGA GTGAGGCAGA    3720

AGGGAGCCTC CCTTATCCTG GAGTTGGTGG GATAGGGGAA GGAGGTTGGA GCCAGAGCCT    3780

GCAAAGCATG GGCAGGATGT GTGGCCCCTC CCTGGAGTTA CCCTTGCTCC TTGCCCCTCC    3840

AGTCAGCCCC ACATCCTTGC AGGTTACCGT GTGTACCAAA TAGATGGAAA CTACTCCGGG    3900

AGCTCTCACG TGGTCCTGGA CCATGAGACC TACATCCTGA ATCTGACCCA GGCAAACATA    3960

CCGGGAGCCA TACCGCACTG GCAGCTTCTC TACAGGGCTC GAGAAACCTA TGGGCTGCCC    4020

AACACACTGC CTACCGCCTG GCACAACCTG GTATATCGCA TGCGGGGCGA CATGCAACTT    4080

TTCCAGACCT TCTGGTTTCT CTACCATAAG GGCCACCCAC CCTCGGAGCC CTGTGGCACG    4140

CCCTGCCGTC TGGCTACTCT TTGTGCCCAG CTCTCTGCCC GTGCTGACAG CCCTGCTCTG    4200

TGCCGCCACC TGATGCCAGA TGGGAGCCTC CCAGAGGCCC AGAGCCTGTG GCCAAGGCCA    4260

CTGTTTTGCT AGGGCCCCAG GGCCCACATT TGGGAAAGTT CTTGATGTAG GAAAGGGTGA    4320

AAAAGCCCAA ATGCTGCTGT GGTTCAACCA GGCAAGATCA TCCGGTGAAA GAACCAGTCC    4380

CTGGGCCCCA AGGATGCCGG GGAAACAGGA CCTTCTCCTT TCCTGGAGCT GGTTTAGCTG    4440

GATATGGGAG GGGGTTTGGC TGCCTGTGCC CAGGAGCTAG ACTGCCTTGA GGCTGCTGTC    4500

CTTTCACAGC CATGGAGTAG AGGCCTAAGT TGACACTGCC CTGGGCAGAC AAGACAGGAG    4560

CTGTCGCCCC AGGCCTGTGC TGCCCAGCCA GGAACCCTGT ACTGCTGCTG CGACCTGATG    4620

CTGCCAGTCT GTTAAAATAA AGATAAGAGA CTTGGACTCC AGACCCCTGT GTGACTGTCC    4680

CAATTTCTTC TTTTCCAGGCA AGCAGGGCAA GGAGATCTTT GGAGCAAGAT CATAACTGAG    4740

G                                                                     4741
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:5:

```
GGTTACCGTG TGTAC                                                        15
```

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:6:

```
GGTTACCTTG TGTAC                                                        15
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single

```
        (D) TOPOLOGY: unknown (ii) MOLECULE TYPE: DNA (genomic)

(ix) FEATURE:
        (A) NAME/KEY: CDS
        (B) LOCATION: 1..15

(xi) SEQUENCE DESCRIPTION: SEQ ID NO:7:

CTG TGC CGC CAC CTG                                                  15
Leu Cys Arg His Leu
 1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:8:

Leu Cys Arg His Leu
 1               5

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..12

(xi) SEQUENCE DESCRIPTION: SEQ ID NO:9:

CTG TGC CAC CTG                                                      12
Leu Cys His Leu
 1

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: unknown (ii) MOLECULE TYPE: protein (xi) SEQUENCE DESCRIPTION: SEQ ID NO:10:

Leu Cys His Leu
 1

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:11:

AGTAGTCTCG AGACGGGACA GACGAACCA                                      29
```

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:12:

AGTAGTCTGC AGAGCAGGGT ACATGGCACT G                                  31

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:13:

ATCATCAAGC TTGGGTAACC ATGAAAGCA                                    29

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:14:

ATCATCGAAT TCTACAATTC GGTAATAATT CC                                32

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:15:

CTCCACGGAT CCCGCAGGA                                                19

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:16:

AGTAGTGTCG ACTTGCCTGG TTGAACCACA GC                                32

(2) INFORMATION FOR SEQ ID NO:17:

(i) SEQUENCE CHARACTERISTICS:
    (A) LENGTH: 27 base pairs
    (B) TYPE: nucleic acid
    (C) STRANDEDNESS: single
    (D) TOPOLOGY: unknown (ii) MOLECULE TYPE: DNA (xi) SEQUENCE DESCRIPTION: SEQ ID NO:17:

AGTAGTCGAC ATGGGCAGGA TGTGTGG                              27

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:18:

CTATTTGGTA CACACGG                                         17

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:19:

CTATTTGGTA CACAAGG                                         17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:20:

CTCTGTGCCG CCACCTG                                         17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:21:

GCTCTGTGCC ACCTGAT                                         17

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single (D) TOPOLOGY: unknown (ii) MOLECULE TYPE: DNA (xi) SEQUENCE DESCRIPTION: SEQ ID NO:22:

ATCATTGAAT TCCACGGACG ATAAGTAC                                           28

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:23:

ATCATCCTCG AGACGGGACA GACGAACCA                                          29

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:24:

GTTCCTTCTT CAGCCCG                                                       17

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:25:

AGTAGTCGAC TGCTAGAGCA ATCAGAG                                            27

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:26:

AGTGTCGACT CGTCAGGACC AAC                                                23

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:27:

ATGAAGCAAT ACCTGTC                                                          17

(2) INFORMATION FOR SEQ ID NO:28:

(i) SEQUENCE CHARACTERISTICS:
       (A) LENGTH: 17 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:28:

ATGAAGCAAC ACCTGTC                                                          17

(2) INFORMATION FOR SEQ ID NO:29:

(i) SEQUENCE CHARACTERISTICS:
       (A) LENGTH: 17 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:29:

ACTACTCCAG GAGCTCT                                                          17

(2) INFORMATION FOR SEQ ID NO:30:

(i) SEQUENCE CHARACTERISTICS:
       (A) LENGTH: 17 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:30:

ACTACTCCGG GAGCTCT                                                          17

(2) INFORMATION FOR SEQ ID NO:31:

(i) SEQUENCE CHARACTERISTICS:
       (A) LENGTH: 28 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:31:

TCATCCTCGA GCACTGACCT GCACTGGG                                              28

(2) INFORMATION FOR SEQ ID NO:32:

(i) SEQUENCE CHARACTERISTICS:
       (A) LENGTH: 17 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:32:

GTCACAGCAC TTGTGAG                                                          17

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:33:

```
GTCACAGCAC CTGTGAG                                                    17
```

(2) INFORMATION FOR SEQ ID NO:34:

(i) SEQUENCE CHARACTERISTICS:
        (A) LENGTH: 2347 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: CDS
        (B) LOCATION: 88..1974

(xi) SEQUENCE DESCRIPTION: SEQ ID NO:34:

```
GGCGCCGCCC GGGGCCCTGA GGGCTGGCTA GGGTCCAGGC CGGGGGGGAC GGGACAGACG      60

AACCAGCCCC GTGTAGGAAG CGCGACA ATG CCC CGC TAC GGA GCG TCA CTC        111
                              Met Pro Arg Tyr Gly Ala Ser Leu
                                1               5

CGC CAG AGC TGC CCC AGG TCC GGC CGG GAG CAG GGA CAA GAC GGG ACC      159
Arg Gln Ser Cys Pro Arg Ser Gly Arg Glu Gln Gly Gln Asp Gly Thr
     10                  15                  20

GCC GGA GCC CCC GGA CTC CTT TGG ATG GGC CTG GTG CTG GCG CTG GCG      207
Ala Gly Ala Pro Gly Leu Leu Trp Met Gly Leu Val Leu Ala Leu Ala
 25                  30                  35                  40

CTG GCG CTG GCG CTG GCT CTG TCT GAC TCT CGG GTT CTC TGG GCT CCG      255
Leu Ala Leu Ala Leu Ala Leu Ser Asp Ser Arg Val Leu Trp Ala Pro
                 45                  50                  55

GCA GAG GCT CAC CCT CTT TCT CCC CAA GGC CAT CCT GCC AGG TTA CAT      303
Ala Glu Ala His Pro Leu Ser Pro Gln Gly His Pro Ala Arg Leu His
             60                  65                  70

CGC ATA GTG CCC CGG CTC CGA GAT GTC TTT GGG TGG GGG AAC CTC ACC      351
Arg Ile Val Pro Arg Leu Arg Asp Val Phe Gly Trp Gly Asn Leu Thr
         75                  80                  85

TGC CCA ATC TGC AAA GGT CTA TTC ACC GCC ATC AAC CTC GGG CTG AAG      399
Cys Pro Ile Cys Lys Gly Leu Phe Thr Ala Ile Asn Leu Gly Leu Lys
     90                  95                 100

AAG GAA CCC AAT GTG GCT CGC GTG GGC TCC GTG GCC ATC AAG CTG TGC      447
Lys Glu Pro Asn Val Ala Arg Val Gly Ser Val Ala Ile Lys Leu Cys
105                 110                 115                 120

AAT CTG CTG AAG ATA GCA CCA CCT GCC GTG TGC CAA TCC ATT GTC CAC      495
Asn Leu Leu Lys Ile Ala Pro Pro Ala Val Cys Gln Ser Ile Val His
                125                 130                 135

CTC TTT GAG GAT GAC ATG GTG GAG GTG TGG AGA CGC TCA GTG CTG AGC      543
Leu Phe Glu Asp Asp Met Val Glu Val Trp Arg Arg Ser Val Leu Ser
            140                 145                 150

CCA TCT GAG GCC TGT GGC CTG CTC CTG GGC TCC ACC TGT GGG CAC TGG      591
Pro Ser Glu Ala Cys Gly Leu Leu Leu Gly Ser Thr Cys Gly His Trp
        155                 160                 165

GAC ATT TTC TCA TCT TGG AAC ATC TCT TTG CCT ACT GTG CCG AAG CCG      639
```

```
Asp Ile Phe Ser Ser Trp Asn Ile Ser Leu Pro Thr Val Pro Lys Pro
    170                 175                 180

CCC CCC AAA CCC CCT AGC CCC CCA GCC CCA GGT GCC CCT GTC AGC CGC      687
Pro Pro Lys Pro Pro Ser Pro Pro Ala Pro Gly Ala Pro Val Ser Arg
185             190                 195                 200

ATC CTC TTC CTC ACT GAC CTG CAC TGG GAT CAT GAC TAC CTG GAG GGC      735
Ile Leu Phe Leu Thr Asp Leu His Trp Asp His Asp Tyr Leu Glu Gly
                    205                 210                 215

ACG GAC CCT GAC TGT GCA GAC CCA CTG TGC TGC CGC CGG GGT TCT GGC      783
Thr Asp Pro Asp Cys Ala Asp Pro Leu Cys Cys Arg Arg Gly Ser Gly
                220                 225                 230

CTG CCG CCC GCA TCC CGG CCA GGT GCC GGA TAC TGG GGC GAA TAC AGC      831
Leu Pro Pro Ala Ser Arg Pro Gly Ala Gly Tyr Trp Gly Glu Tyr Ser
            235                 240                 245

AAG TGT GAC CTG CCC CTG AGG ACC CTG GAG AGC CTG TTG AGT GGG CTG      879
Lys Cys Asp Leu Pro Leu Arg Thr Leu Glu Ser Leu Leu Ser Gly Leu
        250                 255                 260

GGC CCA GCC GGC CCT TTT GAT ATG GTG TAC TGG ACA GGA GAC ATC CCC      927
Gly Pro Ala Gly Pro Phe Asp Met Val Tyr Trp Thr Gly Asp Ile Pro
265             270                 275                 280

GCA CAT GAT GTC TGG CAC CAG ACT CGT CAG GAC CAA CTG CGG GCC CTG      975
Ala His Asp Val Trp His Gln Thr Arg Gln Asp Gln Leu Arg Ala Leu
                    285                 290                 295

ACC ACC GTC ACA GCA CTT GTG AGG AAG TTC CTG GGG CCA GTG CCA GTG     1023
Thr Thr Val Thr Ala Leu Val Arg Lys Phe Leu Gly Pro Val Pro Val
                300                 305                 310

TAC CCT GCT GTG GGT AAC CAT GAA AGC ATA CCT GTC AAT AGC TTC CCT     1071
Tyr Pro Ala Val Gly Asn His Glu Ser Ile Pro Val Asn Ser Phe Pro
            315                 320                 325

CCC CCC TTC ATT GAG GGC AAC CAC TCC TCC CGC TGG CTC TAT GAA GCG     1119
Pro Pro Phe Ile Glu Gly Asn His Ser Ser Arg Trp Leu Tyr Glu Ala
        330                 335                 340

ATG GCC AAG GCT TGG GAG CCC TGG CTG CCT GCC GAA GCC CTG CGC ACC     1167
Met Ala Lys Ala Trp Glu Pro Trp Leu Pro Ala Glu Ala Leu Arg Thr
345             350                 355                 360

CTC AGA ATT GGG GGG TTC TAT GCT CTT TCC CCA TAC CCC GGT CTC CGC     1215
Leu Arg Ile Gly Gly Phe Tyr Ala Leu Ser Pro Tyr Pro Gly Leu Arg
                    365                 370                 375

CTC ATC TCT CTC AAT ATG AAT TTT TGT TCC CGT GAG AAC TTC TGG CTC     1263
Leu Ile Ser Leu Asn Met Asn Phe Cys Ser Arg Glu Asn Phe Trp Leu
                380                 385                 390

TTG ATC AAC TCC ACG GAT CCC GCA GGA CAG CTC CAG TGG CTG GTG GGG     1311
Leu Ile Asn Ser Thr Asp Pro Ala Gly Gln Leu Gln Trp Leu Val Gly
            395                 400                 405

GAG CTT CAG GCT GCT GAG GAT CGA GGA GAC AAA GTG CAT ATA ATT GGC     1359
Glu Leu Gln Ala Ala Glu Asp Arg Gly Asp Lys Val His Ile Ile Gly
        410                 415                 420

CAC ATT CCC CCA GGG CAC TGT CTG AAG AGC TGG AGC TGG AAT TAT TAC     1407
His Ile Pro Pro Gly His Cys Leu Lys Ser Trp Ser Trp Asn Tyr Tyr
425             430                 435                 440

CGA ATT GTA GCC AGG TAT GAG AAC ACC CTG GCT GCT CAG TTC TTT GGC     1455
Arg Ile Val Ala Arg Tyr Glu Asn Thr Leu Ala Ala Gln Phe Phe Gly
                    445                 450                 455

CAC ACT CAT GTG GAT GAA TTT GAG GTC TTC TAT GAT GAA GAG ACT CTG     1503
His Thr His Val Asp Glu Phe Glu Val Phe Tyr Asp Glu Glu Thr Leu
                460                 465                 470

AGC CGG CCG CTG GCT GTA GCC TTC CTG GCA CCC AGT GCA ACT ACC TAC     1551
Ser Arg Pro Leu Ala Val Ala Phe Leu Ala Pro Ser Ala Thr Thr Tyr
            475                 480                 485
```

-continued

```
ATC GGC CTT AAT CCT GGT TAC CTT GTG TAC CAA ATA GAT GGA AAC TAC      1599
Ile Gly Leu Asn Pro Gly Tyr Leu Val Tyr Gln Ile Asp Gly Asn Tyr
        490                 495                 500

TCC AGG AGC TCT CAC GTG GTC CTG GAC CAT GAG ACC TAC ATC CTG AAT      1647
Ser Arg Ser Ser His Val Val Leu Asp His Glu Thr Tyr Ile Leu Asn
505                 510                 515                 520

CTG ACC CAG GCA AAC ATA CCG GGA GCC ATA CCG CAC TGG CAG CTT CTC      1695
Leu Thr Gln Ala Asn Ile Pro Gly Ala Ile Pro His Trp Gln Leu Leu
                525                 530                 535

TAC AGG GCT CGA GAA ACC TAT GGG CTG CCC AAC ACA CTG CCT ACC GCC      1743
Tyr Arg Ala Arg Glu Thr Tyr Gly Leu Pro Asn Thr Leu Pro Thr Ala
            540                 545                 550

TGG CAC AAC CTG GTA TAT CGC ATG CGG GGC GAC ATG CAA CTT TTC CAG      1791
Trp His Asn Leu Val Tyr Arg Met Arg Gly Asp Met Gln Leu Phe Gln
        555                 560                 565

ACC TTC TGG TTT CTC TAC CAT AAG GGC CAC CCA CCC TCG GAG CCC TGT      1839
Thr Phe Trp Phe Leu Tyr His Lys Gly His Pro Pro Ser Glu Pro Cys
570                 575                 580

GGC ACG CCC TGC CGT CTG GCT ACT CTT TGT GCC CAG CTC TCT GCC CGT      1887
Gly Thr Pro Cys Arg Leu Ala Thr Leu Cys Ala Gln Leu Ser Ala Arg
585                 590                 595                 600

GCT GAC AGC CCT GCT CTG TGC CGC CAC CTG ATG CCA GAT GGG AGC CTC      1935
Ala Asp Ser Pro Ala Leu Cys Arg His Leu Met Pro Asp Gly Ser Leu
                605                 610                 615

CCA GAG GCC CAG AGC CTG TGG CCA AGG CCA CTG TTT TGC TAGGGCCCCA       1984
Pro Glu Ala Gln Ser Leu Trp Pro Arg Pro Leu Phe Cys
            620                 625

GGGCCCACAT TTGGGAAAGT TCTTGATGTA GGAAAGGGTG AAAAAGCCCA AATGCTGCTG    2044

TGGTTCAACC AGGCAAGATC ATCCGGTGAA AGAACCAGTC CCTGGGCCCC AAGGATGCCG    2104

GGGAAACAGG ACCTTCTCCT TTCCTGGAGC TGGTTTAGCT GGATATGGGA GGGGGTTTGG    2164

CTGCCTGTGC CCAGGAGCTA GACTGCCTTG AGGCTGCTGT CCTTTCACAG CCATGGAGTA    2224

GAGGCCTAAG TTGACACTGC CCTGGGCAGA CAAGACAGGA GCTGTCGCCC CAGGCCTGTG    2284

CTGCCCAGCC AGGAACCCTG TACTGCTGCT GCGACCTGAT GCTGCCAGTC TGTTAAAATA    2344

AAG                                                                  2347

(2) INFORMATION FOR SEQ ID NO:35:

(i) SEQUENCE CHARACTERISTICS:
        (A) LENGTH: 2344 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: CDS
        (B) LOCATION: 88..1971

(xi) SEQUENCE DESCRIPTION: SEQ ID NO:35:

GGCGCCGCCC GGGGCCCTGA GGGCTGGCTA GGGTCCAGGC CGGGGGGGAC GGGACAGACG      60

AACCAGCCCC GTGTAGGAAG CGCGACA ATG CCC CGC TAC GGA GCG TCA CTC         111
                                Met Pro Arg Tyr Gly Ala Ser Leu
                                  1               5

CGC CAG AGC TGC CCC AGG TCC GGC CGG GAG CAG GGA CAA GAC GGG ACC       159
Arg Gln Ser Cys Pro Arg Ser Gly Arg Glu Gln Gly Gln Asp Gly Thr
         10                  15                  20

GCC GGA GCC CCC GGA CTC CTT TGG ATG GGC CTG GTG CTG GCG CTG GCG       207
Ala Gly Ala Pro Gly Leu Leu Trp Met Gly Leu Val Leu Ala Leu Ala
```

```
                25                    30                    35                      40
CTG GCG CTG GCG CTG GCT CTG TCT GAC TCT CGG GTT CTC TGG GCT CCG           255
Leu Ala Leu Ala Leu Ala Leu Ser Asp Ser Arg Val Leu Trp Ala Pro
                        45                    50                    55

GCA GAG GCT CAC CCT CTT TCT CCC CAA GGC CAT CCT GCC AGG TTA CAT           303
Ala Glu Ala His Pro Leu Ser Pro Gln Gly His Pro Ala Arg Leu His
                60                    65                    70

CGC ATA GTG CCC CGG CTC CGA GAT GTC TTT GGG TGG GGG AAC CTC ACC           351
Arg Ile Val Pro Arg Leu Arg Asp Val Phe Gly Trp Gly Asn Leu Thr
            75                    80                    85

TGC CCA ATC TGC AAA GGT CTA TTC ACC GCC ATC AAC CTC GGG CTG AAG           399
Cys Pro Ile Cys Lys Gly Leu Phe Thr Ala Ile Asn Leu Gly Leu Lys
        90                    95                   100

AAG GAA CCC AAT GTG GCT CGC GTG GGC TCC GTG GCC ATC AAG CTG TGC           447
Lys Glu Pro Asn Val Ala Arg Val Gly Ser Val Ala Ile Lys Leu Cys
105                   110                   115                   120

AAT CTG CTG AAG ATA GCA CCA CCT GCC GTG TGC CAA TCC ATT GTC CAC           495
Asn Leu Leu Lys Ile Ala Pro Pro Ala Val Cys Gln Ser Ile Val His
                125                   130                   135

CTC TTT GAG GAT GAC ATG GTG GAG GTG TGG AGA CGC TCA GTG CTG AGC           543
Leu Phe Glu Asp Asp Met Val Glu Val Trp Arg Arg Ser Val Leu Ser
            140                   145                   150

CCA TCT GAG GCC TGT GGC CTG CTC CTG GGC TCC ACC TGT GGG CAC TGG           591
Pro Ser Glu Ala Cys Gly Leu Leu Leu Gly Ser Thr Cys Gly His Trp
        155                   160                   165

GAC ATT TTC TCA TCT TGG AAC ATC TCT TTG CCT ACT GTG CCG AAG CCG           639
Asp Ile Phe Ser Ser Trp Asn Ile Ser Leu Pro Thr Val Pro Lys Pro
170                   175                   180

CCC CCC AAA CCC CCT AGC CCC CCA GCC CCA GGT GCC CCT GTC AGC CGC           687
Pro Pro Lys Pro Pro Ser Pro Pro Ala Pro Gly Ala Pro Val Ser Arg
185                   190                   195                   200

ATC CTC TTC CTC ACT GAC CTG CAC TGG GAT CAT GAC TAC CTG GAG GGC           735
Ile Leu Phe Leu Thr Asp Leu His Trp Asp His Asp Tyr Leu Glu Gly
                205                   210                   215

ACG GAC CCT GAC TGT GCA GAC CCA CTG TGC TGC CGC CGG GGT TCT GGC           783
Thr Asp Pro Asp Cys Ala Asp Pro Leu Cys Cys Arg Arg Gly Ser Gly
            220                   225                   230

CTG CCG CCC GCA TCC CGG CCA GGT GCC GGA TAC TGG GGC GAA TAC AGC           831
Leu Pro Pro Ala Ser Arg Pro Gly Ala Gly Tyr Trp Gly Glu Tyr Ser
        235                   240                   245

AAG TGT GAC CTG CCC CTG AGG ACC CTG GAG AGC CTG TTG AGT GGG CTG           879
Lys Cys Asp Leu Pro Leu Arg Thr Leu Glu Ser Leu Leu Ser Gly Leu
250                   255                   260

GGC CCA GCC GGC CCT TTT GAT ATG GTG TAC TGG ACA GGA GAC ATC CCC           927
Gly Pro Ala Gly Pro Phe Asp Met Val Tyr Trp Thr Gly Asp Ile Pro
265                   270                   275                   280

GCA CAT GAT GTC TGG CAC CAG ACT CGT CAG GAC CAA CTG CGG GCC CTG           975
Ala His Asp Val Trp His Gln Thr Arg Gln Asp Gln Leu Arg Ala Leu
                285                   290                   295

ACC ACC GTC ACA GCA CTT GTG AGG AAG TTC CTG GGG CCA GTG CCA GTG          1023
Thr Thr Val Thr Ala Leu Val Arg Lys Phe Leu Gly Pro Val Pro Val
            300                   305                   310

TAC CCT GCT GTG GGT AAC CAT GAA AGC ATA CCT GTC AAT AGC TTC CCT          1071
Tyr Pro Ala Val Gly Asn His Glu Ser Ile Pro Val Asn Ser Phe Pro
        315                   320                   325

CCC CCC TTC ATT GAG GGC AAC CAC TCC TCC CGC TGG CTC TAT GAA GCG          1119
Pro Pro Phe Ile Glu Gly Asn His Ser Ser Arg Trp Leu Tyr Glu Ala
330                   335                   340

ATG GCC AAG GCT TGG GAG CCC TGG CTG CCT GCC GAA GCC CTG CGC ACC          1167
```

```
                                                                     -continued Met Ala Lys Ala Trp Glu Pro Trp Leu Pro Ala Glu Ala Leu Arg Thr
345                 350                 355                 360

CTC AGA ATT GGG GGG TTC TAT GCT CTT TCC CCA TAC CCC GGT CTC CGC    1215
Leu Arg Ile Gly Gly Phe Tyr Ala Leu Ser Pro Tyr Pro Gly Leu Arg
            365                 370                 375

CTC ATC TCT CTC AAT ATG AAT TTT TGT TCC CGT GAG AAC TTC TGG CTC    1263
Leu Ile Ser Leu Asn Met Asn Phe Cys Ser Arg Glu Asn Phe Trp Leu
                380                 385                 390

TTG ATC AAC TCC ACG GAT CCC GCA GGA CAG CTC CAG TGG CTG GTG GGG    1311
Leu Ile Asn Ser Thr Asp Pro Ala Gly Gln Leu Gln Trp Leu Val Gly
            395                 400                 405

GAG CTT CAG GCT GCT GAG GAT CGA GGA GAC AAA GTG CAT ATA ATT GGC    1359
Glu Leu Gln Ala Ala Glu Asp Arg Gly Asp Lys Val His Ile Ile Gly
        410                 415                 420

CAC ATT CCC CCA GGG CAC TGT CTG AAG AGC TGG AGC TGG AAT TAT TAC    1407
His Ile Pro Pro Gly His Cys Leu Lys Ser Trp Ser Trp Asn Tyr Tyr
425                 430                 435                 440

CGA ATT GTA GCC AGG TAT GAG AAC ACC CTG GCT GCT CAG TTC TTT GGC    1455
Arg Ile Val Ala Arg Tyr Glu Asn Thr Leu Ala Ala Gln Phe Phe Gly
            445                 450                 455

CAC ACT CAT GTG GAT GAA TTT GAG GTC TTC TAT GAT GAA GAG ACT CTG    1503
His Thr His Val Asp Glu Phe Glu Val Phe Tyr Asp Glu Glu Thr Leu
                460                 465                 470

AGC CGG CCG CTG GCT GTA GCC TTC CTG GCA CCC AGT GCA ACT ACC TAC    1551
Ser Arg Pro Leu Ala Val Ala Phe Leu Ala Pro Ser Ala Thr Thr Tyr
            475                 480                 485

ATC GGC CTT AAT CCT GGT TAC CGT GTG TAC CAA ATA GAT GGA AAC TAC    1599
Ile Gly Leu Asn Pro Gly Tyr Arg Val Tyr Gln Ile Asp Gly Asn Tyr
490                 495                 500

TCC AGG AGC TCT CAC GTG GTC CTG GAC CAT GAG ACC TAC ATC CTG AAT    1647
Ser Arg Ser Ser His Val Val Leu Asp His Glu Thr Tyr Ile Leu Asn
505                 510                 515                 520

CTG ACC CAG GCA AAC ATA CCG GGA GCC ATA CCG CAC TGG CAG CTT CTC    1695
Leu Thr Gln Ala Asn Ile Pro Gly Ala Ile Pro His Trp Gln Leu Leu
                525                 530                 535

TAC AGG GCT CGA GAA ACC TAT GGG CTG CCC AAC ACA CTG CCT ACC GCC    1743
Tyr Arg Ala Arg Glu Thr Tyr Gly Leu Pro Asn Thr Leu Pro Thr Ala
            540                 545                 550

TGG CAC AAC CTG GTA TAT CGC ATG CGG GGC GAC ATG CAA CTT TTC CAG    1791
Trp His Asn Leu Val Tyr Arg Met Arg Gly Asp Met Gln Leu Phe Gln
        555                 560                 565

ACC TTC TGG TTT CTC TAC CAT AAG GGC CAC CCA CCC TCG GAG CCC TGT    1839
Thr Phe Trp Phe Leu Tyr His Lys Gly His Pro Pro Ser Glu Pro Cys
570                 575                 580

GGC ACG CCC TGC CGT CTG GCT ACT CTT TGT GCC CAG CTC TCT GCC CGT    1887
Gly Thr Pro Cys Arg Leu Ala Thr Leu Cys Ala Gln Leu Ser Ala Arg
585                 590                 595                 600

GCT GAC AGC CCT GCT CTG TGC CAC CTG ATG CCA GAT GGG AGC CTC CCA    1935
Ala Asp Ser Pro Ala Leu Cys His Leu Met Pro Asp Gly Ser Leu Pro
                605                 610                 615

GAG GCC CAG AGC CTG TGG CCA AGG CCA CTG TTT TGC TAGGGCCCCA         1981
Glu Ala Gln Ser Leu Trp Pro Arg Pro Leu Phe Cys
            620                 625

GGGCCCACAT TTGGGAAAGT TCTTGATGTA GGAAAGGGTG AAAAAGCCCA AATGCTGCTG  2041

TGGTTCAACC AGGCAAGATC ATCCGGTGAA AGAACCAGTC CCTGGGCCCC AAGGATGCCG  2101

GGGAAACAGG ACCTTCTCCT TTCCTGGAGC TGGTTTAGCT GGATATGGGA GGGGGTTTGG  2161

CTGCCTGTGC CCAGGAGCTA GACTGCCTTG AGGCTGCTGT CCTTTCACAG CCATGGAGTA  2221
```

```
GAGGCCTAAG TTGACACTGC CCTGGGCAGA CAAGACAGGA GCTGTCGCCC CAGGCCTGTG    2281

CTGCCCAGCC AGGAACCCTG TACTGCTGCT GCGACCTGAT GCTGCCAGTC TGTTAAAATA    2341

AAG                                                                  2344
```

(2) INFORMATION FOR SEQ ID NO:36:

(i) SEQUENCE CHARACTERISTICS:
        (A) LENGTH: 2347 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: CDS
        (B) LOCATION: 88..1974

(xi) SEQUENCE DESCRIPTION: SEQ ID NO:36:

```
GGCGCCGCCC GGGGCCCTGA GGGCTGGCTA GGGTCCAGGC CGGGGGGGAC GGGACAGACG     60

AACCAGCCCC GTGTAGGAAG CGCGACA ATG CCC CGC TAC GGA GCG TCA CTC        111
                              Met Pro Arg Tyr Gly Ala Ser Leu
                                1               5

CGC CAG AGC TGC CCC AGG TCC GGC CGG GAG CAG GGA CAA GAC GGG ACC      159
Arg Gln Ser Cys Pro Arg Ser Gly Arg Glu Gln Gly Gln Asp Gly Thr
 10              15                  20

GCC GGA GCC CCC GGA CTC CTT TGG ATG GGC CTG GTG CTG GCG CTG GCG      207
Ala Gly Ala Pro Gly Leu Leu Trp Met Gly Leu Val Leu Ala Leu Ala
 25              30                  35                      40

CTG GCG CTG GCG CTG GCT CTG TCT GAC TCT CGG GTT CTC TGG GCT CCG      255
Leu Ala Leu Ala Leu Ala Leu Ser Asp Ser Arg Val Leu Trp Ala Pro
                 45                  50                  55

GCA GAG GCT CAC CCT CTT TCT CCC CAA GGC CAT CCT GCC AGG TTA CAT      303
Ala Glu Ala His Pro Leu Ser Pro Gln Gly His Pro Ala Arg Leu His
             60                  65                  70

CGC ATA GTG CCC CGG CTC CGA GAT GTC TTT GGG TGG GGG AAC CTC ACC      351
Arg Ile Val Pro Arg Leu Arg Asp Val Phe Gly Trp Gly Asn Leu Thr
         75                  80                  85

TGC CCA ATC TGC AAA GGT CTA TTC ACC GCC ATC AAC CTC GGG CTG AAG      399
Cys Pro Ile Cys Lys Gly Leu Phe Thr Ala Ile Asn Leu Gly Leu Lys
     90                  95                 100

AAG GAA CCC AAT GTG GCT CGC GTG GGC TCC GTG GCC ATC AAG CTG TGC      447
Lys Glu Pro Asn Val Ala Arg Val Gly Ser Val Ala Ile Lys Leu Cys
105                 110                 115                 120

AAT CTG CTG AAG ATA GCA CCA CCT GCC GTG TGC CAA TCC ATT GTC CAC      495
Asn Leu Leu Lys Ile Ala Pro Pro Ala Val Cys Gln Ser Ile Val His
                125                 130                 135

CTC TTT GAG GAT GAC ATG GTG GAG GTG TGG AGA CGC TCA GTG CTG AGC      543
Leu Phe Glu Asp Asp Met Val Glu Val Trp Arg Arg Ser Val Leu Ser
                140                 145                 150

CCA TCT GAG GCC TGT GGC CTG CTC CTG GGC TCC ACC TGT GGG CAC TGG      591
Pro Ser Glu Ala Cys Gly Leu Leu Leu Gly Ser Thr Cys Gly His Trp
            155                 160                 165

GAC ATT TTC TCA TCT TGG AAC ATC TCT TTG CCT ACT GTG CCG AAG CCG      639
Asp Ile Phe Ser Ser Trp Asn Ile Ser Leu Pro Thr Val Pro Lys Pro
        170                 175                 180

CCC CCC AAA CCC CCT AGC CCC CCA GCC CCA GGT GCC CCT GTC AGC CGC      687
Pro Pro Lys Pro Pro Ser Pro Pro Ala Pro Gly Ala Pro Val Ser Arg
185                 190                 195                 200

ATC CTC TTC CTC ACT GAC CTG CAC TGG GAT CAT GAC TAC CTG GAG GGC      735
Ile Leu Phe Leu Thr Asp Leu His Trp Asp His Asp Tyr Leu Glu Gly
```

```
                    205                 210                 215
ACG GAC CCT GAC TGT GCA GAC CCA CTG TGC TGC CGC CGG GGT TCT GGC        783
Thr Asp Pro Asp Cys Ala Asp Pro Leu Cys Cys Arg Arg Gly Ser Gly
                220                 225                 230

CTG CCG CCC GCA TCC CGG CCA GGT GCC GGA TAC TGG GGC GAA TAC AGC        831
Leu Pro Pro Ala Ser Arg Pro Gly Ala Gly Tyr Trp Gly Glu Tyr Ser
        235                 240                 245

AAG TGT GAC CTG CCC CTG AGG ACC CTG GAG AGC CTG TTG AGT GGG CTG        879
Lys Cys Asp Leu Pro Leu Arg Thr Leu Glu Ser Leu Leu Ser Gly Leu
    250                 255                 260

GGC CCA GCC GGC CCT TTT GAT ATG GTG TAC TGG ACA GGA GAC ATC CCC        927
Gly Pro Ala Gly Pro Phe Asp Met Val Tyr Trp Thr Gly Asp Ile Pro
265                 270                 275                 280

GCA CAT GAT GTC TGG CAC CAG ACT CGT CAG GAC CAA CTG CGG GCC CTG        975
Ala His Asp Val Trp His Gln Thr Arg Gln Asp Gln Leu Arg Ala Leu
                285                 290                 295

ACC ACC GTC ACA GCA CCT GTG AGG AAG TTC CTG GGG CCA GTG CCA GTG       1023
Thr Thr Val Thr Ala Pro Val Arg Lys Phe Leu Gly Pro Val Pro Val
        300                 305                 310

TAC CCT GCT GTG GGT AAC CAT GAA AGC ATA CCT GTC AAT AGC TTC CCT       1071
Tyr Pro Ala Val Gly Asn His Glu Ser Ile Pro Val Asn Ser Phe Pro
    315                 320                 325

CCC CCC TTC ATT GAG GGC AAC CAC TCC TCC CGC TGG CTC TAT GAA GCG       1119
Pro Pro Phe Ile Glu Gly Asn His Ser Ser Arg Trp Leu Tyr Glu Ala
330                 335                 340

ATG GCC AAG GCT TGG GAG CCC TGG CTG CCT GCC GAA GCC CTG CGC ACC       1167
Met Ala Lys Ala Trp Glu Pro Trp Leu Pro Ala Glu Ala Leu Arg Thr
345                 350                 355                 360

CTC AGA ATT GGG GGG TTC TAT GCT CTT TCC CCA TAC CCC GGT CTC CGC       1215
Leu Arg Ile Gly Gly Phe Tyr Ala Leu Ser Pro Tyr Pro Gly Leu Arg
                365                 370                 375

CTC ATC TCT CTC AAT ATG AAT TTT TGT TCC CGT GAG AAC TTC TGG CTC       1263
Leu Ile Ser Leu Asn Met Asn Phe Cys Ser Arg Glu Asn Phe Trp Leu
        380                 385                 390

TTG ATC AAC TCC ACG GAT CCC GCA GGA CAG CTC CAG TGG CTG GTG GGG       1311
Leu Ile Asn Ser Thr Asp Pro Ala Gly Gln Leu Gln Trp Leu Val Gly
    395                 400                 405

GAG CTT CAG GCT GCT GAG GAT CGA GGA GAC AAA GTG CAT ATA ATT GGC       1359
Glu Leu Gln Ala Ala Glu Asp Arg Gly Asp Lys Val His Ile Ile Gly
410                 415                 420

CAC ATT CCC CCA GGG CAC TGT CTG AAG AGC TGG AGC TGG AAT TAT TAC       1407
His Ile Pro Pro Gly His Cys Leu Lys Ser Trp Ser Trp Asn Tyr Tyr
425                 430                 435                 440

CGA ATT GTA GCC AGG TAT GAG AAC ACC CTG GCT GCT CAG TTC TTT GGC       1455
Arg Ile Val Ala Arg Tyr Glu Asn Thr Leu Ala Ala Gln Phe Phe Gly
                445                 450                 455

CAC ACT CAT GTG GAT GAA TTT GAG GTC TTC TAT GAT GAA GAG ACT CTG       1503
His Thr His Val Asp Glu Phe Glu Val Phe Tyr Asp Glu Glu Thr Leu
        460                 465                 470

AGC CGG CCG CTG GCT GTA GCC TTC CTG GCA CCC AGT GCA ACT ACC TAC       1551
Ser Arg Pro Leu Ala Val Ala Phe Leu Ala Pro Ser Ala Thr Thr Tyr
    475                 480                 485

ATC GGC CTT AAT CCT GGT TAC CGT GTG TAC CAA ATA GAT GGA AAC TAC       1599
Ile Gly Leu Asn Pro Gly Tyr Arg Val Tyr Gln Ile Asp Gly Asn Tyr
490                 495                 500

TCC AGG AGC TCT CAC GTG GTC CTG GAC CAT GAG ACC TAC ATC CTG AAT       1647
Ser Arg Ser Ser His Val Val Leu Asp His Glu Thr Tyr Ile Leu Asn
505                 510                 515                 520

CTG ACC CAG GCA AAC ATA CCG GGA GCC ATA CCG CAC TGG CAG CTT CTC       1695
Leu Thr Gln Ala Asn Ile Pro Gly Ala Ile Pro His Trp Gln Leu Leu
```

-continued

```
Leu Thr Gln Ala Asn Ile Pro Gly Ala Ile Pro His Trp Gln Leu Leu
            525                 530                 535

TAC AGG GCT CGA GAA ACC TAT GGG CTG CCC AAC ACA CTG CCT ACC GCC      1743
Tyr Arg Ala Arg Glu Thr Tyr Gly Leu Pro Asn Thr Leu Pro Thr Ala
            540                 545                 550

TGG CAC AAC CTG GTA TAT CGC ATG CGG GGC GAC ATG CAA CTT TTC CAG      1791
Trp His Asn Leu Val Tyr Arg Met Arg Gly Asp Met Gln Leu Phe Gln
        555                 560                 565

ACC TTC TGG TTT CTC TAC CAT AAG GGC CAC CCA CCC TCG GAG CCC TGT      1839
Thr Phe Trp Phe Leu Tyr His Lys Gly His Pro Pro Ser Glu Pro Cys
        570                 575                 580

GGC ACG CCC TGC CGT CTG GCT ACT CTT TGT GCC CAG CTC TCT GCC CGT      1887
Gly Thr Pro Cys Arg Leu Ala Thr Leu Cys Ala Gln Leu Ser Ala Arg
585                 590                 595                 600

GCT GAC AGC CCT GCT CTG TGC CGC CAC CTG ATG CCA GAT GGG AGC CTC      1935
Ala Asp Ser Pro Ala Leu Cys Arg His Leu Met Pro Asp Gly Ser Leu
            605                 610                 615

CCA GAG GCC CAG AGC CTG TGG CCA AGG CCA CTG TTT TGC TAGGGCCCCA       1984
Pro Glu Ala Gln Ser Leu Trp Pro Arg Pro Leu Phe Cys
            620                 625

GGGCCCACAT TTGGGAAAGT TCTTGATGTA GGAAAGGGTG AAAAAGCCCA AATGCTGCTG    2044

TGGTTCAACC AGGCAAGATC ATCCGGTGAA AGAACCAGTC CCTGGGCCCC AAGGATGCCG    2104

GGGAAACAGG ACCTTCTCCT TTCCTGGAGC TGGTTTAGCT GGATATGGGA GGGGGTTTGG    2164

CTGCCTGTGC CCAGGAGCTA GACTGCCTTG AGGCTGCTGT CCTTTCACAG CCATGGAGTA    2224

GAGGCCTAAG TTGACACTGC CCTGGGCAGA CAAGACAGGA GCTGTCGCCC CAGGCCTGTG    2284

CTGCCCAGCC AGGAACCCTG TACTGCTGCT GCGACCTGAT GCTGCCAGTC TGTTAAAATA    2344

AAG                                                                  2347
```

ACID SPHINGOMYELINASE PROTEIN AND METHODS OF TREATING TYPE B NIEMANN-PICK DISEASE

1. INTRODUCTION

The present invention relates to the acid sphingomyelinase gene and to methods of diagnosing Niemann-Pick disease. It is based, at least in part, on the cloning and expression of the full-length cDNA encoding acid sphingomyelinase, the cloning and characterization of the genomic structure of the acid sphingomyelinase gene, and on the discovery of a frequent missense mutation in the acid sphingomyelinase gene of Ashkenazi Jewish Niemann-Pick disease patients.

2. BACKGROUND OF THE INVENTION

Types A and B Niemann-Pick disease (NPD) are autosomal recessive disorders resulting from the deficient activity of the lysosomal hydrolase, acid sphingomyelinase (ASM; sphingomyelin cholinephosphohydrolase, E:C 3.1.3.12) and the accumulation of sphingomyelin, primarily in reticuloendothelial lysosomes (Niemann, 1914, Fahrb. Kinderheikd, 79:1–6; Brady et al., 1966, Proc. Natl. Acad. Sci. U.S.A. 55;366–369; Fredrickson, 1966, in "The Metabolic Basis of Inherited Disease; Stanbury et al., eds., 2nd Ed., McGraw-Hill, New York, pp. 586–602; Spence and Callahan, 1989, in "The Metabolic Basis of Inherited Disease," Scriver et al., eds., 8th Ed., McGraw-Hill, New York, pp. 1655–1676). Type A disease is a rapidly progressive neurodegenerative disease of infancy manifested by failure to thrive, severe psychomotor retardation, hepatosplenomegaly, and demise by 2–3 years of age. In comparison, type B disease is characterized primarily by reticuloendothelial system sphingomyelin deposition leading to hepatosplenomegaly and pulmonary involvement, the absence of neurologic manifestations, and survival into adulthood. The nature of the biochemical and molecular defects that underlie the remarkable clinical heterogeneity of the A and B subtypes remains unknown. Although patients with both subtypes have residual ASM activity (about 1 to 10% of normal), biochemical analysis cannot reliably distinguish the two phenotypes. Moreover, the clinical course of Type B NPD is highly variable, and it is not presently possible to correlate disease severity with the level of residual ASM activity.

Types A and B NPD occur at least 10 times more frequently among individuals of Ashkenazi Jewish ancestry than in the general population. It is estimated that the incidence of the type A disease among Ashkenazi Jews is about 1 in 40,000, a gene frequency (q) of about 1 in 200, and a heterozygote frequency (2 pq) of 1 in 100 (Goodman, 1979, in "Genetic Disorders Among The Jewish People", John Hopkins Univ. Press, Baltimore, pp. 96–100). The incidence of type B NPD in the Ashkenazi Jewish population is less frequent, perhaps 1 in 80 (Goodman, supra). Thus, the combined heterozygotic frequency for types A and B NPD has been estimated to be about 1 in 70 among individuals of Ashkenazi Jewish decent. Although the enzymatic diagnosis of affected patients with either type A or B NPD can be made reliably (Spence and Callahan, supra), the enzymatic detection of obligate heterozygotes has proven problematic, particularly using peripheral leukocytes as the enzyme source. Presumably, the occurrence of neutral sphingomyelinases in some sources and/or the presence of residual ASM activity resulting from the mutant allele have contributed to the inability to reliably discriminate carriers for either disease subtype. Even the use of cultured skin fibroblasts, which do not express the neutral sphingomyelinase, has not provided unambiguous results with obligate heterozygotes.

Recently, two partial cDNAs encoding human ASM were isolated and sequenced (Quintern et al., 1989, EMBO J. 8:2469–2473). The type 1 cDNA contained an in-frame 172 base pairs (bp) encoding 57 amino acids; in the type 2 cDNA this sequence was replaced by an in-frame 40 bp encoding 13 different amino acids. Of the 92 positive clones identified by cDNA library screening, the type 1 and 2 cDNAs represented about 90% and 10%, respectively (Quintern et al., supra).

3. SUMMARY OF THE INVENTION

The present invention relates to the ASM gene and to methods of diagnosing Niemann-Pick disease (NPD). It is based, at least in part, on the cloning and characterization of full-length cDNAs corresponding to three ASM gene transcripts and the recognition that one species of transcript could be expressed to form the active ASM enzyme. The present invention is further based on the discovery of a frequent missense mutation in the ASM gene that was detected in 32 percent of the Ashkenazi Jewish NPD type A alleles but in only 5.6 percent of ASM alleles from non-Jewish type A patients, and the discovery of a deletion mutant of the ASM gene that is associated with NPD type B disease. Additionally, the genomic sequence and structure of the ASM gene is elucidated herein.

The present invention provides for nucleic acid encoding ASM, substantially purified ASM protein and fragments and derivatives thereof, expression systems for producing ASM, genetically engineered cells and organisms containing a recombinant full-length ASM gene, probes that may be used to diagnose mutations in ASM, assay systems for the diagnosis of NPD, and methods of treatment of NPD.

In one preferred embodiment of the invention, such an assay system may be used to determine the presence of a mutation that results in an arginine to leucine substitution at amino acid residue 496 in Ashkenazi Jewish NPD patients and in prenatal diagnosis, said mutation being associated with NPD type A.

In another preferred embodiment of the invention, such an assay system may be used to determine the presence of a mutation that results in a deletion of an arginine residue at amino acid position 608 in Ashkenazi Jewish NPD patients and in prenatal diagnosis, said mutation being associated with NPD type B.

4. DESCRIPTION OF THE FIGURES

FIG. 1. Northern hybridization and RNase protection analysis of human ASM transcripts in placenta. For the Northern hybridizations (A), about 3 µg of poly(A) human placental RNA was electrophoresed and hybridized with the radiolabeled pASM-1 cDNA insert. The sizes of the RNA molecular mass standards are indicated; the bottom arrow identifies the single 2.5 kb hybridizing transcript. The probe designed for the RNA protection experiment is shown schematically. The expected, protected fragment in a type 1 transcript was 333 bp, whereas in a type 2 transcript the protected fragment would be 266 bp. Lane 1, mock control with no placental RNA; lanes 2 (16-h exposure) and 3 (48-h exposure) contains about 1 µg of human placental RNA. The arrows indicate the type 1 and 2 protected fragments.

FIGS. 2A–2C. PCR amplification of type 2-specific transcripts from human placenta. Sense and antisense PCR primers (indicated by the arrows) were constructed from the full-length type 1 cDNA (pASM-1FL) and the partial type 2 cDNA (pASM-2) sequences, respectively (2C). Following PCR amplification, the products were electrophoresed in 1% agarose gels (2A) and then hybridized with an ASM-specific oligonucleotide (2B). A 1.1 kb product was identified, consistent with the occurrence of a full-length type 2 transcript in placenta.

FIGS. 3A–3C. Nucleotide (SEQ ID NO: 1) and predicted amino acid (SEQ ID NO:2) sequences of the full-length ASM cDNA, pASM-1FL. The pASM-1FL insert was sequenced in both orientations. The unique 172-bp type 1 sequence is bracketed. Underlined amino acid residues represent residues that were colinear with the amino acid sequences from tryptic peptides of the purified enzyme (T-1 to T-12). The boxed amino acid residues are those that were different from the fibroblast cDNAs, pASM-1 and pASM-2. CHO represents potential N-glycosylation sites. FIG. 4. Schematic representation of human ASM type 1, 2 and 3 cDNAs. The longest type 1, 2 and 3 cDNAs isolated by library screening are shown schematically. The type 1- and 2-specific sequences are indicated (172 and 40 bp, respectively), as are the locations of the stop codons. A and B are common 5' and 3' coding sequences, respectively. Note that the partial type 3 cDNA has a premature termination codon (TAA).

Figure 5A:
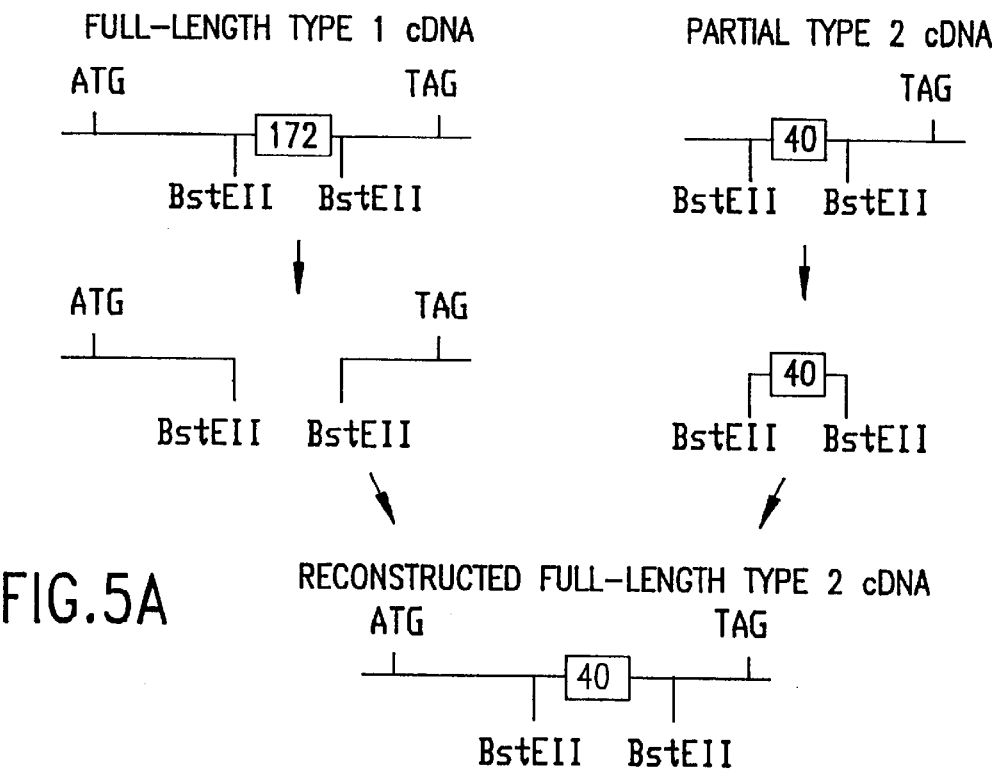

FIG. 5. Reconstruction of full-length type 2 and 3 human ASM cDNAs. The full-length type 2 (A) and 3 (B) cDNAs were reconstructed as described under "Methods." The 172- and 40-bp type 1- and 2-specific sequences are indicated, as are the flanking BstEII restriction sites.

Figure 6B:

FIGS. 6A–6B. Sequence of the PCR amplified genomic region containing the unique type 1- and 2-specific human ASM regions (SEQ ID NO: 3). PCR amplification of human genomic DNA was performed using primers 1 and 2. Upper and lower case letters indicate exonic and intronic sequences, respectively. The type 1- and 2-specific genomic sequences are shown in boldface type. Boxed sequences D1 to D4 and A1 and A2 indicate 5' donor and 3' acceptor splice site sequences, respectively. The potential lariat branch point consensus sequences are underlined and designated a–c.

FIGS. 6C–6H. Nucleotide sequence (SEQ ID NO: 4) of the genomic region encoding human ASM. Upper and lower case letters denote ASM exonic and intronic sequences, respectively. The two potential initiation codons in exon 1 are indicated by a double underline. The type 1-specific region is encoded by exon 3 and the type 2-specific region at the 5' end of intron 2 is underlined. A potential cryptic donor splice site adjacent to the type 2-specific region is indicated by an overline. An Sp 1 binding site and an Alu 1 homology region are boxed. The initiation codons for ORFs 1, 2 and 3 also are underlined and the transcriptional directions are indicated by arrows.

FIG. 7. Proposed model for alternative splicing of ASM transcripts. Type 1 transcripts result from normal splicing events, whereas type 2 RNAs occur due to a single splice which brings together the 3' acceptor, A2 (nt 1590–1591), with the cryptic 5' donor site, D3 (nt 179–180). Thus, the type 2 transcript deletes the 172 bp exon which is replaced by 40 in-frame intronic bp. The type 3 transcript results from a splicing event which joins the 3' acceptor, A2, with the 5' donor, D1 (nt 139–140).

Figure 8:
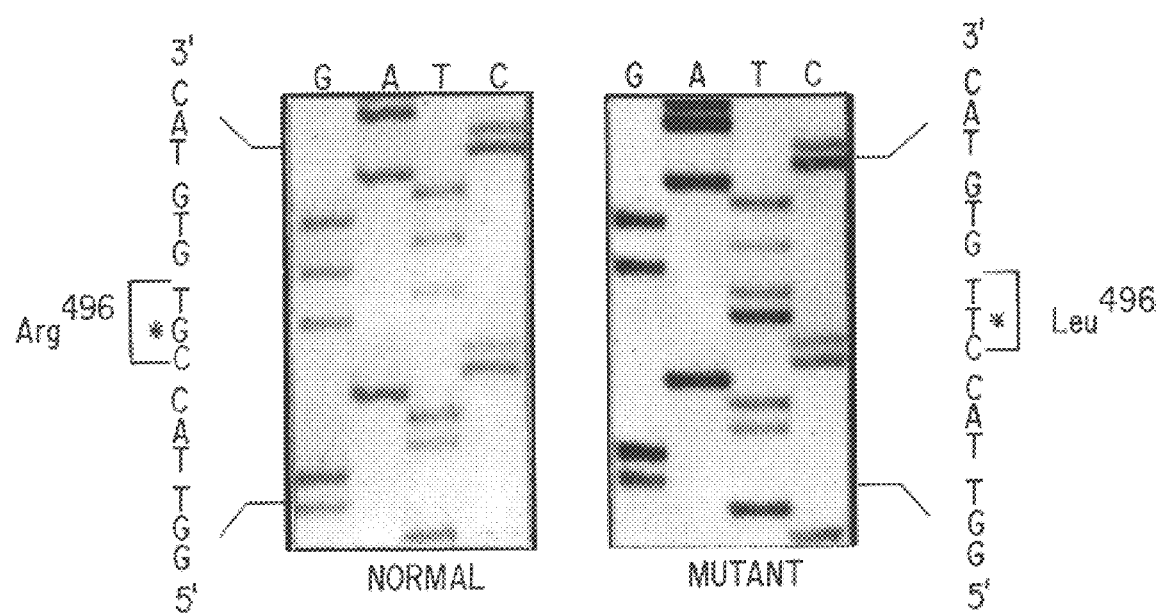

FIG. 8. Partial sequence of the amplified ASM cDNA from an Ashkenazi Jewish type A NPD homozygote (proband 1) showing the G-T transversion of nt 1487. cDNA synthesis, PCR amplification, and DNA sequencing are described. Arrows indicate the G-T transversion in proband 1 (Right) that results in R496L.

Figure 9:
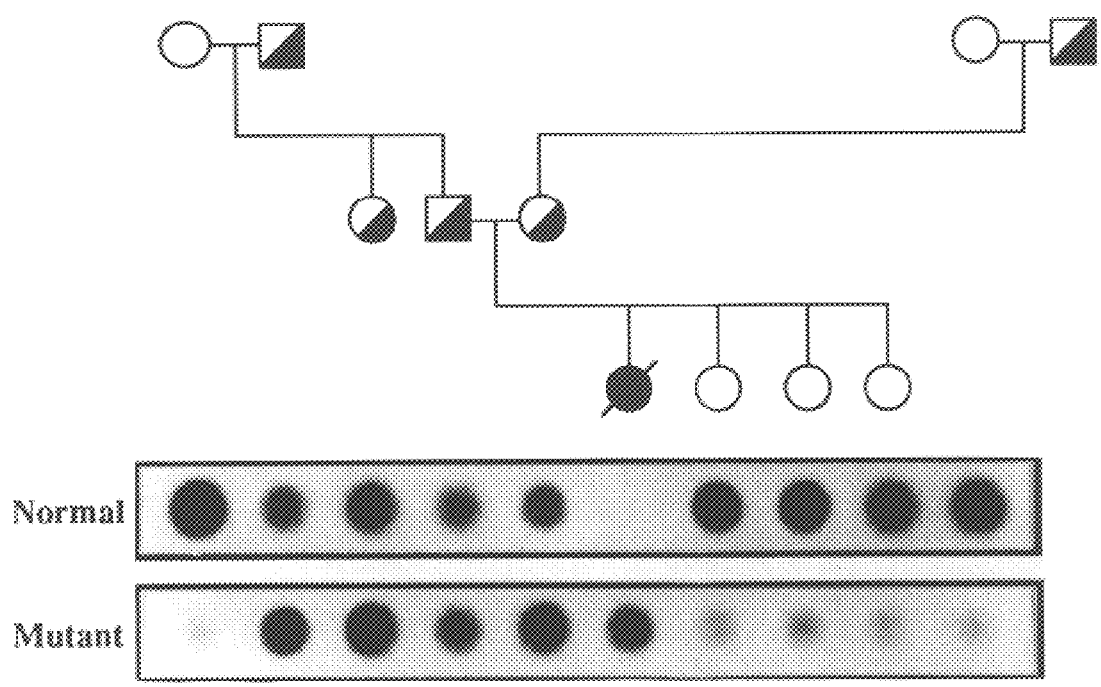

FIG. 9. Identification of R496L (SEQ ID NOS: 5 and 6), in amplified genomic DNAs from the members of an Ashkenazi Jewish family with type A NPD by dot blot hybridization with allele-specific oligonucleotides (ASOs). Note that the affected homozygote (proband 1: o/) was homoallelic, and both of her parents were heterozygous for R496L.

FIG. 10. Identification of a three base deletion in the ASM genomic DNA from proband 2. (a) The methods for PCR amplification of the ASM genomic DNA from proband 2, subcloning of the PCR products and DNA sequencing are described in the text. A small area of the genomic sequence obtained from a normal individual (left) (SEQ ID NOS: 7 and 8) and proband 2 (right) (SEQ ID NOS: 9 and 10) is shown. (b) A schematic representation of the ΔR608 mutation. FIG. 11. Genotype analysis of proband 2 and family members by dot-blot hybridization. The conditions used for dob-blot hybridization of PCR-amplified genomic DNA with the R496L and ΔR608 ASOs are described in the text.

5. DETAILED DESCRIPTION OF THE INVENTION

For purposes of clarity, and not by way of limitation, the detailed description of the invention is divided into the following subsections:

(i) the ASM gene;

(ii) expression of the ASM gene;

(iii) identification of mutations in the ASM gene;

(iv) methods of diagnosing Niemann-Pick disease;

(v) assay systems for diagnosing Niemann-Pick disease; and (vi) methods of treatment of Niemann-Pick disease.

5.1. The Acid Sphingomyelinase Gene

The nucleotide coding sequence and deduced amino acid sequence for the full-length cDNA that encodes functional ASM is depicted in FIGS. 3A–3C (SEQ ID NOS: 1 and 2), and is contained in plasmid pASM-1FL. This nucleotide sequence, or fragments or functional equivalents thereof, may be used to generate recombinant DNA molecules that direct the expression of the enzyme product, or functionally active peptides or functional equivalents thereof, in appropriate host cells. The genomic nucleotide sequence of ASM, its characterization and structural organization is depicted in FIGS. 6C–6H (SEQ ID NO: 4).

Due to the degeneracy of the nucleotide coding sequence, other DNA sequences which encode substantially the same amino acid sequences as depicted in FIG. 3 may be used in the practice of the invention for the cloning and expression of ASM. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The coding sequences for ASM may be conveniently obtained from genetically engineered microorganisms or cell lines containing the enzyme coding sequences. Alternatively, genomic sequences or cDNA coding sequences for these enzymes may be obtained from human genomic or cDNA libraries. Either genomic or cDNA libraries may be prepared from DNA fragments generated from human cell sources. The fragments which encode ASM may be identified by screening such libraries with a nucleotide probe that is substantially complementary to any portion of the sequence depicted in FIGS. 3A–3C (SEQ ID NOS: 1) or FIGS. 6C–6H (SEQ ID NO: 4). Indeed, sequences generated by polymerase chain reaction can be ligated to form the full-length sequence. Although portions of the coding sequences may be utilized, full length clones, i.e., those containing the entire coding region for ASM, may be preferable for expression. Alternatively, the coding sequences depicted in FIGS. 3A–3C may be altered by the addition of sequences that can be used to increase levels of expression and/or to facilitate purification.

Techniques well-known to those skilled in the art for the isolation of DNA, generation of appropriate restriction fragments, construction of clones and libraries, and screening recombinants may be used. For a review of such techniques, see, for example, Sambrook, et al., 1989, Molecular Cloning A Laboratory Manual, 2nd Ed. Cold Spring Harbor Press, N.Y., Chapters 1–18.

In an alternate embodiment of the invention, the coding sequence of FIGS. 3A–3C (SEQ ID NO: 1) could be synthesized in whole or in part, using chemical methods well-known in the art. See, for example, Caruthers, et. al., 1980, Nuc. Acids Res. Symp. Ser. 7:215–233; Crea & Horn, 1980, Nuc. Acids Res. 9(10):2331; Matteucchi & Carruthers, 1980, Tetrahedron Letters 21:719; and Chow and Kempe, 1981, Nuc. Acids Res. 9(12):2807–2817.

Alternatively, the protein itself could be produced using chemical methods to synthesize the amino acid sequence depicted in FIGS. 3A–3C (SEQ ID NO: 2) in whole or in part. The present invention provides for substantially purified ASM, preferably having a sequence substantially as depicted in FIGS. 3A–3C, or a portion thereof that is immunogenic or biologically active. For example, peptides can be synthesized by solid phase techniques, cleaved from the resin and purified by preparative high performance liquid chromatograph. (E.g., see, Creighton, 1983, Proteins, Structures and Molecular Principles, W. H. Freeman & Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman & Co., N.Y., pp. 34–49).

Also, the 5' untranslated and coding regions of the nucleotide sequence could be altered to improve the translational efficiency of the ASM mRNA.

In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered into the ASM enzyme to produce a more active or stable protein, more enzyme protein, or even change the catalytic specificity of the enzyme.

The present invention further provides for organisms containing the functional ASM gene. In various embodiments, such organisms include, but are not limited to, bacteria, yeast, eukaryotic cells, or transgenic animals. Transgenic animals whose own ASM genes have been "knocked out" by homologous recombination and replaced with mutant ASM genes may be used as models of NPD in humans.

5.2. Expression of the Acid Sphingomyelinase Gene

In order to express a biologically active ASM, the coding sequence for the enzyme, a functional equivalent, or a modified sequence, as described in Section 5.1., supra, is inserted into an appropriate expression vector, i.e., a vector which contains the necessary elements for transcription and translation of the inserted coding sequence in appropriate host cells. Host cell expression systems which possess the cellular machinery and elements for the proper processing, i.e., signal cleavage, glycosylation, phosphorylation and protein sorting are preferred. For example, mammalian host cell expression systems are preferred for the expression of biologically active enzymes that are properly folded and processed; when administered in humans such expression products should exhibit proper tissue targeting and no adverse immunological reaction.

5.2.1. Construction of Expression Vectors and Preparation of Transfectants

Methods which are well-known to those skilled in the art can be used to construct expression vectors containing the ASM coding sequence and appropriate transcriptional/translational control signals. These methods include in vitro recombination/genetic recombination. See, for example, the techniques described in maniatis et al., 1982, Molecular Cloning A Laboratory Manual, Cold spring Harbor Laboratory, N.Y., Chapter 12.

In bacterial systems a number of expression vectors may be advantageously selected depending upon the use intended for the ASM protein expressed. For example, when large quantities of ASM are to be produced, vectors which direct the expression of high levels of fusion protein products that are readily purified may be desirable. Such vectors include but are not limited to the E. coli expression vector pUR278 (Ruther et al., 1983, EMBO J. 2:1791), in which the ASM coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like.

A variety of eukaryotic host-expression systems may be utilized to express the ASM coding sequence. Although prokaryotic systems offer the distinct advantage of ease of manipulation and low cost of scale-up, their major drawback in the expression of ASM is their lack of proper post-translational modifications of expressed mammalian proteins. Eukaryotic systems, and preferably mammalian expression systems, allow for proper modification to occur. Eukaryotic cells which possess the cellular machinery for proper processing of the primary transcript, glycosylation, phosphorylation, and, advantageously secretion of the gene product should be used as host cells for the expression of ASM. Mammalian cell lines are preferred. Such host cell lines may include but are not limited to CHO, VERO, BHK, HeLa, COS, MDCK, –293, WI38, etc. Appropriate eukaryotic expression vectors should be utilized to direct the expression of ASM in the host cell chosen. For example, at least two basic approaches may be followed for the design of vectors on SV40. The first is to replace the SV40 early region with the gene of interest while the second is to replace the late region (Hammarskjold, et al., 1986, Gene 43: 41). Early and late region replacement vectors can also be complemented in vitro by the appropriate SV40 mutant lacking the early or late region. Such complementation will produce recombinants which are packaged into infectious capsids and which contain the ASM gene. A permissive cell line can then be infected to produce the recombinant protein. SV40-based vectors can also be used in transient expression studies, where best results are obtained when they are introduced into COS (CV-1, origin of SV40) cells, a derivative of CV-1 (green monkey kidney cells) which contain a single copy of an origin defective SV40 genome integrated into the chromosome. These cells actively synthesize large T antigen (SV40), thus initiating replication from any plasmid containing an SV40 origin of replication.

In addition to SV40, almost every molecularly cloned virus or retrovirus may used as a cloning or expression vehicle. Viral vectors based on a number of retroviruses (avian and murine), adenoviruses, vaccinia virus (Cochran, et al., 1985, Proc. Natl. Acad. Sci. USA 82: 19) and polyoma virus may be used for expression. Other cloned viruses, such as JC (Howley, et al., 1980, J. Virol 36: 878), BK and the human papilloma viruses (Heilman, et al., 1980, J. Virol 36: 395), offer the potential of being used as eukaryotic expression vectors. For example, when using adenovirus expression vectors the ASM coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing the human enzyme in infected hosts (e.g., see Logan & Shenk, 1984, Proc. Natl. Acad. Sci. (USA) 81:3655–3659). Alternatively, the vaccinia virus 7.5K promoter may be used. (e.g., see, Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931). Of particular interest are vectors based on bovine papilloma virus (Sarver, et al., 1981, Mol. Cell. Biol. 1:486). These vectors have the ability to replicate as extrachromosomal elements. Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters such as the metallothionine IIA promoter, heat shock promoters, etc.

For long-term, high-yield production of recombinant proteins, stable expression is preferred. For example, following the introduction of foreign DNA, engineered cells may be allowed to grow for 1–2 days in an enriched media, and then are switched to a selective media. Rather than using expression vectors which contain viral origins of replication, host cells can be transformed with the ATN or DNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Alternative eukaryotic expression systems which may be used to express the ASM enzymes are yeast transformed with recombinant yeast expression vectors containing the ASM coding sequence; insect cell systems infected with recombinant virus expression vectors (e.g., baculovirus) containing the ASM coding sequence; or plant cell systems infected with recombinant virus expression vectors (e.g., cauliflower mosaic virus, CaMV; tobacco mosaic virus, TMV) or transformed with recombinant plasmid expression vectors (e.g., Ti plasm id) containing the ASM coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516–544, Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. For complementation assays in yeast, cDNAs for ASM may be cloned into yeast episomal plasmids (YEp) which replicate autonomously in yeast due to the presence of the yeast $2\mu$ circle. The cDNA may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. D M Glover, 1986, IRL Press, Wash., D.C.). Constructs may contain the 5' and 3' non-translated regions of the cognate ASM mRNA or those corresponding to a yeast gene. YEp plasmids transform at high efficiency and the plasmids are extremely stable. Alternatively, vectors may be used which promote integration of foreign DNA sequences into the yeast chromosome.

In cases where plant expression vectors are used, the expression of the ASM coding sequence may be driven by any of a number of promoters. For example, viral promoters such as the 35S RNA and 19S RNA promoters of CAMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express ASM is an insect system. In one such system, *Autographa californica* nuclear polyhedrosis virus (ACNPV) is used as a vector to express foreign genes. The virus grows in. *Spodoptera frugiperda* cells. The ASM sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

5.2.2. Identification of Transfectants or Transformants Expressing the Ash Product The host cells which contain the ASM coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of ASM mRNA transcripts in the host cell; and (d) detection of the gene product as measured by immunoassay or by its biological activity.

In the first approach, the presence of the ASM coding sequence inserted in the expression vector can be detected by DNA-DNA or DNA-RNA hybridization using probes comprising nucleotide sequences that are homologous to the ASM coding sequence substantially as shown in FIGS. 3A–3C (SEQ ID NO: 1), or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the ASM coding sequence is inserted within a marker gene sequence of the vector, recombinants containing the ASM coding sequence can be identified by the absence of the marker gene function. Alternatively, a marker gene can be placed in tandem with the ASM sequence under the control of the same or different promoter used to control the expression of the ASM coding sequence. Expression of the marker in response to induction or selection indicates expression of the ASM coding sequence.

In the third approach, transcriptional activity for the ASM coding region can be assessed by hybridization assays. For example, RNA can be isolated and analyzed by Northern blot using a probe homologous to the ASM coding sequence or particular portions thereof substantially as shown in FIGS. 3A–3C (SEQ ID NO: 1). Alternatively, total nucleic acids of the host cell may be extracted and assayed for hybridization to such probes.

In the fourth approach, the expression of the ASM protein product can be assessed immunologically, for example, by Western blots, immunoassays such as radioimmunoprecipitation, enzyme-linked immunoassays and the like. The ultimate test of the success of the expression system, however, involves the detection of the biologically active ASM gene product. Where the host cell secretes the gene product, the cell free media obtained from the cultured transfectant host cell may be assayed for ASM activity. Where the gene product is not secreted, cell lysates may be assayed for such activity. In either case, a number of assays can be used to detect ASM activity including but not limited to assays employing N-12[(12 pyrenesulfonyl amidododecanoyl)]-sphingomyelin ($PAS_{12}$) (Klar et al., 1988, Clin. Chem. Acta 176:259–268), or other substrates for ASM.

5.2.3. Purification of the Ash Gene Product

Once a clone that produces high levels of biologically active ASM is identified, the clone may be expanded and used to produce large amounts of the enzyme which may be purified using techniques well-known in the art including, but not limited to, immunoaffinity purification, chromatographic methods including high performance liquid chromatography and the like. Where the enzyme is secreted by the cultured cells, ASM may be readily recovered from the culture medium.

Where the ASM coding sequence is engineered to encode a cleavable fusion protein, the purification of ASM may be readily accomplished using affinity purification techniques.

5.3. Identification of Mutations of the Acid Sphingomyelinase Gene

The present invention also provides for methods of identifying mutations of the ASM gene. Such mutations include but are not limited to substitutions, insertions, or deletions in the nucleic acid or amino acid sequence of the ASM gene. According to these embodiments, nucleic acid probes derived from known ASM genes may be used to identify mutant ASM sequences in DNA or RNA obtained from a human subject suspected of carrying an ASM mutation. Such probes may be used in standard hybridization procedures for screening genomic or cDNA libraries (e.g. Benton and Davis, 1977, Science 196:180), or may be used in procedures that amplify mutant sequences, including polymerase chain reaction (PCR; Saiki et al., 1985, Science 230:1350–1354).

For example, and not by way of limitation, PCR may be used to identify mutations in the ASM gene as follows. Total RNA and genomic DNA may be prepared from cells (including cell lines) derived from a person suspected of carrying an ASM mutation using standard techniques (Sambrook et al., 1989, in "Molecular Cloning: A Laboratory Manual," Cold Spring Harbor Laboratory, Cold Spring Harbor, N.Y.). First-strand cDNA may be reverse-transcribed from about 5 $\mu$g of total RNA by using a cDNA synthesis kit according to the manufacturer's instructions (e.g., Boehringer Mannheim). The cDNA (about 10% of the total reaction) or genomic DNA (about 0.5 μg) may be amplified by PCR using *Thermus aguaticus* (Tag) polymerase, essentially as described by Saiki, supra, with the following conditions and modifications. PCR may desirably be performed for 30 to 40 cycles consisting of denaturation for 1 min. at 94 degrees C. and hybridization and extension for 4 min. at 66 degrees C. To improve the specificity of the PCR amplification, a "PCR boost" procedure may be used. In this procedure, the concentrations of the primers and Taq polymerase may be about 0.1 μM and 5 units/ml, respectively, for the first 15 cycles. Then each primer may be added to a final concentration of about 0.5 μM, and an additional 2 units of Taq polymerase may be added to the reaction mixture. PCR amplification may then be continued for an additional 15–25 cycles. For use as primers in the PCR, pairs of sense and antisense primers may be prepared by any method known in the art, including synthesis on. an Applied Biosystems model 380B DNA synthesizer (Itakura et al., 1984, Annu. Rev. Biochem. 53:323–356) and used to specifically amplify, for example, either (i) the entire coding region of reverse-transcribed type 1 ASM transcript in three overlapping cDNA fragments and/or (ii) the 1665-bp genomic region containing the alternatively spliced sequences in type 1 and 2 ASM cDNAs. For these purposes, the following primers may be used:

(i) to amplify the coding region of reverse-transcribed type 1 ASM transcript, (a) a 984 bp fragment from the 5' end may be amplified using the 29-mer sense primer, P1 (5'AGTAGTCTCGAGACGGGACAGACGAACCA-3') (SEQ ID NO: 11), corresponding to ASM nucleotide −39 to −23 with an additional 12 nucleotides that include an XhoI restriction site, and the 31-mer antisense primer, P2 (5'-AGTAGTCTGCAGAGCAGGGTACATGGCACTG-3') (SEQ ID NO: 12), corresponding to ASM nucleotide 926 to 945 with an additional 12 nucleotides containing a HindIII restriction site. To amplify an internal 383-bp fragment of the ASM cDNA, the 29-mer sense primer, P3 (5'-ATCATCAAGCTTGGGTAACCATGAAAGCA-3') (SEQ ID NO: 13) may be used corresponding to ASM nucleotides 947–964 with an additional 12 nucleotides containing a HindIII restriction site, and the antisense 32-mer primer, P4 (5'-ATCATCGAATTCTACAATTCGGTAATAATTCC-3') (SEQ ID NO: 14), corresponding to ASM nucleotides 1310 to 1330 with an additional 12 nucleotides containing an EcoR1 restriction site. To amplify a 789 bp 3' fragment from ASM cDNA, a 19-mer sense primer, P5 (5'-CTCCACGGATCCCGCAGGA-3') (SEQ ID NO: 15), corresponding to ASM nucleotides 1185 to 1203 and containing an internal BamHI restriction site may be used together with an antisense 32-mer primer, P6 (5'-AGTAGTGTCGACTTGCCTGGTTGAACCACAGC-3') (SEQ ID NO: 16) corresponding to ASM nucleotides 1955 to 1974 with an additional 12 nucleotides containing a SalI restriction site;

(ii) to amplify the 1665 base pair genomic region containing the alternatively spliced sequences in type 1 and 2 ASM cDNAS, primers P3 and P4 (supra) may be used.

The products of PCR may then be subcloned into an appropriate vector such as, for example, Bluescript KS (+) (Stratagene, La Jolla, Calif.) or pGEM 9ZF (−) (Promega, Madison, Wis.). For each amplified product, it may be desirable to sequence multiple (e.g., four to ten) independent subclones, by methods known in the art, including, but not limited to, the dideoxy method (Sanger et al., 1977, Proc. Natl. Acad. Sci. U.S.A., 74:5463–5467). The sequences thus obtained may be compared to the sequence of ASM type 1 as set forth in FIG. 3 in order to identify mutations.

The use of this method in identifying mutations in ASM is exemplified in Sections 7 and 8, infra, which relate to the Arg-Leu substitution at residue 496 (SEQ ID NO: 34) and to the Arg deletion at residue 608 (SEQ ID NO: 35), respectively. The present invention provides nucleic acids comprising these mutations, as set forth in FIG. 8 (SEQ ID NO: 6) and FIG. 10 (SEQ ID NO: 9), respectively, and primers which may be used to identify these mutations (see infra).

5.4. Methods of Diagnosing Niemann-Pick Disease

The present invention also provides for a method of diagnosing Niemann-Pick disease (NPD) in a patient, comprising detecting a mutation in an ASM gene, in a nucleic acid sample of the patient in which the mutation positively correlates with NPD. Such methods may be particularly useful when they distinguish NPD type A from NPD type B, because the two types of disease carry clinically very different prognoses. Such a distinction may be made by detecting the presence or absence of an ASM mutation which is selectively associated with type A or type B disease. Such mutations, in particular embodiments, comprise an alteration of at least one amino acid in the sequence set forth in FIGS. 3A–3C (SEQ ID NO: 2).

The methods of diagnosis of the invention may be used to diagnose NPD in a patient that is suspected of suffering from NPD or, alternatively, in a patient that is a fetus by prenatal diagnosis, using techniques such as amniocentesis or chorionic villi sampling or by any technique known in the art.

In related embodiments, the present invention also provides for a method of identifying a person as having the potential to genetically transmit NPD comprising detecting a mutation in an ASM gene in a nucleic acid sample of the person, in which the mutation positively correlates with the ability to genetically transmit NPD. A nucleic acid sample may be obtained from any suitable source of the individual's cells or tissues. In such embodiments, it may again be preferable to distinguish the potential for transmitting NPD type A versus type B.

It should be noted that persons capable of transmitting NPD but who do not themselves suffer from NPD are likely to be heterozygotes with respect to the ASM gene; that is, they carry one mutant and one normal gene. Persons that suffer from NPD are likely to lack a normal ASM gene altogether and to instead carry mutations in the ASM gene in both number 11 chromosomes, although these mutant genes need not be the same.

Mutations in the ASM gene may be detected by the methods set forth in Section 5.3., supra, for cloning and identifying new mutations. Alternatively, mutations that have already been identified and characterized using the methods set forth in Section 5.3 may be detected. For example, and not by way of limitation, the arginine to leucine mutation at amino acid residue 496 of ASM (the R496L mutation) NPD type A allele (see Section 7, infra), or the arginine deletion at amino acid 608 (the ΔR608 mutation) allele associated with type B NPD (see Section 8, infra), may be detected in methods of diagnosing NPD or of identifying a person as being capable of genetically transmitting NPD and in particular NPD type A or type B. Such probes may be particularly useful when analyzing the genetic material from persons of Ashkenazi Jewish descent.

The presence of a mutation may be detected by any method known in the art, including cloning and sequencing the ASM gene from the person to be tested. In preferred methods of the invention, the presence of the mutation is detected by amplifying the nucleic acids spanning the mutation within the ASM gene, using sense and antisense oligonucleotide primers designed to span the area of the ASM gene that contains the mutation. For example, in specific embodiments of the invention, nucleic acid collected from the person to be tested (prepared from tissue, cells, blood, amniotic fluid or other body fluids, etc.) may be utilized in PCR as described in Section 5.3, supra, using the following primer pairs. To detect the R496L mutation or the ΔR608 mutation, a 27-mer sense primer, P7 (5'-AGTAGTCGACATGGGCAGGATGTGTGG-3') (SEQ ID NO: 17) may be used together with antisense primer P6 (see supra) to amplify a 567 bp genomic fragment containing the G-T transversion. The resulting products of PCR may then be sequenced or, preferably, be analyzed for the ability to hybridize to a normal ASO or an oligonucleotide containing a defined mutation. In this specific example, the R496L mutation can be detected by hybridizing the PCR amplified sample to either the normal oligonucleotide P8 (5'-CTATTTGGTACACACGG-3') (SEQ ID NO: 18) or the mutation-specific oligonucleotide P9 (5'-CTATTTGGTACACAAGG-3') (SEQ ID NO: 19), in which selective hybridization to P9 positively correlates with the presence of the R496L mutation. Similarly, the ΔR608 mutation can be detected by hybridizing the PCR amplified sample to either the P10 normal oligonucleotide (5'-CTCTGTGCCGCCACCTG-3') (SEQ ID NO: 20) or the mutation-specific oligonucleotide P11 (5'-GCTCTGTGCCACCTGAT-3') (SEQ ID NO: 21) (see Sections 7 and 8, infra).

In specific embodiments of the invention, such hybridization may be done using dot-blot hybridization (Sambrook et al., supra), using, for example, Zetabind nylon membranes (AMF Cuno) and Bio-Rad dot-blot apparatus. Hybridization may be performed for at least 3 hours at 30 degrees C. After hybridization, the blots may be washed at room temperature for 15 minutes in 6×SSC (1×SSC is 0.15 M sodium chloride/0.015 M sodium citrate, pH 7.0)/0.1% SDS and then for 2 hours in the same solution at either about 53–54 degrees C. for the normal allele or about 48–50 degrees C. for the mutant allele.

With regard to the R496L mutation, it was detected in 32% (10 of 31) of Ashkenazi Jewish NPD type A alleles studied; in only 5.6% (2 of 36) of ASM alleles from non-Jewish type A patients, in one of two Ashkenazi Jewish NPD type B patients, and in none of 180 ASM alleles from normal individuals of Ashkenazi Jewish descent. It therefore appears that the R496L mutation results in neuronopathic type A disease when homoallelic and nonneuronopathic type B phenotype when heteroallelic with a type B mutation such as TR608. In contrast, the ΔR608 mutation appears to occur frequently in Type B NPD patients of Ashkenazi Jewish descent.

5.5. Assay Systems for Diagnosing Niemann-Pick Disease

The present invention also provides for kits and assay systems that may be used in the methods described in Section 5.4, supra. Such kits comprise oligonucleotide primers that may be used to identify mutations in the ASM gene.

The following kits are specific, non-limiting embodiments of the invention.

(i) A kit for identifying new mutations in the ASM gene comprising oligonucleotide primers P1, P2, P3, P4, P5 and P6 (supra);

(ii) A kit for detecting the R496L or ΔR608 mutation in the ASM gene comprising oligonucleotide primers P6 and P7 (supra);

(iii) A kit for detecting the R496L mutation consisting of the kit in (ii), supra, and further comprising oligonucleotide hybridization probes P8 and P9 (supra);

(iv) A kit for detecting the ΔR608 mutation consisting of the kit in (ii) supra, and further comprising oligonucleotide hybridization probes P10 and P11 (supra).

5.6. Methods of Treatment of Niemann-Pick Disease

The present invention also provides for methods of treatment of NPD, particularly type B disease, comprising administering to a patient in need of such treatment an effective amount of substantially purified ASM type 1, prepared as described supra, or a derivative thereof. For example, the recombinant enzyme could be administered at a dosage ranging from 0.1 mg/kg to about 10 mg/kg and, preferably from about 0.1 mg/kg to about 2 mg/kg. The ability to produce large amounts of the recombinant enzyme or substantially pure enzyme in accordance with this invention will permit the evaluation of the therapeutic effect of significantly larger doses.

Alternatively, treatment can be provided by administering to a patient in need of such treatment an effective amount of nucleic acid encoding functional ASM type 1, e.g., the having sequence set forth in FIGS. 3A–3C (SEQ ID NO: 1). Such nucleic acid may be administered via a suitable vector, including retroviral or other viral vectors, or may be administered via cells transfected with ASM type-1 encoding nucleic acid.

5.7. Engineering Transgenic Animals Containing the Human ASM Gene

The gene sequence of ASM is disclosed herein. The cDNA sequence of FIGS. 3A–3C (SEQ ID NO: 1) or the genomic sequence of FIGS. 6C–6H (SEQ ID NO: 4) can be engineered in transgenic animals to produce a model system for studying the synthesis and regulation of the ASM enzyme. In particular, animals containing the various mutations disclosed herein can be engineered to study the effects of the mutation on the synthesis, regulation and function of ASM. Any technique known to those skilled in the art can be used to produce the transgenic animals.

The engineering of transgenic mice containing the wild type gene is described in Section 6.2.7. infra.

6. Example: Isolation Nucleotide Sequence, and Expression of the Full Length and Alternatively Spliced cDNAS Encoding Human Acid Sphingomyelinase

6.1. Materials and Methods

6.1.1. Materials

Normal human placental tissue was frozen at −70° C. within 30 minutes of delivery and stored until use. λgt11 human placental, testis, and hepatoma cDNA libraries were obtained from Clontech Laboratories (Palo Alto, Calif.). A λgt11 human retinal cDNA library was kindly provided by Dr. Jeremy Nathans (Johns Hopkins University, Baltimore, Md.). Restriction endonucleases, T4 DNA ligase, T4 polynucleotide kinase, the Klenow fragment of DNA polymerase 1, RNA molecular weight markers, and cDNA synthesis kits were obtained from New England Biolabs (Beverly, Mass.) and/or from Boehringer Mannheim. Taq polymerase was purchased from Perkin-Elmer Cetus Instruments, and Sequenase DNA sequencing kits were from U.S. Biochemical Corp. Bluescript vectors and helper phage, RNA transcription kits, Proteinase K, and RNase-free DNase 1 were obtained from Stratagene (La Jolla, Calif.). RNase T1 was from Bethesda Research Laboratories. Nitrocellulose (type HATF) and nylon membranes were purchased from Millipore (Bedford, Mass.). Reagents for DNA synthesis were obtained from Applied Biosystems (Foster City Calif.). Radioactive nucleotides and multiprime DNA labeling kits were from Amersham Corp. N-12[(1-Pyrenesulfonyl) amidododecanoyl]-sphingomyelin was a gift from Dr. Shimon Gatt, Hebrew University-Hadassah Medical Center (Jerusalem, Israel). The eukaryotic expression vector p91023(B) was obtained from Dr. Randal Kaufman, Genetics Institute (Boston, Mass.). All other reagents were the highest grade available from commercial sources.

6.1.2. Northern Hybridization, RNase Protection Analyses, and Type 2-Specific PCR Amplification Total cellular RNA from human placenta (~5 g) was prepared by a modification of the guanidine isothiocyanate procedure (Chirgwin et al., 1979, Biochemistry 18:5294–5299), and poly(A)$^+$ RNA was isolated by oligo (dT)-cellulose chromatography. Aliquots of total (~10 μg) and poly(A)$^+$ RNA (~3 μg) RNAs were analyzed by electrophoresis through denaturing formaldehyde-agarose gels. Northern hybridizations were performed by standard techniques (Thomas, 1980, Proc. Natl. Acad. Sci. U.S.A. 77:5201–5205) using the radiolabeled pASM-1 insert as a probe. RNase protection experiments were performed according to the method of Zinn et al. (Zinn et al., 1983, Cell 34:865–879). A 333-bp BamHI-SacI restriction fragment isolated from pASM-1FL was subcloned into the SK(+) Bluescript vector in order to prepare the radiolabeled riboprobe. After RNase treatment, the protected fragments were electrophoresed in 6.0% denaturing polyacrylamide gels, and the intensity of the autoradiogram was determined by densitometry. For the amplification of type 2-specific cDNAs, a type 2-specific antisense oligonucleotide (5'-ATCATTGAATTCCACGGACGATAAGTAC -3') (SEQ ID NO: 22) was used with a sense oligonucleotide (5'-ATCATCCTCGAGACGGGACAGACGAACCA-3') (SEQ ID NO: 23) constructed from the 5' end of the pASM-1FL cDNA insert. For the template, cDNA was prepared from total placental RNA using a cDNA synthesis kit according to the manufacturer's instructions. Alternatively, the pASM-1FL insert was used as a template to demonstrate the type 2 specificity of the PCR amplification.

6.1.3. cDNA Library Screening and Isolation of the Full-Length Human Type 1 ASM cDNA For library screenings, human placental, testis, hepatoma, and retinal gt11 cDNA libraries were plated at densities of ~10,000 plaques/150-mm Petri dish. Initially, the placental library was screened using a 404-bp BstEII fragment isolated from the type 2 human ASM partial cDNA, pASM-2 (Quintern et al., 1989, EMBO J. 8:2469–2473). This fragment contained the type 2-specific 40-bp region, as well as flanking sequences common to the type 1 and 2 cDNAs. The hepatoma cDNA library was screened with an oligonucleotide (5'-GTTCCTTCTTCAGCCCG-3') (SEQ ID NO: 24) constructed from the 5' end of the longest partial type 1 cDNA previously isolated and then was analyzed for the presence of type 2 cDNAs as described below. The testis library was screened first with the type 2-specific oligonucleotide (40-mer) and then with a 608-bp PstI-SacI restriction fragment isolated from a type 2 cDNA (Quintern et al., supra). The retinal library was screened with the full-length type 1 placental cDNA (PASM-1FL). Random primer labeling of the cDNA probe with [γ-32P]dCTP (~3000 Ci/mmol), 5' end labeling of the PstI oligonucleotides with T4 polynucleotide kinase and [γ-32P]ATP (>5000 Ci/mmol), and filter hybridizations were performed by standard methods (Sambrook et al., 1989, Molecular Cloning: A Laboratory Manual, 2nd ed., Cold Spring Harbor Laboratory, Cold Spring Harbor, N.Y.). After three rounds of purification. DNA was isolated from putative positive plaques by the plate lysate method, and the cDNA inserts were analyzed on 1% agarose gels by Southern hybridization (Southern, 1975, J. Mol. Biol. 98:503–517) with oligonucleotides constructed from the type 1- and 2-specific regions and ASM intronic sequences.

6.1.4. DNA Sequencing and Computer-Assisted Analyses

Dideoxy sequencing was performed by the method of Sanger et al. (Sanger et al., 1977, Proc. Natl. Acad. Sci. U.S.A. 74:5463–5467). A putative positive full-length human type 1 ASM cDNA insert (pASM-1FL,) and a representative partial type 3 cDNA insert (pASM-3) were isolated after digestion with EcoR1 and electrophoresis through agarose gels. Briefly, the inserts were cut out of the gels, phenol was added, and then the samples were freeze-thawed in an ethanol bath. Following centrifugation at ~10,000×g, the aqueous phases were re-extracted with phenol and phenol:chloroform (1:1, v/v), and the DNA was then isolated by ethanol precipitation. The purified inserts were subcloned in both orientations into the Bluescript vector SK(+) for sense and antisense strands, and single-stranded template was rescued using VCS13 helper phage for dideoxy sequencing according to the manufacturer's instructions. Sequencing primers were synthesized on an Applied Biosystems model 380B DNA synthesizer using phosphoramidite chemistry (Itakura et al., 1984, Annu. Rev. Biochem. 53:323–356). Computer analyses were performed using the University of Wisconsin Genetics Computer Group DNA sequence analysis software (version 6.2) and GenBank (release 64) and NBRF (release 25) DNA and protein bases, respectively.

6.1.5. Analysis of Polymorphic-Sites in the Human ASM Coding Region

To determine the population frequency of the base differences in codons 322 and 506 of the full-length ASM transcript, PCR amplification of genomic DNA from 20 normal Caucasian individuals was performed on a Perkin Elmer-Cetus thermal cycler using Taq polymerase according to the method of Saiki et al. (Saiki et al., 1988, Science, 239:487–491). For the codon 322 base difference, sense (5'-AGTAGTCGACTGCTAGAGCAATCAGAG-3') (SEQ ID NO: 25) and antisense (5'-AGTGTCGACTCGTCAGGACCAAC-3') (SEQ ID NO: 26) PCR primers were constructed as described above to amplify a 375-bp genomic DNA fragment. For the codon 506 base difference, sense (5'-AGTAGTCGACATGGGCAGGATGTGTGG-3') (SEQ ID NO: 17) and antisense (5'-AGTAGTGTCGACTTGCCTGGTTGAACCACAGC-3') (SEQ ID NO: 16) primers were constructed to amplify a 567-bp genomic DNA fragment. For these studies genomic DNA was rapidly isolated from whole blood by the following procedure. About 0.5 ml of whole blood and 0.5 ml of lysis buffer (10 mM Tris/HCl buffer, pH 7.5, containing 5 mM $MgCl_2$, 0.32 M sucrose, and 1% Triton X-100) was mixed at room temperature. Following centrifugation at 13,000×g, the supernatant was removed, and 0.5 ml of PCR buffer (10 mM Tris/HCl buffer, pH 8.3, containing 50 mM KCl, 2.5 mM $MgCl_2$, 0.1 mg/ml gelatin, 0.45% Nonidet P-40, 0.45% Tween 20, and 0.1 mg/ml Proteinase K) was added. The samples were incubated at 60° C. for 1 h and boiled for 10 minutes to inactivate the protease, and then 25 $\mu$l was removed for PCR amplification. Following agarose gel electrophoresis of the PCR products, the concentration of each product was estimated by ethidium bromide staining.

For the dot-blot hybridization analyses (Sambrook et al., supra), about 0.5 $\mu$g of DNA was used. The sequence-specific oligonucleotide probes were 5'-ATGAAGCAATACCTGTC-3' (Ile-322) (SEQ ID NO: 27), 5'-ATGAAGCAACACCTGTC-3' (Thr-322) (SEQ ID NO: 28), 5'ACTACTCCAGGAGCTCT-3'(Arg-506) (SEQ ID NO: 29), and 5'-ACTACTCCGGGAGCTCT-3' (Gly-506) (SEQ ID NO: 30). Hybridizations were performed for at least 3 h at 42° C. Following hybridization, the blots were washed at room temperature for 15 minutes in 6×SSC containing 0.1% sodium dodecyl sulfate and then for 2 h in the same solutions at either 51° C. (Ile-322 and Arg-506) or 53° C. (Thr-322 and Gly-506).

6.1.6. Reconstruction of Full-Length Type 2 and 3 cDNAS

Figure 5B:
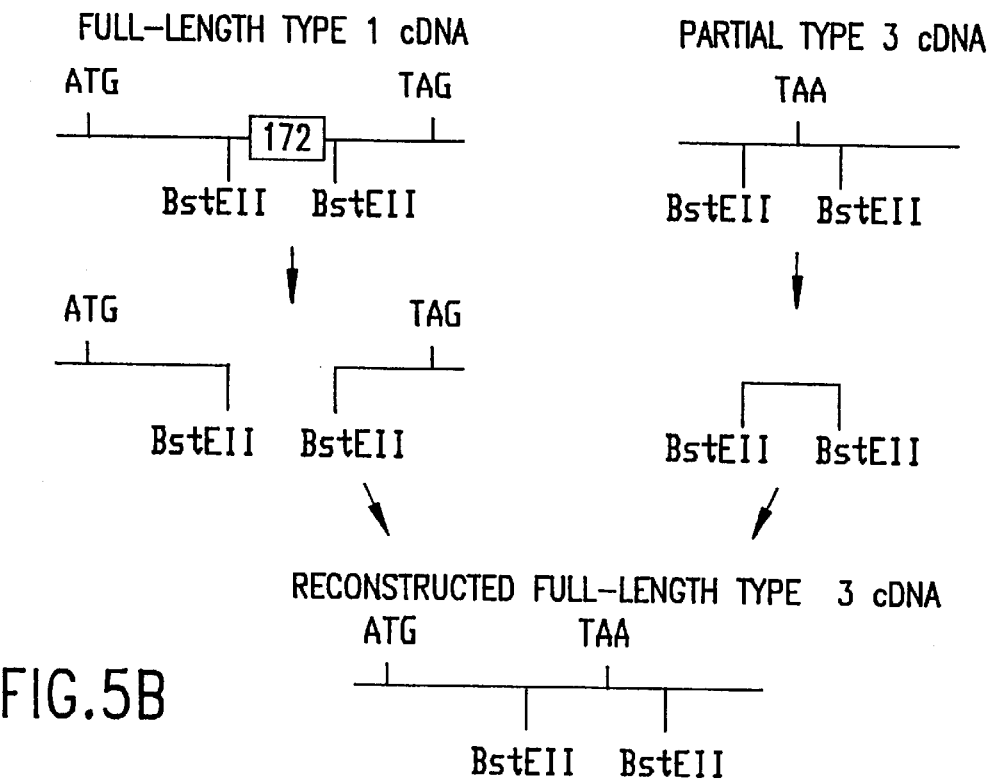

Since extensive library screening did not identify full-length type 2 or 3 cDNAs, they were reconstructed as outlined in FIGS. 5, A and B. For the full-length type 2 cDNA (pASM-2FL) a 400-bp BstEII restriction fragment containing the type 2-specific 40-bp sequence was isolated from the partial type 2 cDNA, pASM-2, by the phenol/freeze-thaw method described above. The full-length type 1 cDNA, pASM-1FL, was then digested with BstEII to remove the fragment containing the type 1-specific sequence for replacement with the type 2-specific BstEII fragment. Analogously, the full-length type 3 cDNA (pASM-3FL) was reconstructed using a 360-bp type 3-specific BstEII restriction fragment. (FIG. 5B).

6.1.7. Transient Expression in COS-1 Cells and Stable Expression in CHO Cells For transient expression experiments in COS-1 cells, the full-length pASM-1FL insert and the reconstructed full-length pASM-2FL and pASM-3FL cDNA inserts were subcloned in both orientations into the EcoRI site of the eukaryotic expression vector, p91023(B) (Kaufman and Sharp, 1982, Mol. Cell. Biol. 2:1304–1319). Full length pASM-1FL inserted in expression vector, p91023(B) was designated p91-ASM. DNA (~5–20 $\mu$g) from sense and antisense constructs was then transfected into COS-1 cells by the method of Chen and Okayama (Chen and Okayama, 1987, Mol. Cell. Biol. 7:2747–2752). The transfected cells were harvested after 72 h, and the ASM and β-glucuronidase enzymatic activities were determined using N-12[(12 pyrenesulfonyl)amidododecanoyl]-sphingomyelin and 4-methylumbelliferyl-β-glucuronide, respectively (Klar et al., 1988, Clin. Chem. Acta 176:259–268; Brot, et al., 1978, Biochemistry 17:385–391). Neutral sphingomyelinase activities were determined as previously described (Gatt et al., 1978, J. Neurochem. 31:547–551). A unit of enzymatic activity equaled that amount of enzyme which hydrolyed 1 nmol of substrate/h. Protein determinations were performed by a modified fluorescamine assay (Bishop and Desnick, 1981, J. Biol. Chem. 256:1307–1316). In addition to antisense constructs, mock transfections were performed as controls.

For stable expression the CHO DG44 dhfr⁻ cell line was utilized (Urlaug et al., 1986, Somat. Cell Genet. 12: 555–566). The CHO cells were maintained at 37° C. in 5% $CO_2$ in Dulbecco's Modified Eagle Medium (DMEM) with 10% fetal calf serum (FCS), antibiotics, 0.05 mM hypoxanthine and 0.008 mM thymidine. Following transfection, the recombinant CHO lines were grown in DMEM supplemented with 10% dialyzed FCS in the absence or presence of methotrexate (MTX).

6.1.8. PCR Amplification of Genomic DNA

For the genomic PCR reactions, sense and antisense primers were synthesized as described above. PCR primers 1 and 2 were constructed from exonic sequences which were common to type 1 and 2 cDNAs (see FIGS. 6A–6B). Genomic DNA was isolated from cultured normal fibroblasts by standard methods (Sambrook et al., supra). PCR amplifications were performed for 30 cycles, and the amplified products were analyzed as described above. For DNA sequencing, the fragments were isolated from the agarose gels, subcloned into Bluescript vectors, and sequenced by the methods described above.

6.1.9. The Genomic Structure of ASM

A human genomic library (average insert size~10–15 kb) was constructed in the phage vector EMBL 3 (Promega) and kindly provided by Dr. Ruth Kornreich, Mount Sinai School of Medicine, NY. This library was screened at a density of ~10,000 plaques/150 mm petri dish using the full-length type 1 ASM cDNA, pASM-1FL (Schuchman et al., in review). Filter transfers and Southern hybridizations were performed by standard methods (Sambrook et al. 1989). Random primed labeling of the cDNA probe was performed using [α-$^{32}$P] CTP (~3000 Ci/mmol) (Amersham) according to the manufacturers instructions. Following three rounds of plaque purification, DNA was isolated from positive clones by the plate lysate method (Sambrook et al. 1989) and analyzed by Southern hybridization with oligonucleotides (17 mers) spanning the entire coding region of the full-length ASM cDNA. 5' end labeling of the oligonucleotides was performed with T4 polynucleotide kinase (New England Biolabs) and [γ-$^{32}$P] ATP (>5000 Ci/mmol) (Amersham). Oligonucleotide hybridizations were performed by standard methods (Sambrook et al. 1989).

Dideoxy sequencing was performed by the method of Sanger et al. using Sequenase DNA sequencing kits (United States Biochemical). An ~8 kb Sal I/Eco RI restriction fragment which contained the entire ASM coding region was isolated from an ASM genomic clone, ASMg-1, and digested with Hinc II (Promega) to generate four fragments of about 2.8, 2.0, 1.6 kb and 1.4 kb, respectively. The genomic restriction fragments were subcloned into the Bluescript vector, SK(+) (Stratagene), and sequenced in both orientations by double-stranded sequencing methods. Sequencing primers were synthesized on an Applied Biosystems DNA Synthesizer using phosphoramidite chemistry (Itakura et al. 1984). Computer analyses were performed using the University of Wisconsin Genetics Computer Group DNA Sequence Analysis Software (version 6.2) and GenBank (release 64) and NBRF (release 25) DNA and protein databases, respectively. The results of this analysis are depicted in FIGS. 6C–6H.

6.2. Results

6.2.1. Evidence for the Occurrence of Type 1 and 2 ASM Transcripts

Since only partial type 1 and 2 ASM cDNAs had been previously isolated from human placental and fibroblast cDNA libraries (Quintern et al., supra), Northern hybridization analyses were performed to determine the respective sizes and relative amounts of the type 1 and 2 transcripts. As shown in FIG. 1A, a single band of ~2.5 kb was detected when poly(A)$^+$ RNA from human placenta was hybridized with the partial type 1 cDNA (which could detect both type 1 and 2 transcripts). Longer exposures of up to 7 days did not reveal additional hybridizing bands (data not shown). Therefore, to demonstrate the occurrence of type 1 and 2 ASM transcripts, RNase protection experiments were carried out. As illustrated in the schematic (FIG. 1B, right), using a type 1 radiolabeled riboprobe (see "Methods"), it was expected that a type 1 transcript would have a 333-bp protected fragment, while a 266-bp fragment would be protected in a type 2 transcript. In human placental poly(A)$^+$ RNA, both type 1- and 2-specific transcripts were detected (FIG. 2B). Lanes 2 and 3 show 16- and 40-h exposures, respectively, while lane 1 was a control protection assay performed without the addition of poly(A)$^+$ RNA. Together with the Northern hybridization results, these experiments indicated that human placenta contained type 1 and 2 transcripts of ~2.5 kb. Furthermore, densitometric quantitation revealed that the type 2 transcripts represented from 5 to 10% of the total ASM placental RNAs, consistent with the previous cDNA library screening results.

To further demonstrate the occurrence of full-length type 2 cDNAs, PCR amplification experiments were performed using a sense primer from the 5' end of the full-length type 1 cDNA (pASM-1FL; see below) and an antisense primer constructed from the type 2-specific 40-bp region (FIG. 2C). As shown in FIG. 2A, a product of the expected size (~1.1 kb) was amplified, which specifically hybridized with an ASM-specific oligonucleotide probe (FIG. 2B). Control experiments also were performed using these primers to PCR-amplify the full-length type 1 cDNA (data not shown). As expected, no amplified products were found, demonstrating the specificity of this PCR for type 2-containing sequences. DNA sequencing of the amplified ~1.1-kb cDNA fragment revealed that the type 1 and 2 cDNAs had identical 5' sequences.

6.2.2. Isolation and Characterization of a Full-Length Human Type 1 ASM cDNA Since the longest type 1 and 2 ASM cDNAs previously isolated were 1879 and 1382 bp, respectively (Quintern et al., supra), intensive cDNA library screenings were undertaken to isolate the respective full-length ASM cDNAs. Screening of ~2×10$^6$ independent recombinants from a human placental cDNA library resulted in the isolation of 84 putative positive human ASM cDNA clones. Agarose gel electrophoresis and Southern hybridization analyses revealed that the cDNA inserts ranged from ~1.2 to 2.4 kb and that ~90% were type 1. Of the nine type 2 cDNAs isolated, the longest insert was ~1.4 kb.

Clone pASM-1FL, isolated from the placental library, contained the longest type 1 insert, a 2347-bp sequence which included an 87-bp 5'-untranslated region, an 1890-bp open reading frame encoding 629 amino acids, and a 370-bp 3'-untranslated region (FIGS. 3A–3C) (SEQ ID NO: 1). The coding region contained six N-glycosylation consensus sequences (encoding Asn-X-Thr/Ser) at residues 86–88, 175–177, 335–337, 395–397, 503–505, and 522–524. Although no poly(A)$^+$ tail was present, a consensus polyadenylation sequence was found at nucleotides 2254–2259, consistent with its position in pASM-1 and pASM-2 (Quintern, et al., supra). There were two in-frame ATGs present in the 5' region of the pASM-1FL insert, beginning at nucleotides 1 and 97. Using the von Heijne weight-matrix method (von Heijne, 1986, Nucleic Acids Res. 14:4683–4690), the signal peptidase cleavage site was optimally predicted after residue 46 (von Heijne score=10.8; FIG. 4, ). The next best signal peptide cleavage site was after residue 50 (von Heijne score=10.1). Interestingly, the predicted signal peptide consisted of a hydrophobic core sequence, which contained five repeats of the amino acid residues leucine and alanine; the corresponding nucleotide sequence contained a 12-nt tandem direct repeat at nucleotides 109–133.

The predicted amino acid sequence of the pASM-1FL insert was colinear with 111 microsequenced residues in tryptic peptides of ASM purified from human urine (Quintern et al., 1987, Biochim. Biophys. Acta 922:323–336). The four discrepancies between the predicted pASM-1FL amino acid sequence and the microsequenced peptides also occurred in the sequences predicted by the pASM-1 and pASM-2 inserts (Quintern, et al., 1989, supra). However, comparison of the predicted amino acid sequences of the full-length type 1 placental cDNA (pASM-1FL) and the previously reported type 1 (and 2) fibroblast cDNAs revealed two other differences. In the placental cDNA, codons 322 (ATA) and 506 (AGG) predicted isoleucine and arginine residues, respectively, whereas in the fibroblast cDNAs the predicted amino acids were threonine (322) and glycine (506) due to single base changes (ACA and GGG, respectively). Dot-blot hybridization studies of 20 normal Caucasian individuals with sequence-specific oligonucleotide probes (data not shown) revealed that the Gly-506 codon had an allele frequency of 0.7 and the Thr-322 codon has an allele frequency of 0.6, indicating that these nucleotide differences were common polymorphisms.

6.2.3. Isolation and Characterization of a Type 3 Human ASM cDNA

Since no full-length type 2 cDNAs were isolated from the placental library, efforts were directed to screen testis, retinal, and hepatoma cDNA libraries. Screening of ~2×10$^6$ independent recombinants from a human testis library with a type 2-specific 40-mer did not detect any type 2 cDNAs. Replica filters were then screened with the type 2 cDNA, pASM-2. Again, no type 2 cDNAs were identified, although 93 type 1 clones were isolated and analyzed. Next, a human retinal cDNA library was intensively screened with pASM-1FL. From ~5×10$^6$ independent recombinants screened, 26 putative positive ASM cDNAs were isolated and analyzed by Southern hybridization. Of these, there were 10 type 1 and one type 2 cDNAs. Again, only partial type 2 cDNAs were identified. The remaining cDNAS isolated from this library were too short to determine if they were type 1 or 2. Finally, ~1.0×10$^6$ recombinants in the hepatoma library were screened with an oligonucleotide constructed from the 5' end of pASM-1, the longest partial type 1 cDNA previously isolated. Five putative full-length ASM cDNAs were isolated; however, Southern hybridization analysis demonstrated that they had all type 1 cDNA inserts. Notably, restriction enzyme analysis of the 65 partial human ASM cDNAs isolated from the testis library revealed a third type of human ASM cDNA (pASM-3, type 3). As shown schematically in FIG. 4, the pASM-3 cDNA was 1914 bp and did not contain either the type 1-specific 172-bp region or the type 2-specific 40-bp sequences, but had a truncated open reading frame of 934 bp.

6.2.4. Reconstruction of Full-Length Type 2 and 3 cDNAs and Transient Expression of the Full-Length ASM cDNAs Since intensive screening of five different cDNA libraries did not identify full-length type 2 or 3 cDNAs, full-length sequences were reconstructed by the procedure shown in FIGS. 5A–5C to test their functional integrity. The reconstructions were based on the fact that PCR amplification and DNA sequencing studies (shown in FIG. 2 for the type 2 cDNA) had revealed that the full-length type 2 and 3 sequences existed in human placenta and that the 5' sequences were identical to that found in the full-length type 1 insert, PASM-1FL.

The pASM-1FL insert and the reconstructed full-length type 2 (pASM-2FL) and 3 (pASM-3FL) cDNAs were inserted into the transient expression vector, p-91023(B) (Kaufman et al., supra) and transfected into COS-1 cells. As shown in Table I, the mean endogenous ASM activity in COS-1 cells toward fluorescent natural substrate, N-12[(1-pyrenesulfonyl)amidododecanoyl]-sphingomyelinase was about 7.1 units/mg protein. The ASM activity in COS-1 cells transfected with the antisense constructs ranged from about 6.2 to 6.7 units/mg protein. In contrast, COS-1 cells transfected with the p-91023(B) full-length type 1 sense construct had 30.6 units/mg protein of ASM activity (~5-fold over endogenous levels), demonstrating that the pASM-1FL type 1 transcript expressed catalytically active enzyme. The reconstructed type 2 and 3 transcripts did not express catalytically active enzymes in COS-1 cells. None of the ASM full-length transcripts expressed neutral sphingomyelinase activities in COS-1 cells. As an additional control, the activity of another lysosomal enzyme, β-glucuronidase, also was determined and did not vary significantly from the endogenous levels in any of the transfection experiments.

TABLE I

Transient Experiments of Human Acid Sphingomyelinase in COS-Cells
Values represent the average of two independent determinations.

| Source | Acid sphingomyelinase | β-Glucuronidase |
|---|---|---|
| | nmol/h/mg | |
| COS-1 cells | 7.1 | 283 |
| Type 1 | | |
| Sense | 30.6 | 314 |
| Antisense | 6.7 | 338 |
| Type 2 | | |
| Sense | 6.7 | 307 |
| Antisense | 6.2 | 342 |

TABLE I-continued

Transient Experiments of Human Acid Sphingomyelinase in COS-Cells
Values represent the average of two independent determinations.

| Source | Acid sphingomyelinase | β-Glucuronidase |
|---|---|---|
| Type 3 | | |
| Sense | 7.4 | 288 |
| Antisense | 6.4 | 261 |

6.2.5. PCR Amplification of ASM Genomic DNA

In order to determine the origin of the type 1, 2, and 3 cDNAs, an ASM genomic region was PCR-amplified with primers constructed from common exonic sequences flanking the type 1- and 2-specific sequences (FIGS. 6A–6B). A 1665-bp PCR product was isolated and sequenced. This genomic region contained both the 172- and 40-bp type 1- and 2-specific sequences. Interestingly, the 172-bp type 1 sequence was exonic, flanked by 1052-bp and 229-bp introns. The 40-bp type 2-specific sequence was located at the 5' end of the 1052-bp intron. Within this intron there also were two poly(T) tracts of 20 and 23 nt at positions 313–332 and 469–491 and five potential lariat branch points (labeled a–e, FIG. 6). Within the 229-bp intron there are two potential lariat branch points that fit the consensus sequence, YNYURAY (Padgett et al., 1986, Annu. Rev. Biochem. 55: 1119–1150; Green, 1986, Annu. Rev. Genet. 20:671–708), at positions 1574–1580 and 1510–1516 (underlined in FIG. 6). The second potential branch point, 77 nt upstream from the A2 acceptor splice site, is followed by a polypyrimidine tract.

Table II shows the donor (D1 and D2) and acceptor (A1 and A2) splice site sequences at the intron/exon boundaries within this ASM genomic region, as well as the sequence of the cryptic donor splice site (D3) located adjacent to the 3' end of the 40-bp type 2-specific sequence. Note that neither of the donor sites within this region perfectly matched the consensus sequence (von Heijne, supra) and, in particular, there was a G to A transition within donor splice site D2, located at the 3' end of the type 1-specific.172-bp exon. Compared to the D1 and D2 donor sites, the D3 cryptic splice site adjacent to the 40-bp type 2-specific sequence best matches the donor consensus sequence.

TABLE II

5' Donor and 3' Acceptor Splice Sites in the PCR-Amplified Genomic ASM Region

| Splice site sequence | Nucleotide position | Donor | | Acceptor | |
|---|---|---|---|---|---|
| Consensus | | CAG | gtaagt | ncag | G |
| | | A | g | | T |
| D1 | 136–144 | CAG | gtactt | | |
| D2 | 1360–1368 | AAA | gtgagg | | |
| D3 | 176–184 | aag | gtgaat | | |
| A1 | 1187–1190 | | | tcag | A |
| A2 | 1588–1592 | | | ctag | G |

6.2.6. Stable Expression in CHO Cells

Recombinant clones stably expressing human ASM were obtained by electrotransfection of the p91-ASM construct into DG44 dhfr⁻ CHO cells and amplification of the integrated vector DNA with selection in increasing MTX concentrations. Initial growth in media lacking nucleosides resulted in the identification of over 20 clones expressing ASM at levels ranging from 5–30 units/mg. Clones with the highest ASM level were grown in the presence of 0.02 to 0.32 μM MTX to amplify the integrated p91-ASM DNA. The MTX induced amplification at 0.32 μM MTX resulted in the intracellular production of ASM at levels of over 300 units/mg. Importantly, human ASM was secreted into the media at levels at least five times over endogenous.

6.2.7. Engineering of Transgenic Mice Containing the Human ASM Gene

One of the most important goals of modern molecular biology is to understand how mammalian genes are regulated. Although in vitro expression systems have provided valuable insights into the mechanisms underlying mammalian gene regulation, to fully decipher the complex array of developmental and tissue-specific regulatory mechanisms operating in mammals, in vivo expression systems must be utilized. Clearly, one of the most powerful systems for the in vivo analysis of mammalian gene regulation is the use of transgenic mice. For example, we have been investigating the gene encoding the human lysosomal enzyme ASM. In order to study the regulation of this gene, a 12 kilobase (kb) ASM genomic fragment was isolated which included the complete coding region of the ASM polypeptide and about 4 kb of upstream sequences. This purified genomic fragment was given to the Transgenic Mouse Core Facility, where it was microinjected into about 30 mouse male pronuclei. Following microinjection, the pronuclei were implanted into pseudopregnant females and allowed to develop in vivo. Two founder animals were produced which contained the integrated human ASM gene. Both founder animals transmitted the human gene to their offspring, demonstrating that their germ cells contained the human ASM sequences. Interestingly, offspring from both founder animals expressed high levels of human ASM activity, suggesting that the sequences required for ASM transcriptional activity are contained within the 12 kb genomic fragment.

6.3. Discussion

Previously, we reported the isolation of partial type 1 and 2 cDNAs for human ASM, the longest inserts being 1879 (pASM-1) and 1382 (pASM-2) bp, respectively. Type 1 cDNAs had a unique 172-bp sequence encoding 57 amino acids which was replaced in the type 2 cDNAs by a 40-bp sequence encoding 13 different amino acids. About 90% of the 113 partial cDNAs isolated from human fibroblast and placental libraries were type 1. In the studies reported here, Northern hybridization analyses revealed the presence of a single ~2.5 kb transcript in placental poly(A)$^+$ RNA. Subsequent RNase protection studies demonstrated the occurrence of both type 1 and 2 transcripts. Thus, efforts were undertaken to isolate full-length type 1 and 2 ASM cDNAs by intensive screening of cDNA libraries from five different tissues.

Full-length type 1 cDNAs were isolated including the 2347-bp cDNA, pASM-1FL. The size of the pASM-1FL insert was consistent with the occurrence of the ~2.5 kb transcript observed in the Northern hybridization experiments, the 150-bp difference due to upstream 5'-untranslated sequences, and the length of the poly(A) tract. The full-length cDNA had an open reading frame of 1890 bp which contained two in-frame potential initiation codons. Since the enzyme's N terminus was blocked (Quintern et al., 1989, EMBO J 8:2469–2473), it is not known which initiation codon was used in vivo. It is possible that both initiation ATGs could be used as is the case for another hydrophobic lysosomal hydrolase, acid β-glucosidase (Sorge et al., 1987, Proc. Natl. Acad. Sci. U.S.A. 84:906–910). However, compared to the translation initiation consensus sequence GCC(AG)CCATGG (Kozak, 1987, Nucleic Acids Res. 15:8126–8149), the sequence flanking the second ATG in human ASM is weak, particularly since position –3 contains a thymidine residue. Therefore, it is likely that the first ATG is the in vivo initiation codon. Using the von Heijne weight-matrix method (von Heijne, 1986, Nucleic Acids. Res. 14:4683–4690), the optimal signal peptide cleavage would occur after amino acid residue 46. The predicted 14 amino acids preceding the signal peptide cleavage site have a particularly hydrophobic core consisting of five leucine/alanine repeats. Six potential N-glycosylation sites were predicted in the mature ASM polypeptide. At present it is not known which of the glycosylation sites are utilized. However, treatment of the purified urinary enzyme with glycopeptidase F reduced the molecular mass from –72 kDa to –61 kDa, indicating that perhaps as many as five sites may be glycosylated (Quintern, et al., supra).

Efforts to identify a full-length type 2 ASM cDNA included intensive screening of five libraries. Screening of placental and retinal libraries resulted in the identification of fourteen additional type 2 cDNAs ( )12% of the total cDNAs analyzed); however, none were longer than the previously obtained pASM-2 insert (1382 bp). Screening of hepatoma and testis libraries did not identify any type 2 clones, but a third 1914-bp ASM cDNA (type 3, pASM-3) was identified which lacked both the unique type 1 and 2 sequences.

In order to determine the functional integrity of the three different ASM transcripts, it was necessary to reconstruct full-length type 2 and 3 coding sequences (FIG. 5). Prior to performing these reconstruction experiments, the existence of full-length type 2 and 3 cDNAs was shown by PCR amplification of total placental cDNA (shown in FIG. 2 for the type 2 cDNA) and sequencing of the amplified products. Transient expression in COS-1 cells of pASM-1FL and the reconstructed type 2 and 3 cDNAs demonstrated that only the type 1 transcript was functional. The fact that the type 1 mRNA did not express neutral sphingomyelinase activity in COS-1 cells supports the notion that the acid and neutral sphingomyelinases are encoded by different genes.

Two nucleotide differences were initially identified by sequencing type 1 cDNAs from fibroblast and placental libraries (Quintern et al., supra). The functional integrity of the full-length pASM-1FL sequence from placenta (i.e. Ile-322 and Arg-506) was demonstrated by the transient expression of active enzyme in COS-1 cells (Table I). Subsequent analysis of genomic DNA from 20 unrelated individuals revealed that the base differences in codons 322 and 506 occurred in the Caucasian population as polymorphisms with allele frequencies of 0.6 and 0.7 for the Thr-322 and Gly-506 codons, respectively. The Gly-506 polymorphism creates MspI and NciI restriction sites.

The origin of the type 1, 2 and 3 transcripts was deduced by analysis of the PCR amplified genomic region, which included both the unique type 1 and 2 sequences (FIGS. 6A–6B) (SEQ ID NO: 3). The 172-bp type 1-specific sequence was an exon, flanked by introns of 1052 and 229 bp, whereas the 40-bp type 2-specific sequence was intronic, having been derived from the 5' end of the 1052-bp intron. No ASM transcripts were found which contained both the unique type 1- and 2-specific sequences. These findings are consistent with alternative splicing of a single ASM hnRNA. As shown diagrammatically in FIG. 7, type 1 transcripts result from normal splicing events which remove the 1052- and 229-bp introns, while type 2 transcripts result from splicing at a cryptic site which excises 1012 bp of the large intron, the 172-bp type 1 exon, and the 229-bp intron. The occurrence of the type 3 cDNA can be explained by alternative splicing to the upstream donor splice site, D1, thereby deleting the 172-bp exon.

Splicing of mammalian transcripts is initiated by cleavage at the 5' donor splice site followed by lariat formation at a branch point, generally within 50 nt of the 3' acceptor site (Padgett et al., 1986, Annu. Rev. Biochem. 55:1119–1150; Green, 1986, Annu. Rev. Genet. 20:671–708). Then there is a cleavage of the 3' exon at the acceptor splice site and ligation of the adjacent exons. However, in the human ASM mRNA, there is a weak 5' donor splice site adjacent to the 172-bp exon (D2, Table II) that does not function in about 10% of the splicing events, thereby generating the type 2 or 3 transcripts. As shown in FIG. 7, if the cryptic donor splice site (D3) adjacent to the 40-bp intronic sequence is used, a type 2 transcript is generated. The G to A transition of the nucleotide immediately adjacent to the invariant GT consensus dinucleotide in D2 may be particularly important, since this alteration has been shown to cause abnormal splicing of the proα1(I) collagen gene leading to Ehlers-Danlos syndrome Type VII (Weil, et al., 1989, EMBO J 8:1705–1710). In fact, the D3 cryptic splice site more closely matches the consensus sequence than either of the other two identified donor splice sites, D1 or D2, which are used to generate type 1 transcripts (Table II). The presence of two poly(T) tracts of 20 and 23 nt at the 5' end of the large intron may cause abnormal RNA secondary structure, perhaps favorably positioning the cryptic splice site, D3. The rare type 3 transcript also is generated by alternative splicing of the 172-bp exon, but in this case splicing proceeds to the upstream donor splice site D1, rather than to the D3 cryptic donor splice site.

Other features of the 1052-bp intron also deserve note. There are five potential lariat branch point sequences that fit the consensus sequence YNYURAY (Padgett, et al., supra) located near the 3' end of this intron (labeled a–e in FIG. 6A). Only one of these potential branch points is followed by a polypyrimidine tract (b), however this branch point is 336 bp upstream from the 3' acceptor site. It is generally assumed that the branch point should be within 20–50 nt of the 3' acceptor and not closer than 70 nt to the 5' donor site. Perhaps after cleavage at the D3 cryptic donor splice site, a lariat cannot efficiently form at branch points within this intron, and thus, the lariat occurs at the next available branch point, which is located in the 229-bp intron.

Alternative splicing also occurs in the transcripts for two other human lysosomal enzymes, β-glucuronidase (Oshima et al., 1987, Proc. Natl. Acad. Sci. U.S.A. 84:685–689) and β-galactosidase (Morreau et al., 1989, J. Biol. Chem. 264:20655–20663). β-Glucuronidase cDNAs, which had an internal 153-bp deletion, were identified in human fibroblast and placental cDNA libraries. The shorter cDNA had lost an entire exon due to alternative splicing and expressed an enzyme protein that was not catalytically active in COS-1 cells. For β-galactosidase, two distinct groups of cDNA clones were isolated from human fibroblast cDNA libraries. The shorter cDNAs were missing two noncontiguous protein coding regions present in the full-length cDNAs and produced truncated proteins, which were targeted to the perinuclear region in COS-1 cells.

In summary, three types of human ASM transcripts have been identified. Genomic PCR amplification and sequencing studies demonstrated that each of the ASM transcripts were derived from a single mRNA. The type 1 transcript is the major ASM species and encodes a catalytically active enzyme. The type 2 and 3 ASM transcripts result from alternative splicing, most likely due to the presence of a weak donor splice site (D2) adjacent to the 172-bp type 1-specific exonic sequence. Reconstruction and transient expression of full-length type 2 and 3 transcripts revealed that these sequences did not encode functional enzymes. The availability of the full-length type 1 cDNA will permit characterization of the human ASM gene and structure/function studies of the ASM polypeptide, as well as investigations of the mutations which cause the neuronopathic and non-neuronopathic forms of Niemann-Pick disease.

7. Example: Niemann-Pick Disease: a Frequent Missense Mutation in the Acid sphingomyelinase-Encoding Gene of Ashkenazi Jewish Type A and B Patients

7.1. Materials and Methods

7.1.1. Cell Lines

Primary cultures of fibroblasts and lymphoblasts were established from skin biopsies and peripheral blood samples obtained from NPD patients and family members and from normal individuals; informed consent was obtained. NPD cell lines GM00112A, GM00165, GM00370, GM00406, GM00559, GM02895, and GM03252 were obtained from the National Institute of General Medical Sciences Human Genetic Mutant Cell Repository Institute for Medical Research (Camden, N.J.). Cell lines 444X.F01, 534R.F03, 556X.F01, 888V.F01, 2789X.F01, 4293Q.E02, 4774Z.F01, 5113C.L01, 5115E.F01, and 6791M.F01 were obtained from the Service de Biochimie, Hospice de Lyon (Lyon, France). Cell lines DMN 83.126, DMN 84.135, DMN 86.40, DMN 86.49, DMN 87.71, DMN 87.99, DMN 88.9, DMN 83.133, GJO, and RNS were provided by Peter Penchev (Developmental and Metabolic Neurology Branch, National Institute of Neurological and Communicative Disorders and Stroke). The cells were grown in RPMI 1640 medium/10% fetal bovine serum/1% penicillin/streptomycin at 1 mg/ml by standard procedures (Bernstein, et al., 1989, J. Clin. Invest. 83:1390–1399). The diagnosis of types A and B NPD was based on clinical criteria (e.g., age at onset, presence of neurologic involvement, etc.) and by demonstration of markedly deficient ASM activity in cultured cells (Klar et al., 1988, Clin. Chim. Acta 176:259–268).

7.1.2. Enzyme and Protein Assays

ASM activity was determined in cultured fibroblasts obtained from NPD patients and normal individuals using the fluorescent natural substrate. [N-12(1-pyrenesulfonyl) amino dodecanoyl]sphingomyelin as described (Klar, et al., supra). One unit of activity equals that amount of enzyme that hydrolyzes 1 nmol of substrate per hr. Protein was determined by a modified fluorescamine assay (Bishop and Desnick, 1981, J. Biol. Chem. 256:1307–1316).

7.1.3. cDNA and Genomic Amplification and Sequencing of the Mutant Allele

Total RNA and genomic DNA were isolated from cultured skin fibroblasts by standard procedures (Sambrook et al., 1989, Molecular Cloning: A Laboratory Manual, Cold Spring Harbor Laboratory, Cold Spring Harbor, N.Y.). First-strand cDNA was reverse-transcribed from )5 μg of total RNA by using a cDNA synthesis kit according to the manufacturer's instructions (Boehringer Mannheim). The cDNA ( )10% of the total reaction) or genomic DNA ( )0.5 µg) was amplified by the PCR with Thermus acquaticus (Taq) polymerase (Perkin-Elmer Cetus) using a Perkin-Elmer Cetus thermalcycler, essentially as described by Saiki et al. (Saiki et al., 1988, Science 239:487–491) with the following conditions and modifications. PCR was performed for 30 to 40 cycles and consisted of denaturation for 1 minute at 94° C. and hybridizing and extension for 4 minutes at 66° C. To improve the specificity of the PCR amplification, a "PCR boost" procedure was used. In this procedure the concentrations of the primers and Taq polymerase were 0.1 µM and 5 units/ml, respectively, for the first 15 cycles. Then each primer was added to a final concentration of 0.5 µM, and an additional 2 units of Taq polymerase was added to the reaction mixture. PCR amplification then proceeded for an additional 15–25 cycles.

Pairs of sense and antisense oligonucleotide primers were synthesized on an Applied Biosystems model 380B DNA synthesizer (Itakura, et al., 1984, Annu. Rev. Biochem. 53:323–356) and used to specifically amplify (i) the entire coding region of the reverse-transcribed type 1 ASM transcript in three overlapping cDNA fragments, (ii) the 1665-bp genomic region containing the alternatively spliced sequences in the type 1 and 2 ASM cDNAS (E.H.S., unpublished work) and (iii) a genomic region that included the point mutation for confirmation of the candidate missense mutation. To amplify a 984-bp fragment from the 5' end of the ASM cDNA, the 29-mer sense primer, P1(5'-AGTAGTCTCGAGACGGGACAGACGAACCA-3') (SEQ ID NO: 11) corresponded to ASM nucleotide (nt) –39 to –23 with an additional 12 nt that included an XhoI restriction site and the 31-mer antisense primer. P2 (5'-AGTAGTCTGCAGAGCAGGGTACATGGCACTG-3') (SEQ ID NO: 12) corresponded to ASM nt 926 to 945 with an additional 12 nt containing an EcoRI restriction site. To amplify an internal 383-bp fragment of the ASM cDNA, the 29-mer sense primer, P3 (5'-ATCATCAAGCTTGGGTAACCATGAAAGCA-3') (SEQ ID NO: 13), corresponded to ASM nt 947–964 with an additional 12 nt containing a HindIII restriction site, and the antisense 32-mer primer. P4 (5'-ATCATCGAATTCTACAATTCGGTAATAATTCC-3') (SEQ ID NO: 14), corresponded to ASM nt 1310 to 1330 with an additional 12 nt containing an EcoRI restriction site. To amplify a 789-bp 3' fragment from the ASM cDNA, a 19-mer sense primer, P5 (5'-CTCCACGGATCCCGCAGGA-3') (SEQ ID NO: 15), corresponded to ASM nt 1855 to 1203 and contained an internal BamHI restriction site, and an antisense 32-mer primer. P6 (5'-AGTAGTGTCGACTTGCCTGGTTGAACCACAGC) (SEQ ID NO: 16), corresponded to ASM nt 1955 to 1974 with an additional 12 nt containing a SalI restriction site. Primers P3 and P4 also were used to amplify the 1665-bp internal genomic region that contains the alternatively spliced type 1 and 2 cDNA sequences. To confirm the candidate mutation by genomic sequencing and dot-blot analysis (see below) a 27-mer sense primer, P7 (5'-AGTAGTCGACATGGGCAGGATGTGTGG-3') (SEQ ID NO: 17), was used with antisense primer P6 to amplify a 567-bp genomic fragment containing the G-T transversion.

After PCR amplification, the PCR products were isolated from agarose gels and subcloned into either Bluescript KS (+) (Stratagene) or pGEM Zf (–) (Promega) vectors. For each amplified product, from four to six independent subclones were sequenced in both orientations by the dideoxy-nucleotide chain-termination method (Sanger et al., 1977, Proc. Natl. Acad. Sci. U.S.A. 74:5463–5467).

7.1.4. Dot-Blot Analysis

Any nucleotide change that occurred in more than two subcloned PCR products was considered a candidate mutation and analyzed by dot-blot hybridization with ASOs. In addition, ASOs were constructed and used as probes to analyze amplified genomic DNA from normal individuals and NPD patients and family members. From these studies genomic DNA was rapidly isolated from either whole blood or cultured cells by the following procedure. About 0.5 ml of whole blood and 0.5 ml of lysis buffer (10 mM Tris/HCl buffer, pH 7.5/5 mM $MgCl_2$/0.32 M sucrose/1% Triton X-100) were mixed at room temperature. After centrifugation at 13,000×g, the supernatant was removed, and 0.5 ml of PCR buffer (10 mM Tris HCl, buffer pH 8.3/50 mM KC1/2.5 mM $MgCl_2$/gelatin at 0.1 mg /ml/0.45% NonidetP40/45% Tween 20/proteinase K at 0.1 mg/ml) was added. For cultured cells, the lysis step was omitted, and the washed cell pellets were resuspended directly in PCR buffer (approximately $5×10^6$ cells per ml). The samples were then incubated at 60° C. for 1 hour and boiled for 10 minutes to inactivate the protease; then 25 µl was removed for PCR amplification. After agarose gel electrophoresis of the PCR products, the concentration of each product was estimated by ethidium bromide staining. For each sample, approximately 5 µg of DNA was used for the dot-blot analysis.

For the analysis of the R496L mutation, the 567-bp PCR product amplified from genomic DNA was analyzed by dot-blot hybridization (Sambrook et al, supra) by using Zetabind nylon membrane (AMF Cuno) and a Bio-Rad dot-blot apparatus. Hybridizations were performed for at least 3 hours at 39° C. After hybridization, the blots were washed at room temperature for 15 minutes in 6×SSC (1×SSC is 0.15M sodium chloride/0.015 M sodium citrate, pH 7.0/0.1% SDS) and then for 2 hr in the same solution at either 53° C. for the normal (5'-CTATTTGGTACACACGG-3') (SEQ ID NO: 18) or 48° C. for the mutation-specific (5'-CTATTTGGTACACAAGG-3') (SEQ ID NO: 19) oligonucleotides.

7.2. Results

7.2.1. Identification of the R496L Mutation in an Ashkenazi Jewish Type A NPD Patient To determine the molecular lesions in an Ashkenazi Jewish Type A NPD patient (proband 1), who had ~1% of normal ASM activity in cultured fibroblasts, total RNA was isolated from cultured lymphoblasts and reversed-transcribed into cDNA; then the entire coding region was PCR amplified. Nucleotide sequencing of the subcloned PCR products revealed a single point mutation in a CpG dinucleotide, a G-T transversion of nt 1487 of the full-length cDNA (FIG. 1). This transversion predicted R496L (SEQ ID NO: 34) in the ASM polypeptide. All other base substitutions occurred in only one or two of the subcloned PCR products analyzed.

To confirm the authenticity of this candidate mutation, a 567-bp region of genomic DNA from the proband, various family members, and 90 normal Ashkenazi Jewish individuals was PCR amplified and then hybridized with normal and R496L-specific radiolabeled oligonucleotides. As shown in FIG. 2C, the PCR-amplified genomic DNA from proband 1 hybridized to the mutation-specific, but not to the normal ASO, confirming the authenticity of the transversibn and indicating that proband 1 was homoallelic for the R496L mutation. Of the nine other family members studied, both parents, the paternal grandfather, and a paternal aunt were heterozygous for R496L. The maternal grandmother did not have the mutation, suggesting that the maternal grandfather was heterozygous for this mutation. There was no known consanguinity between the maternal or paternal grandfathers whose ancestors were from different European countries. Moreover, R496L was not found in any of the 180 ASM alleles studied from a group of normal Ashkenazi Jewish individuals, indicating that the G-T transversion was not a common polymorphism.

7.2.2. Occurrence of R496L in Ashkenazi Jewish and Non-Jewish NPD Type A Families The occurrence of R496L in other NPD families was determined by dot-blot analysis of genomic DNA from 17 unrelated Ashkenazi Jewish and 18 unrelated non-Jewish type A NPD families. As indicated in Table III, of the 31 Ashkenazi Jewish Type A NPD alleles studied (i.e., from 6 unrelated patients and 19 unrelated obligate heterozygotes), 32% had the R496L mutation. Only proband 1 was homoallelic for the mutation, whereas three obligate heterozygotes from unrelated families in which material from patients was unavailable were heterozygotes for the R496L mutation. In contrast, only 2 of 36 (5.6%) alleles had the R496L mutation in non-Jewish NPD type A patients, i.e., an American of German ancestry who was homoallelic.

TABLE III

FREQUENCY OF R496L IN ASHKENAZI JEWISH AND NON-JEWISH NPD FAMILIES WITH TYPES A AND B NPD

| Source | Unrelated families studied, no. | Mutant alleles studied. no. | R496L, % |
|---|---|---|---|
| Type A disease | | | |
| Ashkenazi Jewish | 17* | 31 | 32 |
| Non-Jewish | 18 | 36 | 5.6 |
| Type B disease | | | |
| Ashkenazi Jewish | 2 | 4 | 25 |
| Non-Jewish | 15 | 30 | 0.0 |

*In three of these families only one obligate heterozygous parent was available for analysis.

7.2.3. Occurrence of the R496L Mutation in Ashkenazi Jewish and Non-Jewish NPD Type B Families Analysis of genomic DNA from two unrelated Ashkenazi Jewish NPD type B patients revealed the presence of one R496L allele in one patient (designated proband 2). In contrast, the R496L allele was not found in genomic DNAs from 15 non-Jewish NPD type B patients (Table III).

7.2.4. Occurrence of the L302P Mutation in Jewish NPD Type A Families

The full-length ASM cDNA was PCR-amplified from a severely affected Ashkenazi Jewish Type A patient, proband 4. The methods for mRNA isolation, reverse transcription and PCR amplification were the same as those described above for the identification of the R496L mutation. DNA sequencing of the subcloned PCR products from proband 4 revealed a single T to C transition of nucleotide 905 which predicted the substitution of a proline for a leucine at amino acid residue 302 of the ASM polypeptide (L302P) (SEQ ID NO: 36). Dot-blot hybridization analysis with ASOs demonstrated that proband 4 was homoallelic for the L302P mutation. For the dot-blot analysis, a 606 bp region of the ASM genomic region is PCR amplified using sense and antisense PCR primers A (5'-TCATCCTCGAGCACTGACCTGCACTGGG-3') (SEQ ID NO: 31) and B (5'-AGTAGTCGACTGCTAGAGCAATCAGAG-3') (SEQ ID NO: 25), respectively. The sequence of the ASOs was L302 (5'-GTCACAGCACTTGTGAG-3') (SEQ ID NO: 32) and P302 (5'-GTCACAGCACCTGTGAG-3') (SEQ ID NO: 33). The ASOs were hybridized for at least three hours at 37° C. and then washed for 2 hours at 50° C.(L302) and 48° C.(P302). To date, the L302P mutation has been found in about 25% of the ASM alleles studied from Ashkenazi Jewish Type A patients (8 of 32). In contrast, this lesion has not been identified in any non-Jewish type A NPD patients, nor has it been found in type B NPD patients or normal individuals. Thus, this mutation is specific to Ashkenazi Jewish individuals with type A NPD and, together with the R496L mutation, over 60% of the mutant ASM alleles in this population can be detected.

7.3. Discussion

Insights into the molecular nature of the remarkably distinct type A and B NPD phenotypes have been gained by the identification of a mutation in the ASM gene causing this lysosomal storage disease. The G-T transversion of coding nt 1487 occurred at a CpG dinucleotide, a known hotspot for point mutations (Coulondre et al., 1978, Nature 274:775–780) and predicted R496L in the ASM polypeptide. Homoallelism for R496L resulted in the severe neuronbpathic type A phenotype, as evidenced by proband 1, who had )1% of normal ASM activity. It is not known whether the substitution of the basic arginine for the more hydrophobic and neutral leucine residue altered the enzyme polypeptide catalytic activity, stability, or both, because monospecific anti-human ASM antibodies useful for immunoblotting are not currently available.

Of the 17 unrelated Ashkenazi Jewish type A families studies, 9 were either homoallelic or heteroallelic for this lesion. In this sample, the frequency of the R496L allele was 32%, indicating that this lesion is an important mutation in type A NPD among Ashkenazi Jewish patients. It is likely that there is another more frequent mutation or, perhaps multiple mutations, causing type A NPD in Ashkenazi Jewish patients. In contrast, analysis of 18 unrelated non-Jewish type A patients revealed the presence of the R496L allele in only 1 (a frequency of 5.6%). The occurrence of the R496L allele in these individuals may have resulted from an independent mutational event or the presence of Jewish ancestors in the non-Jewish families.

One of the two Ashkenazi Jewish type B NPD patients was heteroallelic for R496L. The other allele in this Jewish type B patient had a different ASM mutation, which presumably resulted in the synthesis of a partially functional ASM polypeptide, as this patient had )5% residual ASM activity in cultured fibroblasts. The fact that none of the 15 non-Jewish type B patients had the R496L allele suggests that this allele is extremely rare in type B disease outside of the Ashkenazi population. That R496L was not a common polymorphism in the Ashkenazi Jewish population was supported by the fact that it was not found in any of the 180 ASM alleles analyzed from normal Ashkenazi Jewish individuals; presumably, this individual was the first NPD heterozygote detected by molecular screening.

For the past three decades, the genetic mechanisms responsible for the high frequency of the mutations that cause Tay-Sachs disease, Gaucher disease, and NPD in the Ashkenazi Jewish population (gene frequencies of approximately 0.02, 0.02, and 0.005, respectively) have been the subject of interest and debate (Knudson and Kaplan, 1962, Cerebral Sphingolipidoses, eds. Aronson and Volk, Academic, New York, pp. 395–411; Chase and McKusick, 1972, Am. J. Hum. Genet. 24:339–340; Myrianthopoulous et al., 1972, Am. J. Hum. Genet. 24:341–342; Fraikor, 1977, Soc. Biol. 24:117–134; Myrianthopoulous and Melnick, 1977, Prog. Clin. Biol. Res. 18:95–196). Intrigued by the fact that all three of these disorders are lysosomal diseases resulting from enzymatic defects in the sphingolipid degradative pathway, investigators suggested that there may have been a common selective pressure for their high gene frequencies in the Ashkenazi Jewish population (Myrianthopoulous and Melnick, supra). Others argued that the. higher gene frequencies in Ashkenazi Jewish individuals could be due to higher mutation rates for these genes (Knudson and Kaplan, supra) or founder effect and genetic drift (Fraikor, supra). The recent identification of the mutations causing these three diseases in the Ashkenazi Jewish population has provided insight into this controversy. To date, three mutations in the β-hexosaminidase chain (localized to chromosomal region 15q23–24) have been identified as the cause of Tay-Sachs disease in almost all Ashkenazi Jewish patients. Two of these mutations result in the infantile form, a 4-bp insertion (Myerowitz and Costigan, 1988, J. Biol. Chem. 263:18587–18589) or a splice-site mutation (Myerowitz, 1988, Proc. Natl. Acad. Sci. U.S.A. 85:3955–3959), which account for approximately 80 and 20% of the mutant alleles, respectively. Affected Ashkenazi Jewish patients with the less frequent and milder chronic or adult-onset form all have been heteroallelic for a point mutation Gly-Ser at position 269;) and one of the two infantile-onset alleles. Type 1 Gaucher disease among Ashkenazi patients results from multiple mutations in the β-glucosidase gene (localized to chromosomal region 1q21–q31), the Asn-Ser (at position 370) allele occurring in )75% of the mutant alleles, whereas the other 25% include several other lesions (Tsuji et al., 1987, N. Engl. J.Med. 316:570–757). With the identification of the first mutation causing NPD, R496L, it appears that in the Ashkenazi Jewish population each of those sphingolipidoses results from a common mutation (i.e., approximately 70% or more of the mutant alleles) and at least one or more less frequent mutations in their respective genes. The fact that two or more mutant alleles in each gene occur frequently in this population argues for selection, rather than for a higher mutation rate or founder effect and genetic drift as the major mechanism responsible for their increased frequency. Although it is likely that the major mutation for each disease first became established in the Ashkenazi Jewish population by founder effect and genetic drift, the finding of two or more mutations in each of these genes supports a selective advantage. Because all three disorders involve defects in lysosomal enzymes that degrade sphingolipids, it is tempting to-suggest that a common selective agent, such as resistance to an adverse situation (e.g., an infectious disease), could have increased the heterozygote frequency by differential survival (thus, increased fitness) for individuals heterozygous for each of these disorders. Alternatively, heterozygosity for these mutations may have been selected for by unrelated pressures in the past. Although several hypotheses have been advanced (Myrianthopoulous and Melnick, supra Myrianthopoulous and Aronson, 1972, Advances in Experimental Medicine and Biology, eds., Volk and Aronson, Plenum, New York pp. 561–570), the nature of the selective advantages for these mutations remains unknown.

The identification of the R496L allele and other mutations in the ASM gene in types A and B NPD may provide information for genotype-phenotype correlations and permit more accurate genetic counseling for newly diagnosed cases in families without a previously affected individual. Identification of other mutations, particularly those with residual activity that cause type B disease, also may provide structure-function information and may facilitate delineation of the active-site region. Previously, the enzymatic detection of heterozygotes for NPD types A and B was not sufficiently reliable to permit mass voluntary screening in the Ashkenazi Jewish community. Thus, the identification of the R496L and other mutations in types A and B NPD will permit accurate heterozygote identification in families with these lesions as well as heterozygote screening and prevention of NPD in the general Ashkenazi of Jewish population, as has been the prototypic experience with Tay-Sachs disease (Kaback, 1977, Prog. Clin. Biol. Res. 18:1–7). Using molecular techniques, we and others (Riggs-Raine, et al., 1990, Engl. J. Med. 323:6–12) have already demonstrated the feasibility of molecular heterozygote screening for Tay-Sachs disease in the Ashkenazi Jewish population. The extension of such molecular screening to include the more common mutations causing Gaucher disease and NPD by the use of multiplex PCR should permit the simultaneous screening and prevention of all three sphingolipidoses in the Ashkenazi Jewish population.

8. Example: Niemann-Pick Type B Disease:
Identification of a Single Codon Deletion in the
Acid Sphingomyelinase Gene and Genotype/
Phenotype Correlations in Type A and B Patients 8.1. Materials and Methods 8.1.1. Cell Lines Primary cultures of fibroblasts and lymphoblasts were established. from skin biopsies and peripheral blood samples obtained with informed consent from NPD patients and family members, and from normal individuals. NPD lines GM00112A, GM00165, GM00370, GM00406, GM00559, GM02895, and GM03252 were obtained from the Human Genetic Mutant Cell Repository (Camden, N.J.). Cell lines 444X.F01, 534R.F03, 556X.F01, 888V.F01, 2789X.F01, 42.93Q.E02, 4774Z.F01, 5113C.L01, 5115E.F01, and 6791M.F01 were obtained from the Service de Biochimie, Hospice de Lyon (Lyon, France). Cell lines DMN 83.126, DMN84.135, DMN 84.87, DMN 86.49, DMN 87.71, DMN 87.99, DMN 88.12, DMN 88.9 and RNS were provided by Dr. Peter Penchev, Developmental and Metabolic Neurology Branch, National Institute of Neurological and Communicative Disorders and Stroke. The cells were grown in RPMI 1640 media supplemented with 10% fetal bovine serum, 1% penicillin and 1 mg/ml streptomycin by standard procedures (Bernstein et al., 1989 Journal of Clin. Invest. 83: 1390–1399). The diagnosis of Types A or B NPD was based on clinical criteria (e.g., age at onset, presence of neurologic involvement, etc.) and by demonstration of markedly deficient ASM activity in cultured cells (Klar et al., 1988, Clin Chimica Acta 176:259–268). Clinical data on probands 1 and 2 have been published (Crocker, 1961, J. Neurochem. 7:69–78; Levran et al., in press, Proc. Natl. Acad. Sci. U.S.A.), and information on proband 3 was provided by Dr.

M. Vanier, Department of Biochemistry, Faculte de Medecine, Lyon, France.

8.1.2. Enzyme and Protein Assays

ASM activity was determined in cultured fibroblasts obtained from NPD patients and normal individuals using the fluorescent natural substrate, [N-12(1-pyrenesulfonyl) amido-dodecanoyl]sphingomyelin ($PSA_{12}$-sphingomyelin) as previously described (Klar et al., supra). One unit (U) of activity equals that amount of enzyme that hydrolyzes one nanomole of substrate per hour. Protein determinations were performed by a modified fluorescamine assay (Bishop and Desnick, 1981, J. Biol. Chem. 256:1307–1316).

8.1.3. cDNA and Genomic Amplification and Sequencing

For ASM cDNA amplification and sequencing, total RNA was isolated from cultured cells by standard procedures (Sambrook et al., 1989, Molecular Cloning, A Laboratory Manual, Cold Spring Harbor Laboratory Press, Cold Spring Harbor, N.Y.). First-strand cDNA was synthesized with reverse transcriptase from approximately 5 µg of total RNA using a cDNA synthesis kit according to the manufacturer's instructions (Boehringer-Mannheim, Indianapolis, Ind.). The ASM cDNA (approximately 10% of the total reaction) was PCR-amplified (Saiki et al., 1988, Science 239:487–491) with Taq polymerase (Perkin-Elmer Cetus, Norwalk, Conn.) using the previously described oligonucleotide primers (Levran et al., in press, Proc. Natl. Acad. Sci. U.S.A.). PCR was performed for 30 cycles, each consisting of denaturation for 1 minute at 94° C. and annealing and extension for 4 minutes at 72° C. Following amplification, the PCR products were isolated from agarose gels and subcloned into either Bluescript KS (+) (Stratagene, La Jolla, Calif.) or pGEM 9Zf (−) (Promega, Madison, Wis.) vectors. For each amplified product, from four to ten independent subclones were sequenced in both orientations by the dideoxy method (Sanger et al., 1977, Proc. Natl. Acad. Sci. U.S.A. 74:5463–5467).

To confirm the candidate mutation, genomic DNA was isolated from the proband (Bernstein et al., 1989, J. Clin. Invest. 83:1390–1399) and a 567 bp genomic fragment containing the mutation was PCR-amplified using sense (5'-AGTAGTCGACATGGGCAGGATGTGTGG-3') (SEQ ID NO: 17) and antisense (5'-AGTAGTGTCGACTTGCCTGGTTGAACCACAGC-3') (SEQ ID NO: 16) primers synthesized on an Applied Biosystems (Foster City, Calif.) Model 380B DNA Synthesizer (Itakura et al., 1984, Ann. Rev. Biochem. 53:323–356). The amplified genomic fragment was isolated, subcloned and sequenced as described above for the PCR-amplified ASM cDNAs.

8.1.4. Dot-Blot Analysis of the Mutant Alleles

For detection of the ΔR608 mutation in other NPD patients, their parents and relatives, as well as normal individuals, total genomic DNA was isolated, PCR-amplified as described above, and the 567-bp ASM product was analyzed by dot-blot hybridization using Zetabind nylon membranes (AMF-Cuno, Meriden, Conn.) and a Bio-Rad (Richmond, Calif.) dot-blot apparatus. Hybridization of the PCR product with the normal ASOs (5'-CTCTGTGCCGCCACCTG-3') (SEQ ID NO: 20) or with the ΔR608 ASO (5'-GCTCTGTGCCACCTGAT-3') (SEQ ID NO: 21) were performed for at least 3 hours at 39° C. 5' end labeling of the ASOs with T4 polynucleotide kinase and [γ-32P]ATP ("5000 Ci/mmole) was performed by standard procedures (Sambrook et al., supra). Following hybridization, the blots were washed at room temperature for 15 minutes in 6×SSC containing 0.1% SDS, and then 2 h in the same solution at either 54° C. for the normal ASO or 50° C. for the ΔR608 ASO. Dot-blot analysis of the R496L mutation was performed as previously described (Levran et al., supra).

8.2. Results

8.2.1. Identification of the ΔR608 Mutation in an Ashkenazi Jewish Patient with Type B NPD Previous studies of an Ashkenazi Jewish Type B NPD patient (proband 2; cell line MS 1271) indicated that he had about 5–8% residual ASM activity and that he was heteroallelic for the R496L mutation (Levran et al., supra). To identify the molecular lesion in his other ASM allele, total RNA from the proband was reverse-transcribed, the ASM coding region was PCR-amplified and the PCR products were subcloned into plasmid vectors for DNA sequencing. A three base deletion (CCG) of nucleotides 1821 –1823 in the full-length ASM cDNA (Schuchman et al. JBC, in press) was identified which predicted the removal of a single arginine residue in position 608 of the ASM polypeptide (designated ΔR608). The authenticity of this deletion was determined by genomic sequencing (FIG. 8) and by dot-blot hybridization of PCR-amplified genomic DNA from proband 2 and other family members using an ASO specific for the ΔR608 (SEQ ID NO: 35) mutation (FIG. 9). In addition, dot-blot hybridizations confirmed the ΔR608/R496L genotype of proband 2, and demonstrated that the ΔR608 and R496L mutations were transmitted from his father and mother, respectively. Proband 2's brother did not receive either mutant ASM allele. The ΔR608 mutation was not identified in over 100 ASM alleles from normal individuals, indicated that the deletion was not a polymorphism.

8.2.2. Occurrence of the ΔR608 Mutation in Types A and B NPD

Table IV shows the occurrence of the ΔR608 mutation in the ASM alleles of other patients and obligate heterozygotes with Types A and B NPD, as determined by dot-blot analysis of PCR-amplified genomic DNA. Interestingly, a second, unrelated Ashkenazi Jewish Type B NPD patient was heteroallelic for the ΔR608 mutation and another, unknown mutant ASM allele. Of the 15 non-Jewish Type B patients studied, only one, an Arab from Algeria (proband 3; cell line 534R.F03) was homoallelic for this mutation. This 21 year old male had a mild Type B phenotype (M. T. Vanier, personal communication). Of the 67 ASM alleles from Type A NPD patients or obligate heterozygotes (26 and 19 unrelated Ashkenazi Jewish and non-Jewish individuals, respectively), none had the ΔR608 mutation.

TABLE IV

FREQUENCY OF ΔR608 MUTATION IN
ASHKENAZI JEWISH AND NON-JEWISH
FAMILIES WITH TYPES A AND B NPD

| Source | Unrelated families studied | Mutant alleles studied | ΔR608 |
|---|---|---|---|
| NPD Type B | | | |
| Ashkenazi Jewish | 2 | 4 | 50.0 |
| Non-Jewish | 15 | 30 | 6.7 |
| NPD Type A | | | |
| Ashkenazi Jewish | 17 | 31 | 0.0 |
| Non-Jewish | 18 | 36 | 0.0 |

8.2.3. Comparison of the Residual ASM Activities in Type A and B NPD Patients Table V shows the ASM activities in cultured fibroblasts from probands 1, 2 and 3, which were determined using the fluorgenic natural substrate, $PSA_{12}$-sphingomyelin. Normal individuals had a mean activity of 46.3 nmol cleaved/h/mg. In contrast, Type A proband 1, who was homoallelic for R496L, had less than 1% of normal activity. Type B proband 2, whose genotype was R496L-ΔR608 had a residual activity of about 5% of normal, whereas proband 3 who was homoallelic for ΔR608 had about 13% of normal mean ASM activity, indicating that the ΔR608 allele expressed functional ASM activity in a dosage dependent manner.

TABLE V

GENOTYPE/PHENOTYPE CORRELATIONS
IN NIEMANN-PICK TYPES A AND B DISEASE

| Genotype | Phenotype | ASM Activity mean (range) (nmol/h/mg) | % of normal mean |
|---|---|---|---|
| R496L/R496L (proband 1) | Type A | 0.33 (0.21–0.47) | 0.7 |
| R496L/ΔR608 (proband 2) | Type B | 2.23 (1.8–2.3) | 4.8 |
| ΔR608/ΔR608 (proband 3) | Type B | 5.95 (5.1–6.9) | 12.8 |

The mean ASM activity in three normal individuals was 46.3 nmol/h/mg (range 37.5–61.0 nmol/h/mg).

8.3. Discussion

In 1966, Brady et al. reported that the primary enzymatic defect in Type A NPD was the deficient activity of ASM (Brady et al., 1966, Proc. Natl. Acad. Sci. USA 55:366–369). In the following year, Schneider and Kennedy demonstrated that ASM activity also was markedly decreased in patients with the milder, visceral form of NPD now known as Type B disease (Schneider and Kennedy, 1967, J. Lipid. Res. 8:202–206). Subsequent biochemical analyses of additional patients confirmed these findings (Levade et al., 1986, J. Clin. Chem. Clin. Biochem. 24:205–220; Poulos et al., 1984, Pediat. Res. 18:1088–1092; Besley and Elleder, 1986, J. Inher. Metab. Dis. 9:59–71) and somatic cell genetic studies demonstrated that the mutations causing Types A and B disease were allelic (Besley et al., 1980, Hum. Genet. 54:409–412). These findings stimulated investigators to speculate that the remarkable clinical heterogeneity observed among Type A and B NPD patients was due to different mutations in the ASM gene which resulted in altered enzyme polypeptides that expressed varying amounts of residual activity (e.g., Rousson et al., 1986, Immunologic studies on acidic sphingomyelinases. Enzymes of Lipid Metabolism II, New York, Plenum Publishing Corp., NY 273–283; Jobb, supra). However, efforts to reliably predict either the disease subtype or the severity of Type B patients by the amount of residual ASM activity have not been possible, in part due to the inability of assay procedures to accurately distinguish between patients with low levels of residual ASM activity and/or the presence of the neutral sphingomyelinase activity in cell homogenates (Chatterjee and Gosh, 1989, J. Biol. Chem. 264:12,554–12, 561). In addition, the inability to reliably discriminate obligate heterozygotes for Types A and B NPD from non-carriers by the determination of ASM activity in isolated leukocytes has precluded carrier screening for NPD.

Figures 10A, 10B:
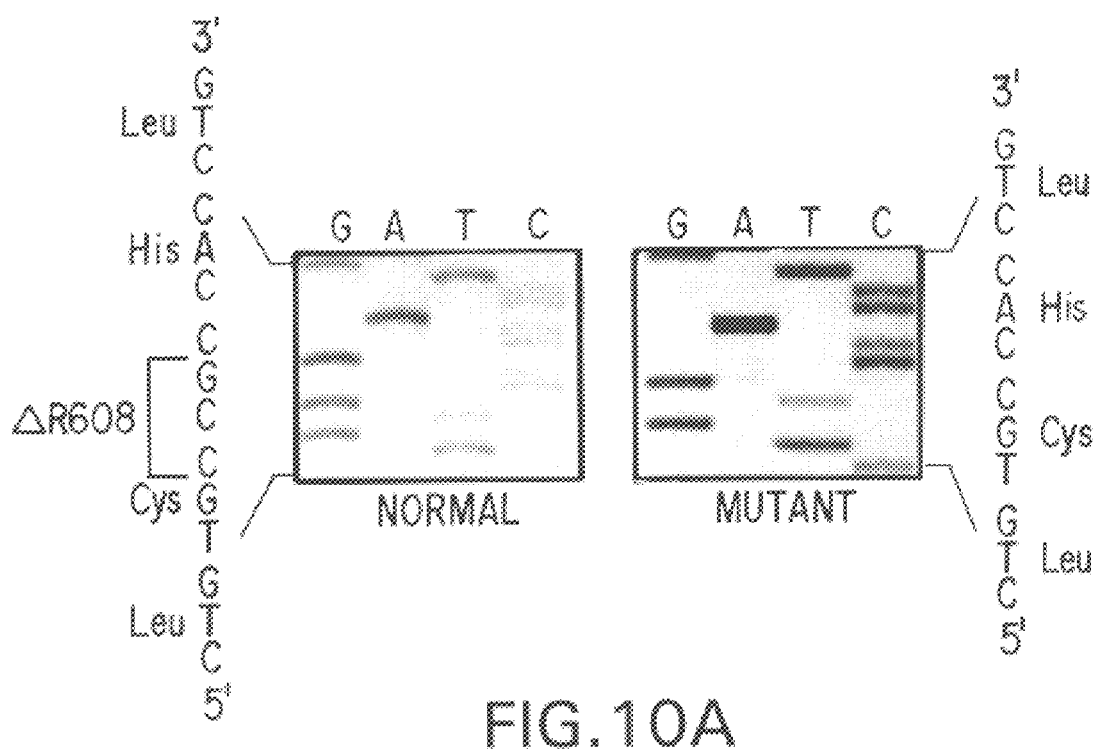

The recent cloning and sequencing of the ASM cDNA (Quintern et al., supra; Schuchman et al., in press, J. Biol. Chem.) has permitted identification of the first mutations which result in Types A and B NPD. Previously, the R496L mutation, due to a single G to T transversion, was found in 32% of the Ashkenazi Jewish Type A alleles studied. In contrast, it was present in only 5.6% of the non-Jewish Type A alleles analyzed (Levran et al., supra). In addition, proband 2, an Ashkenazi Jewish Type B NPD patient was found to be heteroallelic for the R496L mutation. In the present study, a three base deletion (ΔR608) in the ASM gene was identified as the other mutation in proband 2. As shown in FIG. 10B, the three base deletion, CCG, removed the last nucleotide of codon Cys-607 (TGC) and the first two nucleotides of codon Arg-608 (GCC). The new codon 607 formed by this deletion, TGC, also encoded a cysteine residue. Thus, the deletion resulted in the elimination of a single codon, 608, which encoded an arginine residue.

Detection of the R496L and ΔR608 mutations in patients with Types A and B NPD has permitted genotype/phenotype correlations and provided insights into the function of the altered enzymes encoded by these mutant alleles (Table II). The homoallelic (R496L/ΔR608) Type A patient who expresses less than 1% of normal ASM activity in cultured fibroblasts indicates that the R496L mutation encodes an ASM polypeptide with little, if any, catalytic activity and/or markedly decreased stability, thereby resulting the neuronopathic phenotype. In contrast, both heteroallelic (R496L/ΔR608) and homoallelic (ΔR608/ΔR608) Type B patients express an enzyme with sufficient residual activity to prevent neurologic manifestations. These findings suggest that the substitution of an arginine for a leucine at position 496 was more damaging to the enzyme's activity and/or stability than the deletion of an arginine residue in position 608. It follows that Type B patients who are homoallelic for ΔR608 would have a milder disease course than Type B patients who are heteroallelic for ΔR608 and a Type A mutation. Notably, proband 3 had comparatively milder disease manifestations than proband 2 at the same age. Thus, these genotype/phenotype correlations indicate that the more residual ASM activity expressed by the mutant alleles, the milder the disease manifestations. Ideally, in vitro expression would permit comparisons of the activity and stability of the residual enzymes expressed by each mutant ASM allele. However, it is likely that the residual activities expressed by the mutant alleles would be too low to permit biochemical characterization, particularly since eukaryotic expression systems (e.g., COS-1 cells, CHO cells) have endogenous ASM activity and prokaryotic systems do not perform the post-translational modifications (e.g., N-glycosylation) required for ASM activity.

The occurrence of genetic heterogeneity resulting in dramatically different phenotypes is a hallmark of the lysosomal storage diseases. A notable example in which the molecular lesions have been correlated with distinct phenotypes is Tay-Sachs disease (Neufeld, 1989, J. Biol. Chem. 264:10,927–10,930; Navon and Proia, 1989, Science 243:1471–1474). Mutations causing the classic, infantile form of Tay-Sachs disease have included deletions and splice site mutations in the β-hexosaminidase A α-chain gene that resulted in no detectable transcripts, whereas an exonic point mutation expresses sufficient enzymatic activity to result in the adult or chronic type of $GM_2$ gangliosidosis. Analogously, identification of the R496L and ΔR608 mutations has provided the first insights into the molecular lesions in the ASM gene underlying the remarkable phenotypic heterogeneity in NPD. Clearly, individuals who are homoallelic for the R496L mutation will have a severe neuronopathic phenotype and Type A NPD. The phenotype of patients heteroallelic for R496L will depend on the genetic lesion present on their other ASM allele. In contrast, patients who are either homo- or heteroallelic for the ΔR608 (e.g., probands 2 and 3) will most likely have Type B NPD. The identification of additional mutations causing Types A and B NPD should permit reliable genotype/phenotype correlations and provide further insights into the functional organization of the ASM polypeptide.

Various references are cited herein that are hereby incorporated by references in their entirety.

We claim:

1. An isolated acid sphingomyelinase polypeptide comprising SEQ ID NO: 2, wherein said polypeptide possesses ASM activity.

2. An isolated human acid sphingomyelinase polypeptide encoded by a nucleic acid which specifically hybridizes, under stringent conditions, to a nucleic acid having a nucleotide sequence as depicted in FIG. 3 (SEQ ID NO: 1) or FIG. 6B (SEQ ID NO:4), wherein said polypeptide possesses ASM activity.

3. A method of producing an isolated human acid sphingomyelinase polypeptide comprising the amino acid sequence of SEQ ID NO:2, comprising: (a) incubating a cell comprising a nucleic acid which encodes a functionally active human acid sphingomyelinase protein having an amino acid sequence of SEQ ID NO:2, under conditions wherein the nucleic acid sequence is expressed and the acid sphingomyelinase is produced; and (b) recovering the acid sphingomyelinase.

4. A method for treating a patient with Type B Niemann-Pick Disease comprising administering to the patient a therapeutically effective dose of a recombinant human acid sphingomyelinase or an isolated human acid sphingomyelinase comprising the amino acid sequence of SEQ ID NO: 2, or a recombinant variant thereof encoded by a nucleic acid which specifically hybridizes, under stringent conditions, to a nucleic acid having a nucleotide sequence as depicted in FIG. 3 (SEQ ID NO: 1) or FIG. 6B (SEQ ID NO: 4), wherein said variant possesses ASM activity.

5. The method of claim 4 wherein the therapeutically effective dose ranges from about 0.1 µg/kg body weight to about 10 mg/kg body weight.

6. The method of claim 4 wherein the therapeutically effective dose ranges from about 0.1 mg/kg body weight to about 2 mg/kg body weight.

7. The method of claim 4 wherein the recombinant acid sphingomyelinase or the recombinant variant is administered.

8. The method of claim 4 wherein the isolated human acid sphingomyelinase is administered.

9. An isolated human acid sphingomyelinase polypeptide of SEQ ID NO:2 comprising at least one silent amino acid change, wherein said polypeptide possesses ASM activity.

10. An isolated human acid sphingomyelinase polypeptide of SEQ ID NO:2 comprising at least one silent amino acid change, wherein the silent amino acid change is a deletion of at least one residue and said polypeptide possesses ASM activity.

11. An isolated human acid sphingomyelinase polypeptide of SEQ ID NO:2 comprising at least one silent amino acid change, wherein the silent amino acid change is an addition of at least one residue and said polypeptide possesses ASM activity.

12. An isolated human acid sphingomyelinase polypeptide of SEQ ID NO:2 comprising at least one silent amino acid change, wherein the silent amino acid change is a substitution of at least one residue and said polypeptide possesses ASM activity.

13. An isolated human acid sphingomyelinase polypeptide comprising SEQ ID NO: 2, wherein said polypeptide possesses ASM activity.

14. An isolated human acid sphingomyelinase polypeptide consisting essentially of SEQ ID NO: 2, wherein said polypeptide possesses ASM activity.

15. An isolated human acid sphingomyelinase polypeptide consisting of SEQ ID NO: 2, wherein said polypeptide possesses ASM activity.

16. An isolated human acid sphingomyelinase polypeptide comprising SEQ ID NO: 2.

17. An isolated human acid sphingomyelinase polypeptide consisting essentially of SEQ ID NO: 2.

18. An isolated human acid sphingomyelinase polypeptide consisting of SEQ ID NO: 2.

* * * * *

UNITED STATES PATENT AND TRADEMARK OFFICE
CERTIFICATE OF CORRECTION

PATENT NO.     : 6,541,218 B1
DATED          : April 1, 2003
INVENTOR(S)    : Edward H. Schuchman and Robert J. Desnick It is certified that error appears in the above-identified patent and that said Letters Patent is hereby corrected as shown below:

<u>Title page,</u>
Item [63], please insert the following:
    -- Related U.S. Application Data
Division of U.S. Application No. 07/695,472, filed May 3, 1991, now U.S. Patent No. 5,773,278. --

<u>Column 1,</u>
Line 4, please insert the following:
-- This is a division of application no. 07/695,472, filed May 3, 1991, the entire contents of which is incorporated herein by reference in its entirety. --

Signed and Sealed this

Ninth Day of September, 2003

JAMES E. ROGAN
*Director of the United States Patent and Trademark Office*